(12) United States Patent
Oliver et al.

(10) Patent No.: US 7,785,592 B2
(45) Date of Patent: *Aug. 31, 2010

(54) STABILIZED LIQUID ANTI-RSV ANTIBODY FORMULATIONS

(75) Inventors: Cynthia N. Oliver, North Potomac, MD (US); Erica Shane, McLean, VA (US); Benjamin S. Isaacs, Andover, MA (US); Christian B. Allan, Brookeville, MD (US); Stephen T. Chang, Frederick, MD (US)

(73) Assignee: MedImmune, LLC, Gaithersburg, MD (US)

( * ) Notice: Subject to any disclaimer, the term of this patent is extended or adjusted under 35 U.S.C. 154(b) by 73 days.

This patent is subject to a terminal disclaimer.

(21) Appl. No.: 11/906,543

(22) Filed: Oct. 1, 2007

(65) Prior Publication Data
US 2008/0286270 A1    Nov. 20, 2008

Related U.S. Application Data

(63) Continuation of application No. 11/362,267, filed on Feb. 24, 2006, now Pat. No. 7,294,336, which is a continuation of application No. 10/461,904, filed on Jun. 13, 2003, now Pat. No. 7,132,100.

(60) Provisional application No. 60/388,921, filed on Jun. 14, 2002.

(51) Int. Cl.
| *A61K 39/395* | (2006.01) |
| *A61K 39/40* | (2006.01) |
| *A61K 39/42* | (2006.01) |
| *C07K 16/00* | (2006.01) |

(52) U.S. Cl. .............. 424/133.1; 424/142.1; 424/147.1; 424/159.1; 530/387.1; 530/387.3; 530/388.1; 530/388.15; 530/388.3

(58) Field of Classification Search ........................ None
See application file for complete search history.

(56) References Cited

U.S. PATENT DOCUMENTS

| 4,360,457 A | 11/1982 | Ono et al. |
| 4,374,763 A | 2/1983 | Takagi |
| 4,517,304 A | 5/1985 | Stott et al. |
| 4,526,938 A | 7/1985 | Churchill et al. |
| 4,597,966 A | 7/1986 | Zolton et al. |
| 4,659,563 A | 4/1987 | Dobkin |
| 4,703,039 A | 10/1987 | Hawiger et al. |
| 4,717,766 A | 1/1988 | Dobkin |
| 4,760,026 A | 7/1988 | Lennox et al. |
| 4,800,078 A | 1/1989 | Ladner et al. |
| 4,853,326 A | 8/1989 | Quash et al. |
| 4,880,078 A | 11/1989 | Inoue et al. |
| 4,917,893 A | 4/1990 | Okada et al. |
| 4,992,419 A | 2/1991 | Woog et al. |
| 5,071,758 A | 12/1991 | Stott et al. |
| 5,128,326 A | 7/1992 | Balazs et al. |
| 5,137,804 A | 8/1992 | Greene et al. |
| 5,149,650 A | 9/1992 | Wertz et al. |
| 5,183,657 A | 2/1993 | Buurman |
| 5,194,595 A | 3/1993 | Wathen |
| 5,219,996 A | 6/1993 | Bodmer et al. |
| 5,223,254 A | 6/1993 | Paradiso et al. |
| 5,223,409 A | 6/1993 | Ladner et al. |
| 5,240,694 A | 8/1993 | Gwaltney, Jr. |
| 5,271,927 A | 12/1993 | Parker et al. |
| 5,279,935 A | 1/1994 | Nycz |
| 5,288,630 A | 2/1994 | Wathen |
| 5,290,540 A | 3/1994 | Prince et al. |
| 5,332,567 A | 7/1994 | Goldenberg |
| 5,332,805 A | 7/1994 | Carey et al. |
| 5,340,926 A | 8/1994 | Lowe et al. |
| 5,354,554 A | 10/1994 | Rhind |
| 5,391,478 A | 2/1995 | Greene et al. |
| 5,403,484 A | 4/1995 | Ladner et al. |
| 5,411,749 A | 5/1995 | Mayo et al. |
| 5,412,077 A | 5/1995 | Siber et al. |
| 5,418,136 A | 5/1995 | Miller et al. |

(Continued)

FOREIGN PATENT DOCUMENTS

| AU | 713113 | 11/1999 |
| AU | 2002219944 | 2/2008 |
| CA | 2197684 | 2/1996 |
| EP | 0 025 321 | 3/1981 |
| EP | 0 025 719 | 3/1981 |
| EP | 0 368 684 | 5/1990 |

(Continued)

OTHER PUBLICATIONS

Abbas et al., 1991. Cellular and Molecular Immunology—Chapter 3—Antibodies and Antigens, p. 45-47. W.B Saunders Company.

(Continued)

*Primary Examiner*—Mark Navarro
(74) *Attorney, Agent, or Firm*—Jones Day

(57) ABSTRACT

The present invention provides liquid formulations of SYNAGIS® or an antigen-binding fragment thereof that immunospecifically bind to a respiratory syncytial virus (RSV) antigen, which formulations exhibit stability, low to undetectable levels of aggregation, and very little to no loss of the biological activities of SYNAGIS® or an antigen-binding fragment thereof, even during long periods of storage. In particular, the present invention provides liquid formulations of SYNAGIS® or an antigen-binding fragment thereof which immunospecifically binds to a RSV antigen, which formulations are substantially free of surfactant, inorganic salts, and/or other common excipients. Furthermore, the invention provides method of preventing, treating or ameliorating symptoms associated with RSV infection utilizing liquid formulations of the present invention.

82 Claims, 2 Drawing Sheets

U.S. PATENT DOCUMENTS

| | | | |
|---|---|---|---|
| 5,422,097 A | 6/1995 | Gwaltney, Jr. |
| 5,424,189 A | 6/1995 | Oberst et al. |
| 5,468,606 A | 11/1995 | Bogart et al. |
| 5,470,736 A | 11/1995 | Verma et al. |
| 5,476,997 A | 12/1995 | Kaneshima et al. |
| 5,484,893 A | 1/1996 | Parker et al. |
| 5,496,703 A | 3/1996 | Babish et al. |
| 5,506,209 A | 4/1996 | Mukerji et al. |
| 5,518,725 A | 5/1996 | Daynes et al. |
| 5,530,102 A | 6/1996 | Gristina et al. |
| 5,534,411 A | 7/1996 | Weltzin |
| 5,538,733 A | 7/1996 | Emery et al. |
| 5,538,952 A | 7/1996 | Mukerji et al. |
| 5,571,698 A | 11/1996 | Ladner et al. |
| 5,585,089 A | 12/1996 | Queen et al. |
| 5,608,038 A | 3/1997 | Eibl et al. |
| 5,624,821 A | 4/1997 | Winter |
| 5,648,260 A | 7/1997 | Winter |
| 5,667,988 A | 9/1997 | Barbas et al. |
| 5,679,377 A | 10/1997 | Bernstein et al. |
| 5,693,762 A | 12/1997 | Queen et al. |
| 5,739,277 A | 4/1998 | Presta et al. |
| 5,747,035 A | 5/1998 | Presta et al. |
| 5,762,905 A | 6/1998 | Burton et al. |
| 5,811,524 A | 9/1998 | Brams et al. |
| 5,824,307 A | 10/1998 | Johnson et al. |
| 5,840,298 A | 11/1998 | Brams et al. |
| 5,855,913 A | 1/1999 | Hanes et al. |
| 5,866,125 A | 2/1999 | Brams et al. |
| 5,869,046 A | 2/1999 | Presta et al. |
| 5,871,736 A | 2/1999 | Bruegger et al. |
| 5,874,064 A | 2/1999 | Edwards et al. |
| 5,912,015 A | 6/1999 | Bernstein et al. |
| 5,916,597 A | 6/1999 | Lee et al. |
| 5,929,212 A | 7/1999 | Joliffe et al. |
| 5,934,272 A | 8/1999 | Lloyd et al. |
| 5,939,068 A | 8/1999 | Brams et al. |
| 5,955,364 A | 9/1999 | Brams et al. |
| 5,958,765 A | 9/1999 | Brams et al. |
| 5,961,927 A | 10/1999 | Isaacs et al. |
| 5,985,309 A | 11/1999 | Edwards et al. |
| 5,985,320 A | 11/1999 | Edwards et al. |
| 5,989,463 A | 11/1999 | Tracy et al. |
| 6,019,968 A | 2/2000 | Platz et al. |
| 6,096,551 A | 8/2000 | Barbas et al. |
| 6,117,980 A | 9/2000 | Gonzalez et al. |
| 6,121,022 A | 9/2000 | Presta |
| 6,165,745 A | 12/2000 | Ward et al. |
| 6,171,586 B1 | 1/2001 | Lam et al. |
| 6,194,551 B1 | 2/2001 | Idusogie |
| 6,277,375 B1 | 8/2001 | Ward |
| 6,413,771 B1 | 7/2002 | Brams et al. |
| 6,519,948 B2 | 2/2003 | Zorn |
| 6,528,624 B1 | 3/2003 | Idusogie |
| 6,537,809 B2 | 3/2003 | Brams et al. |
| 6,538,124 B1 | 3/2003 | Idusogie |
| 6,565,849 B2 | 5/2003 | Koenig et al. |
| 6,565,888 B1 | 5/2003 | Tracy et al. |
| 6,572,856 B1 | 6/2003 | Taylor et al. |
| 6,586,008 B1 | 7/2003 | Batycky et al. |
| 6,656,467 B2 | 12/2003 | Young et al. |
| 6,685,942 B1 | 2/2004 | Burton et al. |
| 6,737,056 B1 | 5/2004 | Presta |
| 6,818,216 B2 | 11/2004 | Young et al. |
| 6,855,493 B2 | 2/2005 | Young et al. |
| 7,083,784 B2 | 8/2006 | Dall'Acqua et al. |
| 7,132,100 B2 | 11/2006 | Oliver et al. |
| 7,179,900 B2 | 2/2007 | Young et al. |
| 7,208,162 B2 | 4/2007 | Prince et al. |
| 7,229,619 B1 | 6/2007 | Young et al. |
| 7,279,182 B2 | 10/2007 | Lipp et al. |
| 7,294,336 B2 | 11/2007 | Oliver et al. |
| 7,323,172 B2 | 1/2008 | Young et al. |
| 7,416,726 B2 | 8/2008 | Ravetch |
| 7,425,618 B2 | 9/2008 | Oliver et al. |
| 7,553,489 B2 | 6/2009 | Young et al. |
| 7,635,568 B2 | 12/2009 | Young et al. |
| 2001/0034062 A1 | 10/2001 | Koenig et al. |
| 2002/0004046 A1 | 1/2002 | Johnson |
| 2002/0018780 A1 | 2/2002 | Koenig et al. |
| 2002/0098189 A1 | 7/2002 | Young et al. |
| 2002/0102257 A1 | 8/2002 | Johnson |
| 2002/0177126 A1 | 11/2002 | Young et al. |
| 2004/0002587 A1 | 1/2004 | Watkins |
| 2004/0005323 A1 | 1/2004 | Brams et al. |
| 2004/0005324 A1 | 1/2004 | Pilkington et al. |
| 2004/0018200 A1 | 1/2004 | Oliver et al. |
| 2004/0018243 A1 | 1/2004 | Basu et al. |
| 2004/0038878 A1 | 2/2004 | Tanikawa et al. |
| 2004/0076631 A1 | 4/2004 | Brams et al. |
| 2004/0131609 A1 | 7/2004 | Young et al. |
| 2005/0002926 A1 | 1/2005 | Young et al. |
| 2006/0099220 A1 | 5/2006 | Tous et al. |
| 2006/0115485 A1 | 6/2006 | Losonsky et al. |
| 2006/0198840 A1 | 9/2006 | Dall'Acqua et al. |
| 2007/0048332 A1 | 3/2007 | Oliver et al. |
| 2007/0122403 A1 | 5/2007 | Dall'Acqua et al. |
| 2007/0196916 A1 | 8/2007 | Young et al. |
| 2008/0286270 A1 | 11/2008 | Oliver et al. |
| 2009/0175883 A1 | 7/2009 | Oliver et al. |

FOREIGN PATENT DOCUMENTS

| | | |
|---|---|---|
| EP | 0 420 649 | 9/1990 |
| EP | 0 413 622 | 2/1991 |
| EP | 0671927 | 9/1995 |
| EP | 0682040 | 11/1995 |
| EP | 0451216 | 1/1996 |
| EP | 0699756 | 3/1996 |
| EP | 0 327 378 | 12/1996 |
| EP | 1259547 | 9/2001 |
| EP | 1265928 | 12/2002 |
| EP | 1 314 437 | 5/2003 |
| FR | 2758331 | 7/1998 |
| JP | 1268646 A | 10/1989 |
| WO | WO 89/07142 | 8/1989 |
| WO | WO 90/07861 | 7/1990 |
| WO | WO 91/04743 | 4/1991 |
| WO | WO 91/05548 | 5/1991 |
| WO | WO 91/14438 | 10/1991 |
| WO | WO 92/05274 | 4/1992 |
| WO | WO 92/19244 | 11/1992 |
| WO | WO 93/05796 | 4/1993 |
| WO | WO 93/15199 | 8/1993 |
| WO | WO 93/15200 | 8/1993 |
| WO | WO 93/19197 | 9/1993 |
| WO | WO 93/20210 | 10/1993 |
| WO | WO 93/22332 | 11/1993 |
| WO | WO 94/06448 | 3/1994 |
| WO | WO 94/29351 | 12/1994 |
| WO | WO 95/04081 | 2/1995 |
| WO | WO 96/05229 | 2/1996 |
| WO | WO 96/20698 | 7/1996 |
| WO | WO 96/32478 | 10/1996 |
| WO | WO 96/40252 | 12/1996 |
| WO | WO 97/32572 | 9/1997 |
| WO | WO 97/34631 | 9/1997 |
| WO | WO 97/43316 | 11/1997 |
| WO | WO 97/44013 | 11/1997 |
| WO | WO 97/45140 | 12/1997 |
| WO | WO 98/23289 | 6/1998 |
| WO | WO 98/31346 | 7/1998 |
| WO | WO 98/33919 | 8/1998 |
| WO | WO 98/34594 | 8/1998 |

| | | |
|---|---|---|
| WO | WO 98/56418 | 12/1998 |
| WO | WO 99/15154 | 4/1999 |
| WO | WO 99/20253 | 4/1999 |
| WO | WO 99/28471 | 6/1999 |
| WO | WO 99/43713 | 9/1999 |
| WO | WO 99/51642 | 10/1999 |
| WO | WO 99/66903 | 12/1999 |
| WO | WO 00/09560 | 2/2000 |
| WO | WO 00/10541 | 3/2000 |
| WO | WO 00/29584 | 5/2000 |
| WO | WO 00/42072 | 7/2000 |
| WO | WO 00/56771 | 9/2000 |
| WO | WO 00/73346 | 12/2000 |
| WO | WO 01/55217 | 8/2001 |
| WO | WO 01/58957 | 8/2001 |
| WO | WO 01/64751 | 9/2001 |
| WO | WO 01/77137 | 10/2001 |
| WO | WO 02/11753 | 2/2002 |
| WO | WO 02/13860 | 2/2002 |
| WO | WO 02/43660 | 6/2002 |
| WO | WO 02/60919 | 8/2002 |
| WO | WO 03/054213 | 7/2003 |
| WO | WO 03/105894 | 12/2003 |
| WO | WO 03/106644 | 12/2003 |
| WO | WO 2004/010935 | 2/2004 |
| WO | WO 2004/016750 | 2/2004 |
| WO | WO 2004/029207 | 4/2004 |
| WO | WO 2004/035752 | 4/2004 |
| WO | WO 2004/083373 | 9/2004 |
| WO | WO 2006/034292 | 3/2006 |
| WO | WO 2007/002543 | 1/2007 |
| WO | WO 2009/003019 | 12/2008 |

OTHER PUBLICATIONS

Adams et al., 1998. Increased affinity leads to improved selective tumor delivery of single-chain Fv antibodies. Cancer Res. 58(3):485-90.
Adams et al., 1998. Prolonged in vivo tumour retention of a human diabody targeting the extracellular domain of human HER2/neu. Br J Cancer. 77(9):1405-12.
Ames et al., 1995. Conversion of murine Fabs isolated from a combinatorial phage display library to full length immunoglobulins. J Immunol Methods.184(2):177-86.
Arbiza et al., 1992. Characterization of two antigenic sites recognized by neutralizing monoclonal antibodies directed against the fusion glycoprotein of human respiratory syncytial virus. J Gen Virol. 73: 2225-2234.
Balint and Larrick, 1993. Antibody engineering by parsimonious mutagenesis. Gene. 137(1):109-118.
Barbas et al., 1996. Selection and evolution of high-affinity human anti-viral antibodies. Trends Biotech. 14(7):230-234.
Bennett et al., 2007, Immunopathogenesis of Respiratory Syncytial Virus Bronchiolitis, J Infect Dis: 195(10):1532-1540.
Berzofsky and Berkower, 1993. in Paul, W.E., Fundamental Immunology (Raven Press), Chapter 8: Immunogenicity and antigen structure, p. 242.
Berzofsky and Berkower, 1993. in Paul, W.E., Fundamental Immunology (Raven Press), Chapter 9: Structure and Function of Immunoglobulins, p. 292-295.
Better et al., 1988. *Escherichia coli* secretion of an active chimeric antibody fragment. Science. 240(4855):1041-3.
Blake et al., 1999. Automated Kinetic Exclusion Assays to Quantify Protein Binding Interactions in Homogeneous Solution. Analytical Biochemistry 272: 123-134.
Boder et al., 2000. Directed evolution of antibody fragments with monovalent femtomolar antigen-binding affinity. Proc Nati Acad Sci U S A. 97(20):10701-5.
Boeckh et al., 2001. Phase 1 Evaluation of the Respiratory Syncytial Virus-Specific Monoclonal Antibody Palivizumab in Recipients of Hematopoietic Stem Cell Transplants. J of Infect Dis. 184: 350-354.
Bourgeois et al., New peptides recognizing viral epitope with tropism to mucosa—useful for, e.g. diagnosing, preventing and treating viral infection(s). GENESEQ database entry for Accession No: AAW70933; Oct. 14, 1998 and alignment with Seq ID No. 12 of U.S. Appl. No. 09/771,415.

Brinkmann et al., 1995. Phage display of disulfide-stabilized Fv fragments. J Immunol Methods. 182(1):41-50.

Burton and Barbas, 1994. Human antibodies from combinatorial libraries. Adv. Immunol. 57:191-280.

Cao et al., 2003. Bispecific antibody conjugates in therapeutics. Adv Drug Deliv Rev. 55(2):171-97.

Carlsson et al., 1992. Human peripheral blood lymphocytes transplanted into SCID mice constitute an in vivo culture system exhibiting several parameters found in a normal humoral immune response and are a source of immunocytes for the production of human monoclonal antibodies. J Immunol. 1992; 148(4):1065-71.

Casset et al., 2003. A peptide mimetic of an anti-CD4 monoclonal antibody by rational design. Biochem Biophys Res Commun. 307(1):198-205.

Chamat et al., 1999. Human monoclonal antibodies isolated from spontaneous Epstein-Barr Virus—transformed tumors of Hu-SPL-SCID mice and specific for fusion protein display broad neutralizing activity toward respiratory syncytial virus. J Infect Dis. 180: 268-277.

Chanock et al., 1989. Respiratory syncytial virus. Viral Infections of Humans, Epidemiology and Control, 3rd Evans, ed., A.S. Chapter 20:525-544.

Chmura et al., 2001. Antibodies with infinite affinity. Proc Nat Acad Sci. 98(15):8480-8484.

Chothia et al., 1998. Structural determinants in the sequences of immunoglobulin variable domain. J Mol Biol. 278(2):457-79.

Chowdhury et al., 2005. Tailor-made antibody therapeutics. Methods. 36: 11-24.

Connors, 1990. Chemical Kinetics: The Study of Reaction Rates in Solution. p. 152.

Crowe et al., 1998. Monoclonal antibody-resistant mutants selected with a respiratory syncytial virus-neutralizing human antibody fab fragment (Fab 19) define a unique epitope on the fusion (F) glycoprotein. Virology. 252(2):373-5.

Crowe et al., 1993. Recombinant human respiratory syncytial virus (RSV) monoclonal antibody Fab is effective therapeutically when introduced directly into the lungs of RSV-infected mice, Proc Natl Acad Sci USA; 91:1386-1390.

Dall'Acqua, 2002. Increasing the Affinity of a Human IgGl for the Neonatal Fc Receptor: Biological Consequences. J of Immunol. 169: 5171-5180.

Delagrave et al., 1999. Effects of humanization by variable domain resurfacing on the antiviral activity of a single-chain antibody against respiratory syncytial virus. Protein Eng. 12(4):357-62.

De Vincenzo et al., 2005, Factors Predicting Childhood RespiratorySyncytial Virus Severity—What They Indicate About Pathogenesis, Ped Inf Dis; 24:S177-S183.

Downham et al., 1976. Breast-feeding protects against respiratory syncytial virus infections. Br Med J. 2(6030):274-6.

Edelman et al., 1969. The Covalent Structure of an Entire gammaG Immunoglobulin Molecule. PNAS 63:78-85.

Egan et al., 1999. Effect of Sch 55700, a humanized monoclonal antibody to human interleukin-5, on eosinophilic responses and bronchial hyperreactivity. Arzneimittel-forschung. 49(9):779-790.

Fahy and O'Byrne, 2001. Reactive Airways Disease. Am J Respir Crit Care Med. 163(4):822-3.

Foecking and Hofstetter, 1986. Powerful and versatile enhancer-promoter unit for mammalian expression vectors. Gene. 45:101-105.

Garcia-Barreno et al.1989. Marked Differences in the Antigenic Structure of Human Respiratory Syncytial Virus F and G Glycoproteins. J Virol. 63(2):925-32.

Gilchrist et al. 1994. National surveillance for respiratory syncytial virus, United States, 1985-1990. J Infect Dis. 170:986-990.

Gillies et al., 1989. High-level expression of chimeric antibodies using adapted cDNA variable region cassettes. J Immunol Methods. 125:191-202.

Goldstein, et al. 1993. We The American Elderly, U.S. Dept. of Commerce, Economics and Statistics Admin., Bureau of the Census.

Hall, 1987. Respiratory syncytial virus. Textbook of Pediatric Infectious Diseases, Feigin and Cherry, eds., WB Saunders, Philadelphia, 1653-1676.

Hammerling et al., 1981. in Monoclonal antibodies and T-cell hybridomas, Elsevier, NY. pp. 563-581.

Hefta et al, 1998. Kinetic and affinity constants of epitope specific anti-carcinembryonic antigen (CEA) monoclonal antibodies for CEA and engineered CEA domain constructs. Immunotechnology 4:49-57.

Hellstrom et al., 1987. Antibodies for drug delivery. Controlled Drug Delivery, Fundamentals and Applications 2nd edition. Chapter 15: p. 623-653.

Hemming et al., 1988. Topically Administered Immunoglobulin Reduces PulmonaryRespiratory Syncytial Virus Shedding in Owl Monkeys. Antimicrob Agents Chemother. 32(8):1269-1270.

Hudson and Souriau, 2003. Engineered Antibodies. Nature Medicine 9(1):129-34.

Ichiyoshi et al., 1995. A human anti-insulin IgG autoantibody apparently arises through clonal selection from an insulin-specific "germline" natural antibody template. Analysis by V gene segment reassortment and site-directed mutagenesis. J Immunol. 154(1):226-38.

Ifverson and Borrebaeck, 1996. SCID-hu-PBL: a model for making human antibodies? Semin Immunol. 8(4):243-8.

Jackson et al., 1998. Antigen specificity and tumour targeting efficiency of a human carcinoembryonic antigen-specific scFv and affinity-matured derivatives. Br. J. Cancer. 78(2):181-8.

Johnson et al., 1991. Development of humanized monoclonal antibodies which neutralize respiratory syncytial virus. J Cellular Biochem Suppl. 15E. P.120, Abstract No. 108.

Kettleborough et al., 1994. Isolation of tumor cell-specific single-chain Fv from immunized mice using phage-antibody libraries and the re-construction of whole antibodies from these antibody fragments. Eur J Immunol. 24(4):952-8.

Kudo et al., 1992. New strategies to establish human monoclonal antibodies. Tohoku J Exp Med. 168(2):323-327.

Kudo et al., 1993. Production of a human monoclonal antibody to a synthetic peptide by active in vivo immunization using a SCID mouse grafted with human lymphocytes. Tohoku J Exp Med. 171: 327-338.

Langer and Peppas, 1983. Chemical and physical structure of polymers as carriers for controlled release of bioactive agents: a review. J Macromol Sci.—Rev Macromol Chem Phys.C23(1):61-126.

Langer, 1990. New methods of drug delivery. Science. 249:1527-1533.

Lee et al., 1998. Demonstration of IgM antibodies of high affinity within the anti-Galalphal-3Gal antibody repertoire. Transplantation. 66(8):1117-9.

Lonberg and Huszar, 1995. Human antibodies from transgenic mice. Int. Rev. Immunol. 13:65-96.

Love et al., 1993. How the anti-(metal chelate) antibody CHA255 is specific for the metal ion of its antigen: X-ray structures for two Fab'/hapten complexes with different metals in the chelate. Biochemistry. 32(41):10950-10959.

Maccallum et al., 1996. Antibody-antigen interactions: contact analysis and binding site topography. J Mol Biol. 262(5):732-45.

Malley et al., 1998. Reduction of Respiratory Syncytial Virus (RSV) in Tracheal Aspirates in Intubated Infants by Use of Humanized Monoclonal Antibody to RSV F Protein. J of Infect Dis. 178:1555-1561.

Marks et al., 1992. By-passing immunization: building high affinity human antibodies by chain shuffling. Biotechnology (NY) 10(7):779-83.

Maynard et al., 2002. Protection against anthrax toxin by recombinant antibody fragments correlates with antigen affinity. Nat Biotechnol. 20(6):597-601.

Mccall et al., 1999. Isolation and characterization of an anti-CD16 single-chain Fv fragment and construction of an anti-HER2/neu/anti-CD16 bispecific scFv that triggers CD16-dependent tumor cytolysis. Mol Immunol. May 1999;36(7):433-45.

MedImmune, Inc. Annual Report (2001) (in 2 pts.).

MedImmune, Inc's (MEDI) phase I Numax study shows potential to reduce RSV disease in upper airway of children. (Sep. 1, 2005) BioSpace Beat, Biospace.com (www.biospace.com/news_story.aspx?StoryID=21014020).

MedImmune, Inc.'s (MEDI) Release: Numax achieves primary endpoint in preliminary analysis of data from comparartive phase 3 trial with Synagis (Nov. 6, 2006) BioSpace Beat, Biospace.com (www.biospace.com/news_story.aspx?StoryID=36114&full=1).

MedImmune, Inc., 1999 Synagis® package insert, revised Dec. 2, 1999.

MedImmune, Inc., 2002 Synagis® package insert, last revised Oct. 23, 2002.

Mejias et al., 2005 "Respiratory syncytial virus infections: Old challenges and new opportunities," Ped. Infect. Dis. J. 24: S189-S197.

Mejias et al., 2005, "Comparative Effects of Two Neutralizing Anti-Respiratory Syncytial Virus (RSV) Monoclonal Antibodies in the RSV Murine Model: Time versus Potency," Antimicrobial Agents and Chemotherapy vol. 49, No. 11: 4700-4707.

[No author] "Motavizumab vs palivizumab for RSV infections in infants", (Nov. 11, 2006) Inpharma vol. 1 No. 1563, p. 5.

Mullinax et al., 1992. Expression of a heterodimeric Fab antibody protein in one cloning step. Bio Techniques. 12:864-869.

Myszka et al., 1997 "Kinetic analysis of a protein antigen-antibody interaction limited by mass transport on an optical biosensor," Biophys Chem. 64(1-3):127-37.

Nguyen et al., 2000 "Efficient generation of respiratory syncytial virus (RSV)-neutralizing human MoAbs via human peripheral blood lymphocyte (hu-PBL)-SCID mice and scFv phage display libraries," Clin. Exp. Immunol. 122:85-93.

O'Byrne and Postma, 1999. The Many Faces of Airway Inflammation. Am J Respir Crit Care Med. 159(5 Pt 2): S41-63.

Orkin and Motulsky, 1995 "Report and recommendations of the panel to assess the NIH investment in research on gene therapy," available from http://www.nih.gov/news/panelrep.html.

Padlan, 1991. A possible procedure for reducing the immunogenicity of antibody variable domains while preserving their ligand-binding properties. Mol. Immunol. 28(4/5):489-498.

Palomo et al., 1990 "Induction of a Neutralizing Immune Response to Human Respiratory Syncytial Virus with Anti-Idiotypic Antibodies," J. Virology 64(9): 4199-4206.

Persic et al., 1997. An integrated vector system for the eukaryotic expression of antibodies or their fragments after selection from phage display libraries. Gene. 187(1):9-18.

Prince et al., 1987, Effectiveness of Topically Administered Neutralizing Antibodies inExperimental Immunotherapy of Respiratory Syncytial Virus Infection in Cotton Rats, J Virol; 61(6):1851-1854.

Prince, 2001, "An update on respiratory syncytial virus antiviral agents." Expert Opin Investig Drugs. 10(2):297-308.

Riechmann et al., 1988. Reshaping human antibodies for therapy. Nature. 332(6162):323-7.

Roguska et al., 1994, "Humanization of murine monoclonal antibodies through variable domain resurfacing," Proc. Natl. Acad. Sci. U.S.A. 91(3):969-973.

Ruther and Muller-Hill, 1983. Easy identification of cDNA clones. EMBO J. 2:1791-1794.

Sakurai et al., 1999, "Human antibody responses to mature and immature forms of viral envelope in respiratory syncytial virus infection: significance for subunit vaccines." J Virol. 73(4):2956-2962.

Schier et al., 1996, "Isolation of picomolar affinity anti-c-erbB-2 single-chain Fv by molecular evolution of the complementarity determining regions in the center of the antibody binding site," J. Mol. Biol. 263(4):551-567.

Seaver, 1994. Monoclonal antibodies in industry: More difficult than originally thought; Genetic Engineering News, vol. 14, No. 14, p. 10 and 21.

Sevier et al., 1981. Monoclonal antibodies in clinical immunology. Clin Chem. 27(11):1797-806.

Shreder, 2000. Synthetic haptens as probes of antibody response and immunorecognition; Methods; 20(3):372-9.

Stott et al., 1984. The characterization and uses of monoclonal antibodies to respiratory syncytial virus. Dev Biol Stand. 57:237-44.

Studnicka et al., 1994. Human-engineered monoclonal antibodies retain full specific binding activity by preserving non-CDR complementarity-modulating residues. Protein Eng. 7:805-814.

Takahashi et al. 1984. Rearranged immunoglobulin heavy chain variable region (VH) pseudogene that deletes the second complementarity-determining region. PNAS 81: 5194-198.

Taylor et al., 1984. Monoclonal antibodies protect against respiratory syncytial virus infection in mice. Immunology. 52(1):137-42.

Taylor et al., 1992. Protective epitopes on the fusion protein of respiratory syncytial virus recognized by murine and bovine monoclonal antibodies. J Gen Virol. 73 ( Pt 9):2217-23.

Thompson et al., 1996, "Affinity maturation of a high-affinity human monoclonal antibody against the third hypervariable loop of human immunodeficiency virus: use of phage display to improve affinity and broaden strain reactivity," J. Mol. Biol. 256(1):77-88.

Vancott et al., 1994, "Dissociation rate of antibody-gp120 binding interactions is predictive of V3-mediated neutralization of HIV-1," J. Immunol. 153(1):449-59.

Verma et al., 1997, "Gene therapy—promises, problems and prospects," Nature 389:239-242.

Walsh et al., 1984. Protection from respiratory syncytial virus infection in cotton rats by passive transfer of monoclonal antibodies. Infect Immun. 43(2):756-8.

Ware et al., 1985. Human, rat or mouse hybridomas secrete high levels of monoclonal antibodies following transplantation into mice with severe combined immunodeficiency disease (SCID). J Immunol Methods. 85(2):353-61.

Watkins et al., 1997. Determination of the relative affinities of antibody fragments expressed in *Escherichia coli* by enzyme-linked immunosorbent assay. Anal Biochem. 253(1):37-45.

Weltzin et al., 1989. Binding and transepithelial transport of immunoglobulins by intestinal M cells: demonstration using monoclonal IgA antibodies against enteric viral proteins. J. Cell Biol. 108(5):1673-85.

Weltzin et al., 1994, "Intranasal Monoclonal Immunoglobulin A against Respiratory Syncytial Virus Protects against Upper and Lower Respiratory Tract Infections in Mice." Antimicro Agents & Chemo. 38(12):2785-2791.

Weltzin et al., 1996, "Intranasal Monoclonal IgA Antibody to Respiratory Syncytial Virus Protects Rhesus Monkeys against Upper and Lower Tract Infection." J. of Infect Dis. 174: 256-261.

Whitlow et al., 1995, "1.85 A structure of anti-fluorescein 4-4-20 Fab." Protein Eng. 8(8):749-761.

Wilson et al., 1984. The structure of an antigenic determinant in a protein. Cell. 37(3):767-78.

Wu et al. 1999, "Humanization of murine monoclonal antibody by simultaneous optimization of framework and CDR residues," J. Mol. Biol. 294(1): 151-62.

Wu et al., 2002, "Tailoring Kinetics of Antibodies Using Focused Combinatorial Libraries" chapter 13 from Methods in Molecular Biology vol. 207, Eds. Welschop and Krauss, Humana Press Inc., Totowa, NJ, pp. 213-233.

Wu et al., 2005, "Ultra-potent Antibodies Against Respiratory Syncytial Virus: Effects of Binding Kinetics and binding Valence on Viral Neutralization," J. Mol. Biol. 350: 126-144.

Wu et al., 2007, "Development of Motavizumab, an Ultra-potent Antibody for the Prevention of Respiratory Syncytial Virus Infection in the Upper and Lower Respiratory Trace" J. Mol. Biol. 368(3): 652-65.

Wu et al., 2008, Immunoprophylaxis of RSV Infection: Advancing from RSV-IGIV to Palivizumab and Motavizumab, Curr Topics Microbiol Immunol; 317:103-123.

Yang et al., 1995, "CDR walking mutagenesis for the affinity maturation of a potent human anit-HIV-1 antibody into the picomolar range," J. Mol. Biol. 254:392-403.

Colman, 1994. Effects of amino acid sequence changes on antibody-antigen interactions. Res Immunol. 145(1):33-6.

Scott et al., 1985. Cellular reactivity to respiratory syncytial virus in human colostrum and breast milk. J Med Virol. 17(1):83-93.

Watkins et al., 1998. Discovery of human antibodies to cell surface antigens by capture lift screening of phage-expressed antibody libraries. Anal Biochem. 256(2):169-77.

U.S. Appl. No. 09/724,396, filed Nov. 28, 2000, Young et al.

U.S. Appl. No. 60/388,921, Oliver et al.

Abman et al., 1988, "Role of respiratory syncytial virus in early hospitalizations for respiratory distress of young infants with cystic fibrosis," J. Pediatr. 113(5):826-830.

Ahouse et al., 1993, "Mouse MHC class 1-like Fc receptor encoded outside the MHC," *J. Immunol.*151(11):6076-6088.

American Academy of Pediatrics Committee on Infectious Diseases, 1993, "Use of ribavirin in the treatment of repiratory syncytial virus infection," Pediatrics 92(3):501-504.

American Academy of Pediatrics, 2000, "Summaries of Infectious Diseases," in: 2000 *Red Book: Report of the Committee on Infectious Diseases*, 25*th* ed., Pickering, ed., Elk Grove Village, IL pp. 483-487.

Anderson et al., 1985, "Microneutralization test for respiratory syncytial virus based on an enzyme immunoassay," J. Clin. Microbiol. 22:1050-1052.

Beeler et al., 1989, "Neutralization epitopes of the F glycoprotein of respiratory syncytial virus: effect of mutation upon fusion function," J. Virol. 63(7):2941-2950.

Bentley et al., 1980, "Human immunoglobulin variable region genes—DNA sequences of two V kappa genes and a pseudogene," Nature 288(5792):730-733.

Borvak et al., 1998, "Functional expression of the MHC class I-related receptor, FcRn, in endothelial cells of mice," Int. Immunol. 10(9):1289-1298.

Botts et al., 1984, "On the mechanism of energy transduction in myosin subfragment 1," Proc. Natl. Acad. Sci. USA 81(7):2060-2064.

Boulianne et al., 1984, "Production of functional chimaeric mouse/human antibody," Nature 312(5995):643-646.

Burmeister et al., 1994, "Crystal structure at 2.2 A resolution of the MHC-related neonatal Fc receptor," Nature 372(6504):336-343.

Burmeister et al., 1994, "Crystal structure of the complex of rat neonatal Fc receptor with Fc," Nature 372(6504):379-383.

Byrd et al., 1997, "Animal models of respiratory syncytial virus infection," Clin. Infect. Dis. 25(6):1363-1368.

Carson et al., 1986, "Human lymphocyte hybridomas and monoclonal antibodies," Adv. Immunol. 38:275-311.

Chintalacharuvu et al., 2001, "Hybrid IgA2/IgG1 antibodies with tailor-made effector functions," Clin. Immunol. 101(1):21-31.

Cianga et al., 1999, "Identification and function of neonatal Fc receptor in mammary gland of lactating mice." Eur. J. Immunol. 29(8):2515-2523.

Cleek et al., 1997, "Biodegradable Polymeric Carriers for a bFGF Antibody for Cardiovascular Application," Pro. Int'l Symp. Control. Rel Bioact. Mater. 24:853-854.

Cleland et al., 1993, "The development of stable protein formulations: a close look at protein aggregation, deamidation, and oxidation," Crit. Rev. Ther. Drug Carrier Syst. 10(4):307-377.

Conrad et al., 1987, "Aerosolized ribavirin treatment of respiratory syncytial virus infection in infants hospitalized during an epidemic," Pediatr. Infect. Dis. J. 6(2):152-158.

Cruse et al., 1995, Illustrated Dictionary of Immunology, Boca Raton: CRC Press, pp. 18-19.

Cull et al., 1992, "Screening for receptor ligands using large libraries of peptides linked to the C terminus of the lac repressor," Proc. Natl. Acad. Sci. USA 89(5):1865-1869.

Cunningham, 1991, "Rehospitalization for respiratory illness in infants of less than 32 weeks' gestation," Pediatrics 88(3):527-532.

Cwirla et al., 1990, "Peptides on phage: a vast library of peptides for identifying ligands," Proc. Natl. Acad. Sci. USA 87(16):6378-6382.

Dickinson et al., 1999, "Bidirectional FcRn-dependent IgG transport in a polarized human intestinal epithelial cell line," J. Clin Invest. 104(7):903-911.

Dorland's Illustrated Medical Dictionary, 1994, 28*th* ed., Philadelphia: WB Saunders p. 874.

Duenas et al., 1996, "In vitro immunization of naive human B cells yields high affinity immunoglobulin G antibodies as illustrated by phage display," Immunology 89(1):1-7.

Duenas et al., 1996, "Selection of phage displayed antibodies based on kinetic constants," Mol. lmmunol. 33(3):279-285.

Evans et al., eds., 1989, Viral Infections of Humans: Epidemiology and Control, 3*rd* ed., Plenum Medical Book, New York, pp. 525-544.

Everitt et al., 1996, "The pharmacokinetics, antigenicity, and fusion-inhibition activity of RSHZ19, a humanized monoclonal antibody to respiratory syncytial virus, in healthy volunteers," J. Infect. Dis. 174(3):463-469.

Falsey, 1991, "Noninfluenza respiratory virus infection in long-term care facilities," Infect. Control Hosp. Epidemiol. 12(10):602-608.

Feigen et al., eds., 1987, Textbook of Pediatric Infectious Diseases, WB Saunders, Philadelphia, pp. 1653-1675.

Felici, 1991, "Selection of antibody ligands from a large library of oligopeptides expressed on a multivalent exposition vector," J. Mol. Biol. 222(2):301-310.

Fernandez, et al., 1980, "Preparation of a Stable Intravenous Gamma-Globulin: Process Design and Scale Up," Vox. Sang. 39:101-112.

Fields et al., 1996, "Crystal Structure of the Vα domain of a T cell antigen receptor," Immunotechnology 2(4):270.

Fields et al., eds., 1990, Fields Virology 2$^{nd}$ ed., vol. 1, Raven Press, New York, pp. 1045-1072.

Firan et al., 2001, "The MHC class 1-related receptor, FcRn, plays an essential role in the maternofetal transfer of gamma-globulin in humans," Int. Immunol. 13(8):993-1002.

Fodor, 1993, "Multiplexed biochemical assays with biological chips," Nature 364(6437):555-556.

Foote et al., 1991, "Kinetic maturation of an immune response," Nature 352(6335):530-532.

Foote et al., 1995, "Kinetic and affinity limits on antibodies produced during immune response," Proc. Nat'l Acad. Science USA 92:1254-1256.

Garvie et al., 1980, "Outbreak of Respiratory Syncytial Virus Infection in the Elderly," Br. Med. J. 281(6250):1253-1254.

Ghetie et al., 1996, "Abnormally short serum half-lives of IgG in beta 2-microglobulin-deficient mice," Eur. J. Immunol. 26(3):690-696.

Ghetie et al., 1997, "Increasing the serum persistence of an IgG fragment by random mutagenesis," Nat. Biotechnol. 15(7):637-640.

Ghetie et al., 2000, "Multiple roles for the major histocompatibility complex Class 1-related receptor FcRn," Ann. Rev. Immunol. 18:739-766.

Glaser et al., 1992, "Antibody engineering by codon-based mutagenesis in a filamentous phage vector system," J. Immunol. 149:3903-3913.

Glezen et al., 1981, "Risk of Respiratory Syncytial Virus Infection for Infants From Low-Income Families in Relationship to Age, Sex, Ethnic Group, and Maternal Antibody Level," J. Pediatr. 98(5):708-715.

Greenspan et al., 1999, "Defining epitopes: It's not as easy as it seems," Nat. Biotechnol. 17(10):936-937.

Gronski, et al., 1988, "On the Nature of IgG dimers. I. Dimers in Human Polyclonal IgG Preparations, kinetic studies," Behring Inst. Mitt. 82:127-143.

Groothuis et al., 1988, "Respiratory Syncytial Virus Infection in Children with Bronchopulmonary Dysplasia," Pediatrics 82(2):199-203.

Groothuis et al., 1993, "Prophylactic Administration of Respiratory Syncytial Virus Immune Globulin to High-risk Infants and Young Children," The Respiratory Syncytial Virus Immune Globulin Study Group, N. Engl. J. Med. 329(21):1524-1530.

Groves et al., 1987, "Production of an ovine monoclonal antibody to testosterone by an interspecies fusion," Hybridoma 6(1):71-76.

Hacking et al., 2002, "Respiratory syncytial virus—viral biology and the host response," J. Infection 45:18-24.

Hall et al., 1975, "Nosocomial respiratory syncytial virus infections," N. Engl. J. Med. 293(26):1343-1346.

Hall et al., 1979, "Neonatal Respiratory Syncytial Virus Infection," N. Engl. J. Med. 300(8):393-396.

Hall et al., 1983, "Aerosolized ribavirin treatment of infants with respiratory syncytial viral infection. A randomized double-blind study," N. Engl. J. Med. 308(24):1443-1447.

Hall et al., 1985, "Ribavirin treatment of respiratory syncytial viral infection in infants with underlying cardiopulmonary disease," JAMA 254(21):3047-3051.

Hall et al., eds., 1995, Principles and Practice of Infectious Diseases 4$^{th}$ ed., Churchill Livingstone, New York, pp. 1501-1519.

Hall, 1993, "Respiratory Syncytial: What We Know Now," Contemp. Pediatrics 10:92-110.

Haynes et al., 2002, "Neutralizing anti-F glycoprotein and anti-substance P antibody treatment effectively reduces infection and inflammation associated with respiratory syncytial virus infection," J. Virol. 76(14):6873-6881.

Heard et al., 1999, "Two neutralizing human RSV antibodies: cloning, expression, and characterization," Mol. Med. 5:35-45.

Hemming et al., 1985, "Studies of Passive Immunotherapy for Infections of Respiratory Syncytial Virus in the Respiratory Tract of a Primate Model," J. Infect. Dis. 152(5):1083-1087.

Henderson et al., 1979, "Respiratory-Syncytial-Virus Infections, Reinfections and Immunity. A Prospective, Longitudinal Study in Young Children," N. Engl. J. Med. 300(10):530-534.

Hertz et al., 1989, "Respiratory Syncytial Virus-Induced Acute Lung Injury in Adult Patients With Bone Marrow Transplants: a Clinical Approach and Review of the Literature," Medicine (Baltimore) 68(5):269-281.

Ho et al., 1989, "Site-directed mutagenesis by overlap extension using the polymerase chain reaction," Gene 77(1):51-59.

Houghten, 1992, "The use of synthetic peptide combinatorial libraries for the identification of bioactive peptides," Biotechniques 13(3):412-421.

Howard et al., 1989, "Intracerebral Drug Delivery in Rats with Lesion-Induced Memory Deficits," J. Neurosurg. 71(1):105-112.

Israel et al., 1996, "Increased clearance of IgG in mice that lack beta 2-microglobulin: possible protective role of FcRn," Immunology 89(4):573-578.

Johnson et al., 1987, "The G Glycoprotein of Human Respiratory Syncytial Viruses of Subgroups A and B: Extensive Sequence Divergence Between Antigenically Related Proteins," Proc. Natl. Acad. Sci. USA 84(16):5625-5629.

Johnson et al., 1997, "Development of a Humanized Monoclonal Antibody (MEDI-493) With Potent In Vitro and In Vivo Activity Against Respiratory Syncytial Virus," J. Infect. Dis. 176(5):1215-1224.

Johnson et al., 1999, "A direct comparison of the activities of two humanized respiratory syncytial virus monoclonal antibodies: MEDI-493 and RSHZ19," J. Infect. Dis. 180(1):35-40.

Junghans et al., 1996, "The protection receptor for IgG catabolism is the beta2-microglobulin-containing neonatal intestinal transport receptor," Proc. Natl. Acad. Sci. USA 93(11):5512-5516.

Junghans, 1997, "Finally! The Brambell receptor (FcRB). Mediator of transmission of immunity and protection from catabolism for IgG," Immunol. Res. 16(1):29-57.

Junghans, 1997, "IgG biosynthesis: no 'immunoregulatory feedback,'" Blood 90(10):3815-3818.

Junghans, 1997, "Next-generation Fc chimeric proteins: avoiding immune-system interactions," Trends Biotechnol. 15(5):155.

Kabat et al., 1991, "Sequences of proteins of immunological interest," U.S. Public Health Service, National Institutes of Health (table of contents only).

Kapikian et al., 1969, "An Epidemiologic Study of Altered Clinical Reactivity to Respiratory Syncytial (RS) Virus Infection in Children Previously Vaccinated With an Inactivated RS Virus Vaccine," Am. J. Epidemiol. 89(4):405-421.

Karlsson et al., 1997, "Experimental design for kinetic analysis of protein-protein interactions with surface plasmon resonance biosensors," J. Immunol. Methods. 200(1-2):121-133.

Kim et al., 1969, "Respiratory Syncytial Virus Disease in Infants Despite Prior Administration of Antigenic Inactivated Vaccine," Am. J. Epidemiol. 89(4):422-434.

Kim et al., 1994, "Catabolism of the murine IgG1 molecule: evidence that both CH2-CH3 domain interfaces are required for persistence of IgG1 in the circulation of mice," Scand. J. Immunol. 40(4):457-465.

Kim et al., 1994, "Identifying amino acid residues that influence plasma clearance of murine IgG1 fragments by site-directed mutagenesis," Eur. J. Immunol. 24(3):542-548.

Kim et al., 1994, "Localization of the site of the murine IgG1 molecule that is involved in binding to the murine intestinal Fc receptor," Eur. J. Immunol. 24(10):2429-2434.

Kim et al., 1994, "Mapping the site that controls the catabolism of the murine IgG1 molecule by site-directed mutagenesis," FASEB J. Abstracts Part 1, 8(4):A467 Abstract 2705.

Kim et al., 1995, "Evidence that the hinge region plays a role in maintaining serum levels of the murine IgG1 molecule," Mol. Immunol. 32(7):467-475.

Kim et al., 1995, 9$^{th}$ International Congress of Immunol. p. 469.

Knappik et al., 2000, "Fully synthetic human combinatorial antibody libraries (HuCAL) based on modular consensus frameworks and CDRs randomized with trinucleotides," J. Mol. Biol. 296(1):57-86.

Kristoffersen et al., 1996, "Co-localization of the neonatal Fc gamma receptor and IgG in human placental term syncytiotrophoblasts," Eur. J. Immunol. 26(7):1668-1671.

Kunkel et al., 1987, "Rapid and efficient site-specific mutagenesis without phenotypic selection," Methods Enzymol. 154:367-382.

Lam et al., 1997, "Microencapsulation of recombinant humanized monoclonal antibody for local delivery," Proc. Int'l. Symp. Control Rel. Bioact. Mater. 24:759-760.

Lam, 1991, "A new type of synthetic peptide library for identifying ligand-binding activity," Nature 354(6348):82-84.

Lamprecht et al., 1976, "Role of Maternal Antibody in Pneumonia and Bronchiolitis Due to Respiratory Syncytial Virus," J. Infect. Dis. 134(3):211-217.

Landry et al., "Evaluation of reconstituted lyophilized palivizumab given intravenously at 15 and 30 mg/kg," Poster Session, Tuesday, Infect. Dis. 166A:969.

Levy et al., 1985, "Inhibition of Calcification of Bioprosthetic Heart Valves by Local Controlled-release Diphosphonate," Science 228(4696):190-192.

Li et al., 1997, "Dual conformations of a T cell receptor V alpha homodimer: implications for variability in V alpha V beta domain association," J. Mol. Biol. 269(3):385-394.

Liu et al., 1987, "Expression of mouse:human immunoglobulin heavy-chain cDNA in lymphoid cells," Gene 54(1):33-40.

Lobuglio et al., 1989, "Mouse/human chimeric monoclonal antibody in man: kinetics and immune response," Proc. Natl. Acad. Sci. USA 86(11):4220-4224.

Macdonald et al., 1982, "Respiratory Syncytial Viral Infection in Infants With Congenital Heart Disease," N. Engl. J. Med. 307(7):397-400.

Martin et al., 1999, "Characterization of the 2:1 complex between the Class I MHC-related Fc receptor and its Fc ligand in solution," Biochemistry 38(39):12639-12647.

Mcarthur-Vaughan et al., 2002, "A rhesus monkey model of respiratory syncytial virus infection," J. Med. Primatol. 31(2):61-73.

Medesan et al., 1996, "Localization of the site of the IgG molecule that regulates maternofetal transmission in mice," Eur. J. Immunol. 26(10):2533-2536.

Medesan et al., 1997, "Delineation of the amino acid residues involved in transcytosis and catabolism of mouse IgG1," J. Immunol. 158(5):2211-2217.

Medesan et al., 1998, "Comparative studies of rat IgG to further delineate the Fc:FcRn interaction site," Eur. J. Immunol. 28(7):2092-2100.

Meissner et al., "Safety and Pharmacokinetics of an Intramuscular Monoclonal Antibody (SB 209763) Against Respiratory Syntytial Virus (RSV) in Infants and Young Childen at Risk for Severe RSV Disease", Antimicrob Agents Chemother 43:1183-1188 (1999).

Morrell et al., eds., 1986, Clinical Use of Intravenous Immunoglobulins, Academic Press, London, pp. 285-294.

Morrison et al., 1984, "Chimeric human antibody molecules: mouse antigen-binding domains with human constant region domains," Proc. Natl. Acad. Sci. USA 81(21):6851-6855.

Morrison et al., 1985, "Transfectomas provide novel chimeric antibodies," Science 229(4719):1202-1207.

Murphy and Hall, 1994, "An Update on Approaches to the Development of Respiratory Syncytial Virus (RSV) and Parainfluenza Virus Type 3 (PIV3) Vaccines," Virus Res. 32(1):13-36.

Murphy et al., 1988, "Passive Transfer of Respiratory Syncytial Virus (RSV) Antiserum Suppresses the Immune Response to the RSV Fusion (F) and Large (G) Glycoproteins Expressed by Recombinant Vaccinia Viruses," J. Virol. 62(10):3907-3910.

Murphy et al., 1991, "Effect of Passive Antibody on the Immune Response of Cotton Rats to Purified F and G HG Glycoproteins of Respiratory Syncytial Virus (RSV)," Vaccine 9(3):185-189.

Myszka et al., 1999, "Survey of the 1998 optical biosensor literature," J. Mol. Recognit. 12(6):390-408.

Navas et al., 1992, "Improved Outcome of Respiratory Syncytial Virus Infection in a High-Risk Hospitalized Population of Canadian children. Pediatric Investigators Collaborative Network on Infections in Canada," J. Pediatr. 121(3):348-354.

New Vaccine Development, 1985, Establishing Priorities vol. 1, National Academy Press, Washington DC pp. 397-409.

Newman et al., 1992, "'Primitization' of recombinant antibodies for immunotherapy of human diseases: A Macaque/Hunab chimeric antibody against human CD4," Biotechnology 10(11):1455-1460.

Ning et al., 1996, "Intratumoral Radioimmunotherapy of a Human Colon Cancer Xenograft Using a Sustained Release Gel," Radiotherapy and Oncology 39:179-189.

Ogra et al., 1988, "Respiratory Syncytial Virus Infection and the Immunocompromised Host," Pediatr. Infect. Dis. J. 7(4):246-249.

Paul, ed., 1989, Fundamental Immunology, 2$^{nd}$ ed., Raven Press, New York pp. 332-336.

Physician's Desk Reference, 2001, 55$^{th}$ ed. p. 1863-1864.

Physician's Desk Reference, 2002, 56$^{th}$ ed. p. 2028-2029.

Piedimonte et al., 1999, "Respiratory syncytial virus upregulates expression of the substance P receptor in rat lungs," Am. J. Physiol. 277(4 Pt 1):L831-L840.

Pohl et al., 1992, "Respiratory Syncytial Virus Infections in Pediatric Liver Transplant Recipients," J. Infect. Dis. 165(1):166-169.

Popov et al., 1996, "A novel and efficient route for the isolation of antibodies that recognize T cell receptor V alpha(s)," Mol. Immunol. 33(6):493-502.

Popov et al., 1996, "The stoichiometry and affinity of the interaction of murine Fc fragments with the MHC class I-related receptor, FcRn," Mol. Immunol. 33(6):521-530.

Press et al., 1970, "The Amino Acid Sequences of the Fd Fragments of Two Human Gamma-1 Heavy chains," Biochem. J. 117(4):641-660.

Prince et al., "Treatment of Respiratory Syncytial Virus Bronchiolitis and Pneumonia in a Cotton Rat Model with Systematically Administered Monoclonal Antibody (Palivizumab) and Glucocorticosteroid," J Inf Diseases 182:1327-1330 (2000).

Prince et al., 1983, "Mechanisms of Immunity to Respiratory Syncytial Virus in Cotton Rats," Infect Immun. 42(1):81-87.

Prince et al., 1985, "Immunoprophylaxis and Immunotherapy of Respiratory Syncytial Virus Infection in the Cotton rat," Virus Res. 3(3):193-206.

Prince et al., 1985, "Quantitative Aspects of Passive Immunity to Respiratory Syncytial Virus Infection in Infant Cotton Rats," J. Virol. 55(3):517-520.

Prince et al., 1990, "Mechanism of antibody-mediated viral clearance in immunotherapy of respiratory syncytial virus infection of cotton rats," J. Virol. 64(6):3091-3092.

Prince et al., 1996, "Treatment of parainfluenza virus type 3 bronchiolitis and pneumonia in a cotton rat model using topical antibody and glucocorticosteroid," J. Infect. Dis. 173(3):598-608.

Prince, 1975, Ph.D. Dissertation, UCLA.

Raghavan et al., 1994, "Investigation of the interaction between the Class 1 MHC-related Fc receptor and its immunoglobulin G ligand," Immunity 1(4):303-315.

Raghavan et al., 1995, "Analysis of the pH dependence of the neonatal Fc receptor/immunoglobulin G interaction using antibody and receptor variants," Biochemistry 34(45):14649-14657.

Raman et al., 1992, "Diffusion-limited rates for monoclonal antibody binding to cytochrome c," Biochemistry 31(42):10370-10379.

Rodewald, 1976, "pH-dependent binding of immunoglobulins to intestinal cells of the neonatal rat," J. Cell. Biol. 71(2):666-669.

Roost et al., 1995, "Early high-affinity neutralizing anti-viral IgG responses without further overall improvements of affinity," PNAS USA 92:1257-1261.

Rosok et al., 1995, "A combinatorial library strategy for the rapid humanization of anticarcinoma BR 96 Fab," JBC 271(27):22611-22618.

Rudikoff et al., 1982, "Single amino acid substitution altering antigen-binding specificity," Proc. Natl. Acad. Sci. USA 79(6):1979-1983.

Ruuskanen et al., 1993, "Respiratory syncytial virus," Curr. Probl. Pediatr. 23(2):50-79.

Saez-Llorens et al., 1997, "Phase I/II open label multi dose escalation trial of a humanized respiratory synctial virus (RSV) monoclonal antibody (Medi-493) administered intramuscularly (IM) in high risk children," Abstracts in Non HIV Virology, ICAAC Toronto.

Saez-Llorens et al., 1998, "Safety and Pharmacokinetics of an Intramuscular Humanized Monoclonal Antibody to Respiratory Synctial Virus in Premature Infants and Infants with Bronchopulmonary Dysplasia," Pediatric Infect. Dis. J. 17:787-791.
Sahagan et al., 1986, "A genetically engineered murine/human chimeric antibody retains specificity for human tumor-associated antigen," J. Immunol. 137(3):1066-1074.
Sanchez et al., 1999, "Stoichiometry of the interaction between the major histocompatibility complex-related Fc receptor and its Fc ligand," Biochemistry 38(29):9471-9476.
Sanger et al., 1977, "DNA sequencing with chain-terminating inhibitors," Proc. Natl. Acad. Sci. USA 74(12):5463-5467.
Saudek et al., 1989, "A preliminary trial of the programmable implantable medication system for insulin delivery." N. Engl. J. Med. 321(9):574-579.
Schuck et al., 1999, "Sedimentation equilibrium analysis of recombinant mouse FcRn with murine IgG1," Mol. Immunol. 36(15-16):1117-1125.
Scott et al., 1990, "Searching for peptide ligands with an epitope library," Science 249(4967):386-390.
Sefton, 1987, "Implantable Pumps," CRC Crit. Ref Biomed. Eng. 14:20.
Simister et al., 1989, "An Fc receptor structurally related to MHC Class I antigens," Nature 337(6203):184-187.
Smith et al., 1991, "A Controlled Trial of Aerosolized Ribavirin in Infants Receiving Mechanical Ventilation for Severe Respiratory Syncytial Virus Infection," N. Engl. J. Med. 325(1):24-29.
Song et al., 1995, "Antibody Mediated Lung Targeting of Long-Circulating Emulsions," PDA Journal of Pharmaceutical Science & Technology 50:372-397.
Sorbera et al., 1998, "Palivizumab," Drugs Data Report 20:702-703.
Sorbera et al., 1998, "Palivizumab," Drugs of the Future 23:970-976.
Steplewski et al., 1988, "Biological activity of human-mouse IgG1, IgG2, IgG3, and IgG4 chimeric monoclonal antibodies with antitumor specificity," Proc. Natl. Acad. Sci. USA 85(13):4852-4856.
Story et al., 1994, "A major histocompatibility complex class I-like Fc receptor cloned from human placenta: possible role in transfer of immunoglobulin G from mother to fetus," J. Exp. Med. 180(6):2377-2381.
Subramanian et al., 1997, "Randomized double blind placebo controlled dose escalation trial of a humanized respiratory syncytial virus monoclonal antibody in high risk infants," Poster session Infect. Dis. 130A:768.
Subramanian et al., 1998, "Safety, tolerance and pharmacokinetics of a humanized monoclonal antibody to respiratory syncytial virus in premature infants and infants with bronchopulmonary dysplasia. MEDI-493 Study Group," Pediatr. Infect. Dis. J. 17(2):110-115.
Sun et al., 1987, "Chimeric antibody with human constant regions and mouse variable regions directed against carcinoma-associated antigen 17-1A," Proc. Natl. Acad. Sci. USA 84(1):214-218.
Takeda et al., 1985, "Construction of chimaeric processed immunoglobulin genes containing mouse variable and human constant region sequences," Nature 314(6010):452-454.
Talwar et al., 1976, "Isoimmunization against human chorionic gonadotropin with conjugates of processed beta-subunit of the hormone and tetanus toxoid," Proc. Natl. Acad. Sci. USA 73(1):218-222.
Thatte et al., 1999, "Molecular requirements for T cell recognition by a major histocompatibility complex class II-restricted T cell receptor: the involvement of the fourth hypervariable loop of the V alpha domain," J. Exp. Med. 189(3):509-520.
van der Merwe et al., 1993, "Affinity and kinetic analysis of the interaction of the cell adhesion molecules rat CD2 and CD48," EMBO J. 12(13):4945-4954.
van der Merwe et al., 1994, "Human cell-adhesion molecule CD2 binds CD58 (LFA-3) with a very low affinity and an extremely fast dissociation rate but does not bind CD48 or CD59," Biochemistry 33(33):10149-10160.
van Wyke et al., 1985, "Antigenic variation in the hemagglutinin-neuraminidase protein of human parainfluenza type 3 virus," Virology 143(2):569-582.
Vaughn et al., 1997, "High-affinity binding of the neonatal Fc receptor to its IgG ligand requires receptor immobilization," Biochemistry 36(31):9374-9380.
Vaughn et al., 1997, "Identification of critical IgG binding epitopes on the neonatal Fc receptor," J. Mol. Biol. 274(4):597-607.
Wald et al., 1988, "In re ribavirin: a case of premature adjudication?" J. Pediatr. 112(1):154-158.
Wallace et al., 1980, "Studies on the immunoglobulin-G Fc-fragment receptor from neonatal rat small intestine," Biochem. J. 188(1):9-16.
Walsh et al., 1987, "Immunization with Glycoprotein Subunits of Respiratory Syncytial Virus to Protect Cotton Rats Against Viral Infection," J. Infect. Dis. 155(6):1198-1204.
Wang et al., 1988, "Parenteral Formulations of Proteins and Peptides: Stability and Stabilizers," J. Parenteral Science & Technology 42(Supp):S3-S26.
Wang Wei, "Instability, stabilization, and formulation of liquid protein pharmaceuticals," *Int. J. Pharmaceutics* 185:129-188 (Aug. 20, 1999).
Ward et al., 1995, "The effector functions of immunoglobulins: implications for therapy," Ther. Immunol. 2(2):77-94.
Ward et al., 1997, "Biophysical and structural studies of TCRs and ligands: implications for T cell signaling," Curr. Opin Immunol. 9(1):97-106.
West et al., 2000, "Crystal structure and immunoglobulin G binding properties of the human major histocompatibility complex-related Fc receptor," Biochemistry 39(32):9698-9708.
Wright et al., 1982, "Administration of a highly attenuated, live respiratory syncytial virus vaccine to adults and children," Infect. Immun. 37(1):397-400.
Wu et al., 1998, "Stepwise in vitro affinity maturation of Vitaxin, an $\alpha v \beta 3$-specific humanized mAb," PNAS 95:6037-6042.
U.S. Appl. No. 60/178,426, filed Jan. 27, 2000, Young et al.
U.S. Appl. No. 60/186,252, filed Mar. 1, 2000, Young et al.
U.S. Appl. No. 12/476,183, filed Jun. 1, 2009, Young et al.
U.S. Appl. No. 09/724,396—Office Action dated Mar. 26, 2002.
U.S. Appl. No. 09/724,396—Office Action dated Dec. 3, 2002.
U.S. Appl. No. 09/724,396—Office Action dated Jun. 3, 2003.
U.S. Appl. No. 09/724,396—Office Action dated Jul. 28, 2003.
U.S. Appl. No. 09/724,396—Office Action dated Apr. 5, 2004.
U.S. Appl. No. 09/724,531 (U.S. Patent No. 7,229,619)—Office Action dated Feb. 21, 2003.
U.S. Appl. No. 09/724,531 (U.S. Patent No. 7,229,619)—Office Action dated Oct. 21, 2003.
U.S. Appl. No. 09/724,531 (U.S. Patent No. 7,229,619)—Office Action dated Jun. 4, 2004.
U.S. Appl. No. 09/724,531 (U.S. Patent No. 7,229,619)—Office Action dated Feb. 9, 2005.
U.S. Appl. No. 09/724,531 (U.S. Patent No. 7,229,619)—Office Action dated Jun. 15, 2005.
U.S. Appl. No. 09/724,531 (U.S. Patent No. 7,229,619)—Office Action dated Apr. 4, 2006.
U.S. Appl. No. 09/724,531 (U.S. Patent No. 7,229,619)—Office Action dated Aug. 22, 2006.
U.S. Appl. No. 09/724,531 (U.S. Patent No. 7,229,619)—Office Action / Notice of Allowability dated Jan. 30, 2007.
U.S. Appl. No. 09/996,288 (U.S. Patent No. 6,818,216)—Office Action dated Jul. 14, 2003.
U.S. Appl. No. 09/996,288 (U.S. Patent No. 6,818,216)—Office Action dated Jan. 29, 2004.
U.S. Appl. No. 09/996,288 (U.S. Patent No. 6,818,216)—Office Action / Notice of Allowability dated Jun. 30, 2004.
U.S. Appl. No. 09/996,265 (U.S. Patent No. 6,855,493)—Office Action dated Aug. 12, 2003.
U.S. Appl. No. 09/996,265 (U.S. Patent No. 6,855,493)—Office Action / Notice of Allowability dated Mar. 31, 2004.
U.S. Appl. No. 09/996,265 (U.S. Patent No. 6,855,493)—Office Action / Supplemental Notice of Allowability dated Jul. 13, 2004.
U.S. Appl. No. 10/403,180 (U.S. Patent No. 7,179,900)—Office Action dated Apr. 4, 2005.
U.S. Appl. No. 10/403,180 (U.S. Patent No. 7,179,900)—Office Action dated Oct. 19, 2005.
U.S. Appl. No. 10/403,180 (U.S. Patent No. 7,179,900)—Office Action dated Mar. 30, 2006.
U.S. Appl. No. 10/403,180 (U.S. Patent No. 7,179,900)—Office Action / Notice of Allowability dated Sep. 6, 2006.
U.S. Appl. No. 10/900,230 (U.S. Publ. No. 2005/0002926)—Office Action dated Jan. 24, 2006.

U.S. Appl. No. 10/900,230 (U.S. Publ. No. 2005/0002926)—Office Action dated Jun. 30, 2006.
U.S. Appl. No. 10/900,230 (U.S. Publ. No. 2005/0002926)—Office Action dated Dec. 26, 2006.
U.S. Appl. No. 10/900,230 (U.S. Publ. No. 2005/0002926)—Office Action dated Jun. 27, 2007.
U.S. Appl. No. 10/900,230 (U.S. Publ. No. 2005/0002926)—Office Action dated Feb. 21, 2008.
U.S. Appl. No. 10/900,230 (U.S. Publ. No. 2005/0002926)—Office Action dated Sep. 18, 2008.
U.S. Appl. No. 10/962,285 (U.S. Patent No. 7,323,172)—Office Action dated Oct. 26, 2006.
U.S. Appl. No. 10/962,285 (U.S. Patent No. 7,323,172)—Office Action dated Apr. 13, 2007.
U.S. Appl. No. 10/962,285 (U.S. Patent No. 7,323,172)—Office Action / Notice of Allowability dated Sep. 6, 2007.
U.S. Appl. No. 11/643,982 (U.S. Publ. No. 2007/0196916)—Office Action dated Sep. 2, 2008.
U.S. Appl. No. 11/263,230 (U.S. Publ. No. 2006/0115485)—Office Action dated Jan. 9, 2008.
U.S. Appl. No. 11/263,230 (U.S. Publ. No. 2006/0115485)—Office Action dated Oct. 2, 2008.
U.S. Appl. No. 09/796,848 (U.S. Publ. No. 2002/0098189)—Office Action dated Jun. 18, 2002.
U.S. Appl. No. 09/796,848 (U.S. Publ. No. 2002/0098189)—Office Action dated Dec. 29, 2003.
U.S. Appl. No. 09/796,848 (U.S. Publ. No. 2002/0098189)—Office Action dated Oct. 29, 2004.
U.S. Appl. No. 09/796,848 (U.S. Publ. No. 2002/0098189)—Office Action dated Jul. 13, 2005.
U.S. Appl. No. 09/796,848 (U.S. Publ. No. 2002/0098189)—Office Action dated Apr. 4, 2006.
U.S. Appl. No. 09/796,848 (U.S. Publ. No. 2002/0098189)—Office Action dated Jul. 27, 2007.
U.S. Appl. No. 09/796,848 (U.S. Publ. No. 2002/0098189)—Office Action dated Apr. 14, 2008.
U.S. Appl. No. 09/771,415 (U.S. Patent No. 6,656,467)—Office Action dated Jun. 18, 2002.
U.S. Appl. No. 09/771,415 (U.S. Patent No. 6,656,467)—Office Action dated Feb. 10, 2003.
U.S. Appl. No. 09/771,415 (U.S. Patent No. 6,656,467)—Office Action / Notice of Allowability dated May 6, 2003.
U.S. Appl. No. 10/657,363 (U.S. Publ. No. 2004/0098189)—Office Action dated May 30, 2007.
U.S. Appl. No. 10/657,363 (U.S. Publ. No. 2004/0098189)—Office Action dated Dec. 14, 2007.
Dall'Acqua Declaration (dated Jun. 16, 2008)—Filed in U.S. Appl. No. 10/657,363 (U.S. Publ. No. 2004/0098189) on Jun. 16, 2008.
U.S. Appl. No. 10/020,354 (U.S. Patent No. 7,083,784)—Office Action dated Apr. 7, 2004.
U.S. Appl. No. 10/020,354 (U.S. Patent No. 7,083,784)—Office Action dated Nov. 17, 2004.
U.S. Appl. No. 10/020,354 (U.S. Patent No. 7,083,784)—Office Action dated Jun. 1, 2005.
U.S. Appl. No. 10/020,354 (U.S. Patent No. 7,083,784)—Office Action / Notice of Allowability dated Dec. 15, 2005.
Dall'Acqua Declaration (dated Oct. 3, 2005)—Filed in U.S. Appl. No. 10/020,354 (U.S. Patent No. 7,083,784) on Oct. 8, 2005.
U.S. Appl. No. 11/397,328 (U.S. Publ. No. 2006/0198840)—Office Action dated Oct. 18, 2007.
U.S. Appl. No. 11/397,328 (U.S. Publ. No. 2006/0198840)—Office Action / Notice of Allowability dated Aug. 7, 2008.
U.S. Appl. No. 10/461,904 (U.S. Patent No. 7,132,100)—Office Action dated Dec. 14, 2004.
U.S. Appl. No. 10/461,904 (U.S. Patent No. 7,132,100)—Office Action dated Nov. 25, 2005.
U.S. Appl. No. 10/461,904 (U.S. Patent No. 7,132,100)—Office Action / Notice of Allowability dated May 2, 2006.
U.S. Appl. No. 11/362,267 (U.S. Patent No. 7,294,336)—Office Action dated May 4, 2007.
U.S. Appl. No. 11/362,267 (U.S. Patent No. 7,294,336)—Office Action / Notice of Allowability dated Aug. 6, 2007.
U.S. Appl. No. 10/461,863 (U.S. Patent No. 7,425,618)—Office Action dated Dec. 18, 2006.
U.S. Appl. No. 10/461,863 (U.S. Patent No. 7,425,618)—Office Action dated Jun. 11, 2007.
U.S. Appl. No. 10/461,863 (U.S. Patent No. 7,425,618)—Office Action / Notice of Allowability dated Nov. 19, 2007.
The Impact-RSV Study Group, 1998. Palivizumab, a humanized respiratory syncytial virus monoclonal antibody, reduces hospitalization from respiratory syncytial virus infection in high-risk infants. Pediatrics. 102(3 Pt 1):531-537.
Shields et al., 2001. High resolution mapping of the binding site on human IgG1 for Fc gamma RI, Fc gamma RII, Fc gamma RIII, and FcRn and design of IgG1 variants with improved binding to the Fc gamma R. J Biol Chem. 276(9):6591-6604.
U.S. Appl. No. 10/900,230 (U.S. Publ. No. 2005/0002926)—Interview Summary dated Mar. 27, 2009.
U.S. Appl. No. 09/796,848 (U.S. Publ. No. 2002/0098189)—Office Action dated Jan. 22, 2009.
U.S. Appl. No. 10/657,363 (U.S. Publ. No. 2004/0131609)—Office Action / Notice of Allowability dated Dec. 31, 2008.
U.S. Appl. No. 10/900,230 (U.S. Publ. No. 2005/0002926)—Office Action / Notice of Allowability dated Jun. 17, 2009.
U.S. Appl. No. 11/643,982 (U.S. Publ. No. 2007/0196916)—Office Action / Notice of Allowability dated Feb. 13, 2009.
U.S. Appl. No. 11/263,230 (U.S. Publ. No. 2006/0115485)—Office Action dated Mar. 30, 2009.
U.S. Appl. No. 10/657,363 (U.S. Publ. No. 2004/0131609)—Office Action dated Jul. 6, 2009.
U.S. Appl. No. 11/397,328 (U.S. Publ. No. 2006/0198840)—Office Action dated Feb. 13, 2009.
U.S. Appl. No. 11/649,455 ( U.S. Publ. No. 2007/0122403)—Office Action dated Feb. 26, 2009.
U.S. Appl. No. 12/559,375, filed Sep. 14, 2009, Young et al.
U.S. Appl. No. 12/691,433, filed Jan. 1, 2010, Dall' acqua et al.
U.S. Appl. No. 10/461,863 (U.S. Patent No. 7,425,618)—Supplemental Notice of Allowability dated Jul. 31, 2008.
Norderhaug et al., 1997, "Versatile vectors for transient and stable expression of recombinant antibody molecules in mammalian cells", J. Immunolo. Methods, 204:77-87.
Kingston, R., 2003, "Chapter 9: Introduction of DNA into Mammalian Cells", in "Current Protocols in Molecular Biology", John Wiley & Sons, pp. 9.0.1-9.0.5.
Trill et al., 1995. "Production of monoclonal antibodies in COS and CHO cells", Curr Opin Biotechnol: 6(5):553-60.
Kipriyanov and Little, 1999, "Generation of Recombinant Antibodies", Mol Biotechnol., 12(2):173-201.
Bebbington et al., 1992, "High-level expression of a recombinant antibody from myeloma cells using a glutamine synthetase gene as an amplifiable selectable marker", Biotechnology (N Y), 10(2):169-75.

Conditioned Medium (From Cell Culture)

↓

| HS50 Chromatography Column Cycle |
| --- |
| Benzonase Treatment |

↓

| Protein A Chromatography Column Cycle(s) |
| --- |
| Nanofiltration |

↓

| Low pH Treatment |
| --- |
| Q Chromatography Column Cycle |

↓

(Liquid Formulations of SYNAGIS®)

FIG. 1

SEQUENCE LISTING

```
<160> NUMBER OF SEQ ID NOS: 6

<210> SEQ ID NO 1
<211> LENGTH: 7
<212> TYPE: PRT
<213> ORGANISM: Homo sapiens

<400> SEQUENCE: 1
```

```
-continued

Thr Ser Gly Met Ser Val Gly
1               5

<210> SEQ ID NO 2
<211> LENGTH: 16
<212> TYPE: PRT
<213> ORGANISM: Homo sapiens

<400> SEQUENCE: 2

Asp Ile Trp Trp Asp Asp Lys Lys Asp Tyr Asn Pro Ser Leu Lys Ser
1               5                   10                  15

<210> SEQ ID NO 3
<211> LENGTH: 10
<212> TYPE: PRT
<213> ORGANISM: Homo sapiens

<400> SEQUENCE: 3

Ser Met Ile Thr Asn Trp Tyr Phe Asp Val
1               5                   10

<210> SEQ ID NO 4
<211> LENGTH: 10
<212> TYPE: PRT
<213> ORGANISM: Homo sapiens

<400> SEQUENCE: 4

Lys Cys Gln Leu Ser Val Gly Tyr Met His
1               5                   10

<210> SEQ ID NO 5
<211> LENGTH: 7
<212> TYPE: PRT
<213> ORGANISM: Homo sapiens

<400> SEQUENCE: 5

Asp Thr Ser Lys Leu Ala Ser
1               5

<210> SEQ ID NO 6
<211> LENGTH: 9
<212> TYPE: PRT
<213> ORGANISM: Homo sapiens

<400> SEQUENCE: 6

Phe Gln Gly Ser Gly Tyr Pro Phe Thr
1               5
```

STABILIZED LIQUID ANTI-RSV ANTIBODY FORMULATIONS

This application is a continuation of U.S. application Ser. No. 11/362,267, filed Feb. 24, 2006, which is a continuation of U.S. application Ser. No. 10/461,904, filed Jun. 13, 2003, which is entitled to and claims priority benefit to U.S. provisional application Ser. No. 60/388,921 filed Jun. 14, 2002, all of which are incorporated herein by reference in their entirety.

1. INTRODUCTION

The present invention relates to liquid formulations of SYNAGIS® (palivizumab) or an antigen-binding fragment thereof, which formulations exhibit stability, low to undetectable levels of antibody fragmentation, low to undetectable levels of aggregation, and very little to no loss of the biological activity (e.g., therapeutic efficacy) SYNAGIS® or an antigen-binding fragment thereof even during or after long periods of storage. In particular, the present invention relates to liquid formulations of SYNAGIS® or an antigen-binding fragment thereof which formulations are substantially free of surfactant and/or inorganic salts. The present invention also relates to methods of preventing, treating or ameliorating symptoms associated with a respiratory syncytial virus (RSV) infection utilizing liquid formulations of SYNAGIS® or an antigen binding fragment thereof.

2. BACKGROUND OF THE INVENTION

Respiratory syncytial virus (RSV) is the leading cause of serious lower respiratory tract disease in infants and children (Feigen et al., eds., 1987, In: *Textbook of Pediatric Infectious Diseases*, W B Saunders, Philadelphia at pages 1653-1675; New Vaccine Development, Establishing Priorities, Vol. 1, 1985, National Academy Press, Washington D.C. at pages 397-409; and Ruuskanen et al., 1993, Curr. Probl. Pediatr. 23:50-79). The yearly epidemic nature of RSV infection is evident worldwide, but the incidence and severity of RSV disease in a given season vary by region (Hall, C. B, 1993, Contemp. Pediatr. 10:92-110). In temperate regions of the northern hemisphere, it usually begins in late fall and ends in late spring (Halt C. B., 1995, In: Mandell G. L, Bennett J. E., Dolin R., eds., 1995, *Principles and Practice of infections Diseases*. 4th ed &, Churchill Livingstone, New York at pages 1501-1519). It is estimated that RSV illness results in 90,000 hospitalizations and causes 4,500 deaths annually in the United States. Primary RSV infection occurs most often in children from 6 weeks to 2 years of age and uncommonly in the first 4 weeks of life during nosocomial epidemics (Hall et al., 1979, New Engl. J. Med. 300:393-396). RSV is estimated to cause as much as 75% of all childhood bronchiolitis and up to 40% of all pediatric pneumonias (Cunningham, C. K. et al., 1991, *Pediatrics* 88:527-532). Children at increased risk from RSV infection include preterm infants (Hall et al., 1979, New Engl. J. Med. 300:393-396) and children with bronchopulmonary dysplasia (Groothuis et al., 1988, Pediatrics 82:199-203), congenital heart disease MacDonald et al., New Engl. J. Med. 307:397-400), congenital or acquired immunodeficiency (Ogra et al., 1988, Pediatr. Infect. Dis. J. 7:246-249; and Pohl et al., 1992, J. Infect. Dis. 165:166-169), and cystic fibrosis (Abman et al., 1988, J. Pediatr. 113:826-830). The fatality rate in infants with heart or lung disease who are hospitalized with RSV infection is 3%-4% (Navas et al., 1992, J. Pediatr. 121:348-354).

RSV infects adults as well as infants and children. In healthy adults, RSV causes predominantly upper respiratory tract disease. It has recently become evident that some adults, especially the elderly, have symptomatic RSV infections more frequently than had been previously reported (Evans, A. S., eds., 1989, Viral Infections of Humans. Epidemiology and Control, $3^{rd}$ ed., Plenum Medical Book, New York at pages 525-544). Several epidemics also have been reported among nursing home patients and institutionalized young adults (Falsey, A. R., 1991, Infect. Control Hosp. Epidemiol. 12:602-608; and Garvin et al., 1980, Br. Med. J. 281:1253-1254). Finally, RSV may cause serious disease in immunosuppressed persons, particularly bone marrow transplant patients (Hertz et al., 1989, Medicine 68:269-281).

Treatment options for established RSV disease are limited. Severe RSV disease of the lower respiratory tract often requires considerable supportive care, including administration of humidified oxygen and respiratory assistance Fields et al., eds, 1990, Fields Virology, $2^{nd}$ ed., Vol. 1, Raven Press, New York at pages 1045-1072). The only drug approved for treatment of infection is the antiviral agent ribavirin (American Academy of Pediatrics Committee on Infectious Diseases, 1993, Pediatrics 92:501-504). It has been shown to be effective in the treatment of RSV pneumonia and bronchiolitis, modifying the course of severe RSV disease in immunocompetent children (Smith et al., 1991, New Engl. J. Med. 325:24-29). However, ribavirin has a number of limitations including high cost need for prolonged aerosol administration and potential risk to pregnant women as well as to exposed health care personnel. The American Academy of Pediatrics Committee on Infectious Diseases revised their recommendation for use of ribavirin. The current recommendation is that the decision to use ribavirin should be based on the particular clinical circumstances and physician's experience (American Academy of Pediatrics. Summaries of infectious Diseases. In: Pickering L. K, ed., 2000 *Red Book: Report of the Committee on Infectious Diseases*. 25th ed., Elk Grove Village, Ill., American Academy of Pediatrics, 2000, pp. 483-487).

While a vaccine might prevent RSV infection, no vaccine is yet licensed for this indication. A major obstacle to vaccine development is safety. A formalin-inactivated vaccine, though immunogenic, unexpectedly caused a higher and more severe incidence of lower respiratory tract disease due to RSV in immunized infants than in infants immunized with a similarly prepared trivalent parainfluenza vaccine (Kim et al., 1969, Am. J. Epidemiol. 89:422-434; and Kapikian et al., 1969, Am. J. Epidemiol. 89:405-421). Several candidate RSV vaccines have been abandoned and others are under development (Murphy et al., 1994, Virus Res. 32:13-36), but even if safety issues are resolved, vaccine efficacy must also be improved. A number of problems remain to be solved. Immunization would be required in the immediate neonatal period since the peak incidence of lower respiratory tract disease occurs at 2-5 months of age. The immaturity of the neonatal immune response together with high titers of maternally acquired RSV antibody may be expected to reduce vaccine immunogenicity in the neonatal period (Murphy et al., 1988, J. Virol. 62:3907-3910; and Murphy et al., 1991, Vaccine 9:185-189). Finally, primary RSV infection and disease do not protect well against subsequent RSV disease Henderson et al., 1979, New Engl. J. Med. 300:530-534).

Currently, the only approved approach to prophylaxis of RSV disease is passive immunization. Initial evidence suggesting a protective role for IgG was obtained from observations involving maternal antibody in ferrets (Prince, G. A, Ph.D. diss., University of California, Los Angeles, 1975) and humans (Lambrecht et al, 1976, J. Infect Dis. 134:211-217; and Glezen et al., 1981, J. Pediatr. 98:708-715). Hemming et al. (Morell et al., eds., 1986, Clinical Use of Intravenous Immunoglobulins, Academic Press, London at pages 285-294) recognized the possible utility of RSV antibody in the treatment or prevention of RSV infection during studies involving the pharmacokinetics of an intravenous immune globulin (IVIG) in newborns suspected of having neonatal sepsis. They noted that one infant, whose respiratory secretions yielded RSV, recovered rapidly after IVIG infusion. Subsequent analysis of the IVIG lot revealed an unusually high titer of RSV neutralizing antibody. This same group of investigators then examined the ability of hyperimmune serum or immune globulin, enriched for RSV neutralizing antibody, to protect cotton rats and prima against RSV infection (Prince et al., 1985, Virus Res. 3:193-206; Prince et al., 1990, J. Virol. 64:3091-3092; Hemming et al., 1985, J. Infect. Dis. 152:1083-1087; Prince et al., 1983, Infect. Immun. 42:81-87; and Prince et al., 1985, J. Virol. 55:517-520). Results of these studies suggested that RSV neutralizing antibody given prophylactically inhibited respiratory tract replication of RSV in cotton rats. When given therapeutically. RSV antibody reduced pulmonary viral replication both in cotton rats and in a nonhuman primate model. Furthermore, passive infusion of immune serum or immune globulin did not produce enhanced pulmonary pathology in cotton rats subsequently challenged with RSV.

A humanized antibody directed to an epitope in the A antigenic site of the F protein of RSV, SYNAGIS®, comprising variable heavy (VH) complementarity determining regions (CDRs) having the amino acid sequences of SEQ ID NO:1-3 and variable light (VL) CDRs having the amino acid sequences of SEQ ID NO:4-6, is approved for intramuscular administration to pediatric patients for prevention of serious lower respiratory tract disease caused by RSV at recommended monthly doses of 15 mg/kg of body weight throughout the RSV season (November through April in the northern hemisphere). SYNAGIS® is a composite of human (95%) and murine (5%) antibody sequences. See, Johnson et al., 1997, J. Infect Diseases 176:1215-1224 and U.S. Pat. No. 5,824,307, the entire contents of which are incorporated herein by reference. The human heavy chain sequence was derived from the constant domains of human IgG1 and the variable framework regions of the VH genes of Cor (Press et al., 1970, Biochem. J. 117:641-660) and Cess (Takahi et al., 1984, Proc. Natl. Acad. Sci. USA 81:194-198). The human light chain sequence was derived from the constant domain of C6 and the variable framework regions of the VL gene K104 with J6-4 (Bentley et al., 1980, Nature 288:5194-5198). The murine sequences were derived from a murine monoclonal antibody, Mab 1129 (Beeler et al., 1989, J. Virology 63:2941-2950), in a process which involved the grafting of the murine complementarity determining regions into the human antibody frameworks.

SYNAGIS® has high specific activity against RSV in vitro (approximately 50-100 times that of RESPIGAM® (respiratory syncytial virus immune globulin, human) and is known to neutralize a broad range of RSV isolates. Since it is not derived from human plasma, prophylactic treatment with SYNAGIS® does not carry potential risk of transmission of blood borne pathogens.

SYNAGIS® was initially formulated as a liquid for IV use, at a concentration of 10 mg/ml SYNAGIS® in phosphate buffered saline. A lyophilized formulation of SYNAGIS®, which allows a higher concentration (100 mg/ml after reconstitution, in 50 mM histidine and 3.2 mM glycine buffer with 6% (w/v) mannitol at pH 6.0) of the antibody than this initial liquid formulation, was produced later to allow intramuscular use. The lyophilized formulation of SYNAGIS® is prepared by lyophilizing SYNAGIS® at 54 mg/ml in an aqueous solution containing 25 mM histidine, 1.6 mM glycine, and 3% (w/v) mannitol at pH 6.0. The initial liquid formulation in PBS and the lyophilized formulation of SYNAGIS® have been tested in phase I clinical studies in healthy adults. The lyophilized formulation was tested in phase I through phase IV studies in pediatric patients. SYNAGIS®, at doses of 15 mg/kg to 30 mg/kg for adults is found to be well tolerated, and 15 mg/kg for children is found to be safe and efficacious for RSV prophylaxis. The lyophilized formulation was approved in 1998 by the FDA for use in the prevention of serious lower respiratory tract disease caused by RSV in children at high risk of RSV disease.

However, the lyophilized formulation has a number of limitations, including a prolonged process for lyophilization and resulting high cost for manufacturing. In addition, the lyophilized formulation has to be reconstituted aseptically and accurately by healthcare practitioners prior to administering to patients. The reconstitution step itself requires certain specific procedures: (1) a sterile diluent (i.e., water or 5% dextrose in water for intravenous administration and water for intramuscular administration) is added to the vial containing lyophilized SYNAGIS®, slowly and aseptically, and the vial must be swirled very gently for 30 seconds to avoid foaming (2) the reconstituted SYNAGIS® needs to stand at room temperature for a minimum of 20 minutes until the solution clarifies; and (3) the reconstituted preparation must be administered within six (6) hours after the reconstitution. Such reconstitution procedure is cumbersome and the time limitation after the reconstitution can cause a great inconvenience in administering the formulation to patients, leading to significant waste, if not reconstituted properly or if the reconstituted dose is not used within six (6) hour and must be discarded.

Thus, a need exists for a liquid formulation of SYNAGIS® at a concentration comparable to or higher than the reconstituted lyophilized formulation so that there is no need to reconstitute the formulation prior to administration. This allows health care practitioners much quicker and easier administration of SYNAGIS® to a patient.

Prior liquid antibody preparations have short shelf lives and may lose biological activity of the antibodies resulting from chemical and physical instabilities during the storage. Chemical instability may be caused by deamidation, racemization, hydrolysis, oxidation, beta elimination or disulfide exchange, and physical instability may be caused by antibody denaturation, aggregation, precipitation or adsorption. Among those, aggregation, deamidation and oxidation are known to be the most common causes of the antibody degradation (Wang et al., 1988, *J. of Parenteral Science & Technology* 42(Suppl):S4-S26; Cleland et al., 1993, *Critical Reviews in Therapeutic Drug Carrier Systems* 10(4):307-377). Thus, there is a need for a stable liquid formulation of SYNAGIS® or an antigen-binding fragment thereof effective to prevent RSV infection.

3. SUMMARY OF INVENTION

The present invention is based, in part, on the development of high concentration liquid formulations of SYNAGIS® or an antigen-binding fragment thereof, which formulations exhibit, in the absence of surfactant, inorganic salts, and/or other excipients, stability, low to undetectable levels of antibody fragmentation and/or aggregation, and very little to no loss of the biological activity(ies) of SYNAGIS® or an antigen-binding fragment thereof during manufacture, preparation, transportation, and storage. The liquid formulations of the present invention facilitate the administration of SYNAGIS® or an antigen-binding fragment thereof for the prevention, treatment, management and/or amelioration of a RSV infection or one or more symptoms thereof. In particular, the liquid formulations of the present invention enable a healthcare professional to quickly administer a sterile dosage of SYNAGIS® or an antigen-binding fragment thereof without having to accurately and aseptically reconstitute the antibody or antibody fragment prior to administration as required for the lyophilized dosage form. Such liquid formulations of SYNAGIS® can be also manufactured more easily and cost effectively than the lyophilized formulation since liquid formulations do not require a prolonged drying step, such as lyophilization, freeze-drying, etc. The liquid formulations are made by a process in which the antibody being formulated is in an aqueous phase throughout the purification and formulation process. Preferably, the liquid formulations are made by a process that does not include a drying step, for example, but not by way of limitation, a lyophilization, freeze-drying, spray-drying, or air-drying step.

The present invention provides liquid formulations of SYNAGIS® or an antigen-binding fragment thereof, substantially free of surfactant, inorganic salts, sugars, and/or other common excipients, said formulations comprising histidine and a concentration of about 15 mg/ml or higher of SYNAGIS® or an antigen-binding fragment thereof. Optionally, the formulation may further comprise glycine. Alternatively, the formulation of the present invention may further comprise other common excipients, such as saccharides, polyols and amino acids, including, but not limited to, arginine, lysine, and methionine. The present invention also provides liquid formulations substantially free of surfactant, inorganic salts, sugars, and/or other commonly-known excipients, said formulation having a pH ranging from about 5.0 to about 7.0, preferably about 5.5 to 6.5, more preferably about 5.8 to about 6.2, and most preferably about 6.0, and comprising histidine and a concentration of about 15 mg/ml or higher of SYNAGIS® or an antigen-binding fragment thereof.

The present invention encompasses stable liquid formulations of SYNAGIS® which exhibit low to undetectable levels of antibody aggregation and/or fragmentation with very little to no loss of biological activity(ies) of SYNAGIS® or an antigen-binding fragment thereof during manufacture, preparation, transportation and long periods of storage. The present invention also encompasses stable liquid formulations of modified forms of SYNAGIS® or an antigen-binding fragment thereof that have increased in vivo half-lives relative to unmodified SYNAGIS® or an antigen-binding fragment thereof said formulations exhibiting low to undetectable levels of antibody aggregation and/or fragmentation, and very little to no loss of biological activity(ies) of SYNAGIS® or an antigen-binding fragment thereof.

The present invention encompasses liquid formulations of SYNAGIS® or an antigen-binding fragment thereof, said formulations having stability at 38°-42° C. as assessed by high performance size exclusion chromatography (HPSEC). The liquid formulations of the present invention exhibits stability, as assessed by HSPEC, at the temperature ranges of 38° C.-42° C. for at least 60 days (in specific embodiments, not more than 120 days), of 20° C.-24° C. for at least 1 year, and of 2° C.-8° C. for at least 3 years. The present invention also encompasses liquid formulations of SYNAGIS® or an antigen-binding fragment thereof, said formulations having low to undetectable aggregation as measured by HPSEC. In a preferred embodiment, the liquid formulations of the present invention exhibit stability at 38°-42° C. for at least 60 days and exhibit low to undetectable levels of antibody aggregation as measured by HPSEC, and further, exhibit very little to no loss of biological activity (ies) of SYNAGIS® or an antigen-binding fragment thereof compared to the reference antibodies as measured by antibody binding assays such as, e.g., ELISAs.

The present invention provides methods for preparing liquid formulations of SYNAGIS® or an antigen-binding fragment thereof. The liquid formulations of the present invention are prepared by maintaining SYNAGIS® or an antigen-binding fragment thereof in an aqueous solution at any time during the preparation. In other words, the liquid formulations are prepared without involving any step of drying SYNAGIS® or an antigen-binding fragment thereof or the formulations themselves by, for example, lyophilization, vacuum drying, etc.

The present invention provides methods for preparing liquid formulations of SYNAGIS® or an antigen-binding fragment thereof, said methods comprising concentrating a fraction of purified SYNAGIS® or an antigen-binding fragment thereof to a final concentration of about 15 mg/ml about 20 mg/ml, about 30 mg/ml, about 40 mg/ml, about 50 mg/ml, about 60 mg/ml, about 70 mg/ml, about 80 mg/ml, about 90 mg/ml, about 100 mg/ml, about 200 mg/ml, about 250 mg/ml, or about 300 mg/ml using a semi-permeable membrane with an appropriate molecular weight (mw) cutoff (e.g., 30 kD cutoff for SYNAGIS® and $F(ab')_2$ fragments thereof; and 10 kD cutoff for SYNAGIS® fragments such Fab fragments), and diafiltering the concentrated antibody fraction into the formulation buffer using the same membrane. The formulation buffer of the present invention comprises histidine at a concentration ranging from about 1 mM to about 100 mM, about 10 mM to about 50 mM, about 20 mM to about 30 mM, or about 23 mM to about 27 mM, and is most preferably about 25 mM. To obtain an appropriate pH for SYNAGIS® or an antigen-binding fragment thereof, it is preferably that histidine (and glycine, if added) is first dissolved in water to obtain a buffer solution with higher pH than the desired pH and then the pH is brought down to the desired level by the addition of HCl. This way, the formation of inorganic salts (e.g., the formation of NaCl when, e.g., histidine hydrochloride is used as the source of histidine and the pH is raised to the desired level by the addition of NaOH) can be avoided.

The liquid formulations of the present invention may be sterilized by sterile filtration using a 0.2µ or a 0.22µ filter. Sterilized liquid formulations of the present invention may be administered to a subject to prevent treat or ameliorate one or more symptoms associated with a RSV infection or a symptom thereof.

The present invention also provides kits comprising the liquid formulations of SYNAGIS® or an antigen-binding fragment thereof for use by, e.g. a healthcare professional. The present invention further provides methods of preventing, treating managing or ameliorating a RSV infection or one or more symptoms thereof by administering the liquid formulations of the present invention.

3.1 Terminology

As used herein, all liquid formulations of SYNAGIS® and/or fragments thereof that immunospecifically bind to a RSV antigen described above are collectively referred to as "liquid formulations of the invention," "SYNAGIS® liquid formulations of the invention," or "liquid formulations of SYNAGIS® or an antigen-binding fragment thereof."

As used herein, the term "cytokine receptor modulator" refers to an agent which modulates the phosphorylation of a cytokine receptor, the activation of a signal transduction pathway associated with a cytokine receptor, and/or the expression of a particular protein such as a cytokine. Such an agent may directly or indirectly modulate the phosphorylation of a cytokine receptor, the activation of a signal transduction pathway associated with a cytokine receptor, and/or the expression of a particular protein such as a cytokine. Thus, examples of cytokine receptor modulators include, but are not limited to, cytokines, fragments of cytokines, fusion proteins and antibodies that immunospecifically binds to a cytokine receptor or a fragment thereof. Further, examples of cytokine receptor modulators include, but are not limited to, peptides, polypeptides (e.g., soluble cytokine receptors), fusion proteins and antibodies that immunospecifically binds to a cytokine or a fragment thereof.

As used herein, the terms "SYNAGIS® fragment", "antigen-binding fragment" and like terms used in the context of SYNAGIS® refer to a fragment of SYNAGIS® that immunospecifically binds to a RSV antigen Fragments of SYNAGIS® may be generated by any technique known to those skilled in the art. For example, Fab and F(ab')$_2$ fragments may be produced by proteolytic cleavage of immunoglobulin molecules, using enzymes such as papain (to produce Fab fragments) or pepsin (to produce F(ab')$_2$ fragments). F(ab')$_2$ fragments contain the complete light chain, and the variable region, the CH1 region and the hinge region of the heavy chain. Preferably, the fragment also binds to a RSV antigen, more preferably to the same epitope as SYNAGIS®.

As used herein, the term "effective amount" refers to the amount of a therapy (e.g., a prophylactic or therapeutic agent), which is sufficient to reduce the severity, and/or duration of a RSV infection, ameliorate one or more symptoms thereof, prevent the advancement of a RSV infection, or cause regression of a RSV infection, or which is sufficient to result in the prevention of the development, recurrence, onset, or progression of a RSV infection or one or more symptoms thereof, or enhance or improve the prophylactic and/or therapeutic effect(s) of another therapy (e.g., another therapeutic agent). In a specific embodiment, an effective amount of a therapeutic or a prophylactic agent reduces one or more of the following steps of a RSV life cycle: the docking of the virus particle to a cell, the introduction of viral genetic information into a cell, the expression of viral proteins, the production of new virus particles and the release of virus particles from a cell by at least 5%, preferably at least 10%, at least 15%, at least 20%, at least 25%, at least 30%, at least 35%, at least 40%, at least 45%, at least 50%, at least 55%, at least 60%, at least 65%, at least 70%, at least 75%, at least 80%, at least 85%, at least 90%, at least 95%, or at least 100%. In another specific embodiment, an effective amount of a therapeutic or a prophylactic agent reduces the replication, multiplication or spread of a virus by at least 5%, preferably at least 10%, at least 15%, at least 20%, at least 25%, at least 30%, at least 350%, at least 40%, at least 45%, at least 50%, at least 55%, at least 60%, at least 65%, at least 70%, at least 75%, at least 80%, at least 85%, at least 90%, at least 95%, or at least 100%.

As used herein, the term "epitope" refers to a portion of a RSV polypeptide or protein having antigenic or immunogenic activity in an animal, preferably a mammal, and most preferably in a human. An epitope having immunogenic activity is a portion of a RSV polypeptide or protein that elicits an antibody response in an animal. An epitope having antigenic activity is a portion of a RSV polypeptide or protein to which an antibody immunospecifically binds as determined by any method well known in the art, for example, by the immunoassays described herein Antigenic epitopes need not necessarily be immunogenic. Specifically, the epitope of SYNAGIS® is the A antigenic site of the F protein of RSV.

As used herein, the term "excipients" refers to inert substances which are commonly used as a diluent, vehicle, preservatives, binders, or stabilizing agent for drugs and includes, but not limited to, proteins (e.g., serum albumin etc.), amino acids (e.g., aspartic acid, glutamic acid, lysine, arginine, glycine, histidine, etc.), fatty acids and phospholipids (e.g., alkyl sulfonates, caprylate, etc.), surfactants (e.g., SDS, polysorbate, nonionic su t, etc.), saccharides (e.g., sucrose, maltose, trehalose, etc.) and polyols (e.g., mannitol sorbitol etc.). Also see Remington's Pharmaceutical Sciences (by Joseph P. Remington, 18th ed., Mack Publishing Co., Easton, Pa.) which is hereby incorporated in its entirety. Preferably, the excipients impart a beneficial physical property to the formulation, such as increased protein stability, increased protein solubility and decreased viscosity.

The term "fragment" as used herein refers to a peptide, polypeptide, or protein (including an antibody) comprising an amino acid sequence of at last 5 contiguous amino acid residues, at least 10 contiguous amino acid residues, at least 15 contiguous amino acid residues, at least 20 contiguous amino acid residues, at least 25 contiguous amino acid residues, at least 40 contiguous amino acid residues, at least 50 contiguous amino acid residues, at least 60 contiguous amino acid residues, at least 70 contiguous amino acid residues, at least contiguous 80 amino acid residues, at least contiguous 90 amino acid residues, at least contiguous 100 amino acid residues, at least contiguous 125 amino acid residues, at least 150 contiguous amino acid residues, at least contiguous 175 amino acid residues, at least contiguous 200 amino acid residues, or at least contiguous 250 amino acid residues of the amino acid sequence of another polypeptide or protein. In a specific embodiment, a fragment of a protein or polypeptide retains at least one function of the protein or polypeptide. La another embodiment, a fragment of a protein or polypeptide retains at least two, three or four functions of the protein or polypeptide. Preferably a fragment of an antibody that immunospecifically binds to a RSV antigen retains the ability to bind to a RSV antigen.

As used herein, the term "fusion protein" refers to a polypeptide or protein that comprises an amino acid sequence of a first protein, polypeptide or fragment, analog or derivative thereof, and an amino acid sequence of a heterologous protein or polypeptide (i.e., a second protein, polypeptide or fragment, analog or derivative thereof different than the first protein or functional fragment, analog or derivative thereof). In one embodiment, a fusion protein comprises a prophylactic or therapeutic agent fused to a heterologous protein, polypeptide or peptide. In accordance with this embodiment, the heterologous protein, polypeptide or peptide may or may not be a different type of prophylactic or therapeutic agent.

As used herein, the term "human infant" refers to a human less than 24 months, preferably less than 16 months, less than 12 months, less than 6 months, less than 3 months, less than 2 months, or less than 1 month of age.

As used herein, the term "human infant born prematurely" refers to a human born at less than 40 weeks gestational age, preferably less than 35 weeks gestational age, who is less than 6 months old, preferably less than 3 months old, more preferably less than 2 months old, and most preferably less than 1 month old.

As used herein, the term "high concentration" refers to a concentration of 50 mg or higher, preferably 95 mg/ml or higher of an antibody or fragment thereof that immunospecifically binds to a RSV antigen, in an antibody formulations.

As used herein, the term "host cell" includes a subject cell transfected or transformed with a nucleic acid molecule and the progeny or potential progeny of such a cell. Progeny of such a cell may not be identical to the parent cell transfected with the nucleic acid molecule due to mutations or environmental influences that may occur in succeeding generations or integration of the nucleic acid molecule into the host cell genome.

As used herein, the term "immunospecifically binds a RSV antigen" and analogous terms refer to antibodies or fragments thereof that specifically bind to a RSV antigen thereof and do not specifically bind to other polypeptides. Antibodies or fragments that immunospecifically bind a RSV antigen may be cross-reactive with related antigens. Preferably, antibodies or fragments that immunospecifically bind a RSV antigen do not cross-react with other antigens. Antibodies or fragments that immunospecifically bind to and RSV antigen can be identified, for example, by immunoassays, BIAcore, isothermal titration calorimetry, or other techniques known to those of skilled in the art. An antibody or an antigen-binding fragment thereof binds specifically to a RSV antigen when it binds with higher affinity than to any cross-reactive antigen as determined using experimental techniques, such as radioimmunoassays (RIA) and enzyme-linked immunosorbent assays (ELISAs). See, e.g., Paul, ed., 1989, *Fundamental Immunology Second Edition*, Raven Press, New York at pages 332-336 for a discussion regarding antibody specificity.

The term "in combination" as used herein refers to the use of more than one therapies (e.g., prophylactic and/or therapeutic agents). The use of the term "in combination" does not restrict the order in which therapies (e.g., prophylactic and/or therapeutic agents) are administered to a subject with a RSV infection. A first therapy (e.g., a prophylactic or therapeutic agent) can be administered prior to (e.g., 5 minutes, 15 minutes, 30 minutes, 45 minutes, 1 hour, 2 hours, 4 hours, 6 hours, 12 hours, 24 hours, 48 hours, 72 hours, 96 hours, 1 week, 2 weeks, 3 weeks, 4 week 5 weeks, 6 weeks, 8 weeks, or 12 weeks before), concomitantly with, or subsequent to (e.g., 5 minutes, 15 minutes, 30 minutes, 45 minutes, 1 hour, 2 hours, 4 hours, 6 hours, 12 hours, 24 hours, 48 hours, 72 hours, 96 hours, 1 week, 2 weeks, 3 weeks, 4 weeks, 5 weeks, 6 weeks, 8 weeks, or 12 weeks after) the administration of a second therapy (e.g., a prophylactic or therapeutic agent) to a subject with a RSV infection.

As used herein, the term "inorganic salt" refers to any compounds, containing no carbon, that result from replacement of part or all of the acid hydrogen or an acid by a metal or a group acting like a metal and are often used as a tonicity adjusting compound in pharmaceutical compositions and preparations of biological materials. The most common inorganic salts are NaCl, KCl, $NaH_2PO_4$, etc.

An "isolated" or "purified" antibody is substantially free of cellular material or other contaminating proteins from the cell or tissue source from which the protein is derived, or substantially free of chemical precursors or other chemicals when chemically synthesized. The language "substantially free of cellular material" includes preparations of an antibody in which the polypeptide/protein is separated from cellular components of the cells from which it is isolated or recombinantly produced. Thus, an antibody that is substantially free of cellular material includes preparations of the antibody having less than about 30%, 20%, 10%, 5%, 2.5%, or 1%, (by dry weight) of contaminating protein. When the antibody is recombinantly produced, it is also preferably substantially free of culture medium, i.e., culture medium represents less than about 20%, 10%, or 5% of the volume of the protein preparation. When antibody is produced by chemical synthesis, it is preferably substantially free of chemical precursors or other chemicals, i.e., it is separated from chemical precursors or other chemicals which are involved in the synthesis of the protein. Accordingly, such preparations of the antibody have less than about 30%, 20%, 10%, 5% (by dry weight) of chemical precursors or compounds other than anybody of interest. In a preferred embodiment of the present invention, antibodies are isolated or purified.

As used herein, the phrase "low to undetectable levels of aggregation" refers to samples containing no more than 5%, no more than 4%, no more than 3%, no more than 2%, no more than 1%, and most preferably no more than 0.5%, aggregation by weight protein as measured by high performance size exclusion chromatography (HPSEC).

As used herein, the term "low to undetectable levels of fragmentation" refers to samples containing equal to or more than 80%, 85%, 90%, 95%, 98%, or 99%, of the total protein, for example, in a single peak as determined by high performance size exclusion chromatography (HPSEC), or in two (2) peaks (heavy- and light-chains) by reduced Capillary Gel Electrophoresis (rCGE), representing the non-degraded SYNAGIS® or a non-degraded fragment thereof which immunospecifically binds to a RSV antigen, and containing no other single peaks having more than 5%, more than 4%, more than 3%, more than 2%, more than 1%, or more than 0.5% of the total protein each. The term "Reduced-Capillary Gel Electrophoresis (CGE)" as used herein refers to capillary gel electrophoresis under reducing conditions sufficient to reduce disulfide bonds in SYNAGIS® or an antigen-binding fragment thereof.

As used herein, the terms "manage", "managing" and "Management" refer to the beneficial effects that a subject derives from a therapy (e.g., SYNAGIS® or an antigen binding fragment thereof), which does not result in a cure of a RSV infection. In certain embodiments, a subject is administered one or more therapies (e.g., prophylactic or therapeutic agents) to "manage" a RSV infection or a symptom thereof so as to prevent the progression or worsening of the infection.

As used herein, the term "modified" in the context of modified forms of SYNAGIS® or an antigen-binding fragment thereof refers to SYNAGIS® or an antigen-binding fragment thereof which has been altered by any method known in the art to increase its half life (see, e.g., Section 5.1.1., infra). SYNAGIS® and antigen-binding fragments thereof with improved in vivo half-lives and methods for preparing them are disclosed in International Publication No. WO 02/060919, filed Dec. 12, 2001, and U.S. patent application Ser. No. 10/020,354, filed Dec. 12, 2001, both entitled "Molecules with Extended Half-Lives, Compositions and Uses" and by L. Johnson et al. which are hereby incorporated by reference in their entireties. The term "modified" in the context of SYNAGIS® or an antigen-binding fragment thereof also refers to SYNAGIS® or an antigen-binding fragment modified by covalent attachment of any type of molecule to SYNAGIS® or an antigen-binding fragment thereof. For example, but not by way of limitation, SYNAGIS® or an antigen-binding fragment thereof may be modified, e.g., by glycosylation, acetylation, pegylation, phosphorylation, amidation, derivation by known protecting/blocking groups, proteolytic cleavage, linkage to a cellular ligand or other protein, etc.

As used herein, the term "pharmaceutically acceptable" means being approved by a regulatory agency of the Federal or a state government or listed in the U.S. Pharmacopia, European Pharmacopia or other generally recognized pharmacopia for use in animals, and more particularly in humans.

As used herein, the term "polyol" refers to a sugar that contains many —OH groups compared to a normal saccharide.

As used herein, the terms "prevent, "preventing", and prevention" refer to the prevention or reduction of the recurrence, onset, development or progression of a RSV infection, or the prevention or reduction of the severity and/or duration of a RSV infection or one or more symptoms thereof.

As used herein, the terms "prophylactic agent" and "prophylactic agents" refer to any agent(s) which can be used in the prevention of a RSV infection or one or more symptoms thereof. In certain embodiments, the term "prophylactic agent" refers to SYNAGIS® or an antigen-binding fragment thereof. In accordance with these embodiments, the antibody or antibody fragment may be a component of a liquid formulation of the invention. In certain other embodiments, the term "prophylactic agent" does not refer to SYNAGIS® or an antigen-binding fragment thereof. In yet other embodiments, the term "prophylactic agent" does not refer to antibodies or fragments thereof other than SYNAGIS® that immunospecifically bind to a RSV antigen. Preferably, a prophylactic agent is an agent which is known to be useful to, or has been or is currently being used to prevent or impede the onset, development, progression, and/or severity of a RSV infection or a symptom thereof.

As used herein, the term "prophylactically effective amount" refers to the amount of a liquid formulation of the invention which is sufficient to result in the prevention of the development, recurrence, onset or progression of a RSV infection. In a specific embodiment, a prophylactically effective amount of a prophylactic agent reduces one or more of the following steps of a RSV life cycle: the docking of the virus particle to a cell, the introduction of viral genetic information into a cell the expression of viral proteins, the production of new virus particles and the release of virus particles from a cell by at least 5%, preferably at least 10%, at least 15%, at least 20%, at least 25%, at least 30%, at least 35%, at least 40%, at least 45%, at least 50%, at least 55%, at least 60%, at least 65%, at least 70%, at least 75%, at least 80%, at least 85%, at least 90%, at least 95%, or at least 100%. In another specific embodiment, a prophylactically effective amount of a prophylactic agent reduces the replication, multiplication or spread of a virus by at least 5%, preferably at least 10%, at least 15%, at least 20%, at least 25%, at least 30%, at least 35%, at least 40%, at least 45%, at least 50%, at least 55%, at least 60%, at least 65%, at least 70%, at least 75%, at least 80%, at least 85%, at least 90%, at least 95%, or at least 100%.

As used herein, the term "RSV antigen" refers to a RSV protein, polypeptide or peptide to which an antibody immunospecifically binds.

As used herein, the term "saccharide" refers to a class of molecules that are polyhydric alcohols. Saccharides are commonly referred to as carbohydrates and may contain different amounts of sugar (saccharide) units, e.g., monosaccharides, dissacharides and polysaccharides.

The term "small molecule" and analogous terms include, but are not limited to, peptides, peptidomimetics, amino acids, amino acid analogues, polynucleotides, polynucleotide analogues, nucleotides, nucleotide analogues, organic or inorganic compounds (i.e., including heterorganic and/or ganometallic compounds) having a molecular weight less than about 10,000 grams per mole, organic or inorganic compounds having a molecular weight less than about 5,000 grams per mole, organic or inorganic compounds having a molecular weight less than about 1,000 grams per mole, organic or inorganic compounds having a molecular weight less than about 500 grams per mole, and salts, esters, and other pharmaceutically acceptable forms of such compounds.

As used herein, The terms "stability" and "stable" in the context of a liquid formulation comprising SYNAGIS® or an antigen-binding fragment thereof refer to the resistance of SYNAGIS® or an antigen-binding fragment thereof in the formulation to thermal and chemical unfolding, aggregation, degradation or fragmentation under given manufacture, preparation, transportation and storage conditions. The "stable" formulations of the invention retain biological activity equal to or more than 80%, 85%, 90%, 95%, 98%, 99%, or 99.5% under given manufacture, preparation, transportation and storage conditions. The stability of SYNAGIS® or an antigen-binding fragment thereof can be assessed by degrees of aggregation, degradation or fragmentation by methods known to those skilled in the art, including but not limited to reduced Capillary Gel Electrophoresis (rCGE), Sodium Dodecyl Sulfate Polyacrylamide Gel Electrophoresis (SDS-PAGE) and HPSEC, compared to a reference, that is, a commercially available lyophilized SYNAGIS® reconstituted to 100 mg/ml in 47 mM histidine/3 mM glycine buffer with 5.6% mannitol at pH 6.0. The reference regularly gives a single peak (>97% area) by HPSEC. The overall stability of a liquid formulation comprising SYNAGIS® or an antigen-binding fragment thereof that immunospecifically binds to a RSV antigen can be assessed by various immunological assays including, for example, ELISA and radioimmunoassay using the specific epitope of RSV.

As used herein, the term "SYNAGIS® standard reference" or analogous terms refer to commercially available lyophilized SYNAGIS®, as described in the Physicians' Desk Reference, $56^{th}$ edition, 2002. Reconstituted SYNAGIS®, may contain e.g., the following excipients: 47 mM histidine, 3.0 mM glycine and 5.6% manitol and the active ingredient, the antibody, at a concentration of 100 milligrams per ml solution.

The terms "subject" and "patient" are used interchangeably herein As used herein, the terms "subject" and "subjects" refer to an animal preferably a mammal including a non-primate (e.g., a cow, pig, horse, cat, dog, rat, and mouse) and a pie (e.g., a chimpanzee, a monkey such as a cynomolgous monkey, and a human), and more preferably a human.

As used herein, the term "substantially free of surfactant" refers to a formulation of SYNAGIS® or an antigen-binding fragment thereof said formulation containing less than 0.0005%, less than 0.0003%, or less than 0.0001% of surfactants and/or less than 0.0005%, less than 0.0003%, or less than 0.0001% of surfactant.

As used herein, the term "substantially free of inorganic salts" refers to a formulation of SYNAGIS® or an antigen-binding fragment thereof, said formulation containing less than 0.0005%, less than 0.0003%, or less than 0.0001% of inorganic salts.

As used herein, the term "surfactant" refers to organic substances having amphipathic structures; namely, they are composed of groups of opposing solubility tendencies, typically an oil-soluble hydrocarbon chain and a water-soluble ionic group. Surfactants can be classified, depending on the charge of the surface-active moiety, into anionic, cationic, and nonionic surfactants. Surfactants are often used as wetting, emulsifying, solubilizing, and dispersing agents for various pharmaceutical compositions and preparations of biological materials.

As used herein, the terms "therapeutic agent" and "therapeutic agents" refer to any agent(s) which can be used in the treatment, management or amelioration a RSV infection or one or more symptoms thereof. In certain embodiments, the term "therapeutic agent" refers to SYNAGIS® or an antigen-binding fragment thereof. In accordance with these embodiments, the antibody or antibody fragment may be a component of a liquid formulation of the invention. In certain other embodiments, the term "therapeutic agent" does not refer to SYNAGIS® or an antigen-binding fragment thereof. In yet other embodiments, the term "therapeutic agent" does not refer to antibodies or fragments thereof, other than SYNAGIS® that immunospecifically bind to a RSV antigen. Preferably, a therapeutic agent is an agent which is known to be useful for, or has been or is currently being used for the treatment, management or amelioration of a RSV infection or one or more symptoms thereof.

As used herein, the term "therapeutically effective amount" refers to the amount of a liquid formulation of the invention that reduces or ameliorates the progression, severity, and/or duration of a RSV infection, and/or ameliorates one or more symptoms associated with a RSV infection. With respect to the treatment of a RSV infection, a therapeutically effective amount refers to the amount of a therapeutic agent sufficient to reduce or inhibit the replication of a virus, inhibit or reduce the infection of cell with the virus, inhibit or reduce the production of the viral particles, inhibit or reduce the release of viral particles, inhibit or reduce the spread of the virus to other tissues or subjects, or ameliorate one or more symptoms associated with the infection. In a specific embodiment, a therapeutically effective amount of a therapeutic agent reduces one or more of the following steps of a RSV life cycle: the docking of the virus particle to a cell, the introduction of viral genetic information into a cell, the expression of viral proteins, the production of new virus particles and the release of virus particles from a cell by at least 5%, preferably at least 10%, at least 15%, at least 20%, at least 25%, at least 30%, at least 35%, at least 40%, at least 45%, at least 50%, at least 55%, at least 60%, at least 65%, at least 70%, at least 75%, at least 80%, at least 85%, at least 90%, at least 95%, or at least 100%. In another specific embodiment, a therapeutically effective amount of a therapeutic agent reduces the replication, multiplication or spread of a virus by at least 50%, preferably at least 10%, at least 15%, at least 20%, at least 25%, at least 30%, at least 35%, at least 40%, at least 45%, at least 50%, at least 55%, at least 60%, at least 65%, at least 70%, at least 75%, at least 80%, at least 85%, at least 90%, at least 95%, or at least 100%.

As used herein, the terms "therapies" and "therapy" can refer to any protocol(s), method(s) and/or agent(s) that can be used in the prevention, treatment, management or amelioration of a RSV infection or one or more symptoms thereof. In certain embodiments, the terms "therapy" and "therapies" refer to biological therapy, and/or other therapies useful for the treatment of a RSV infection known to medical personnel skilled.

As used herein, the terms "treat", "treating" and "treatment" refer to the reduction or amelioration of the progression, severity, and/or duration of a RSV infection and/or reduces or ameliorates one or more symptoms of a RSV infection. In specific embodiments, such terms refer to the reduction or inhibition of the replication of a respiratory syncytial virus (RSV), the inhibition or reduction in the spread of a respiratory syncytial virus (RSV) to other tissues or subjects, the inhibition or reduction of infection of a cell with a respiratory syncytial virus (RSV), or the amelioration of one or more symptoms associated with a respiratory syncytial virus (RSV) infection.

A used herein, a "protocol" includes dosing schedules and dosing regimens. The protocols herein are methods of use and include prophylactic and therapeutic protocols.

As used herein, the term "T cell receptor modulator" refers to an agent which modulates the phosphorylation of a T cell receptor, the activation of a signal transduction pathway associated with a T cell receptor and/or the expression of a particular protein such as a cytokine. Such an agent may directly or indirectly modulate the phosphorylation of a T cell receptor, the activation of a signal transduction pathway associated with a T cell receptor, and/or the expression of a particular protein such as a cytokine. Examples of T cell receptor modulators include, but are not limited to, peptides, polypeptides, proteins, fusion proteins and antibodies which immunospecifically bind to a T cell receptor or a fragment thereof. Further, examples of T cell receptor modulators include, but are not limited to, proteins, peptides, polypeptides (e.g., soluble T cell receptors), fusion proteins and antibodies that immunospecifically binds to a ligand for a T cell receptor or a fragment thereof.

As used herein, the term "very little to no loss of the biological activities" refers to antibody activities, including specific binding abilities of SYNAGIS® or an antigen-binding fragment as measured by various immunological assays, including, but not limited to ELISAs and radioimmunoassays. In one embodiment, SYNAGIS® or an antigen-binding fragment of the liquid formulations of the invention retain approximately 50%, preferably 55%, 60%, 65%, 70%, 75%, 80%, 85%, 90%, 95% or 98% of the ability to immunospecifically bind to a RSV antigen as compared to a reference antibody or antibody fragment as measured by an immunological assay known to one of skill in the art or described herein. For example, an ELISA based assay may be used to compare the ability of a liquid formulation of SYNAGIS® or an antigen-binding fragment thereof to immunospecifically bind to a RSV antigen to a SYNAGIS® reference standard. In this assay, plates are coated with a RSV antigen and the binding signal of a set concentration of a SYNAGIS® reference standard is compared to the binding signal of the same concentration of a test antibody or antibody fragment.

4. BRIEF DESCRIPTION OF THE FIGURES

FIG. 1 is a schematic diagram showing the outline for preparing purified SYNAGIS®.

5. DETAILED DESCRIPTION OF THE INVENTION

Figure 2:
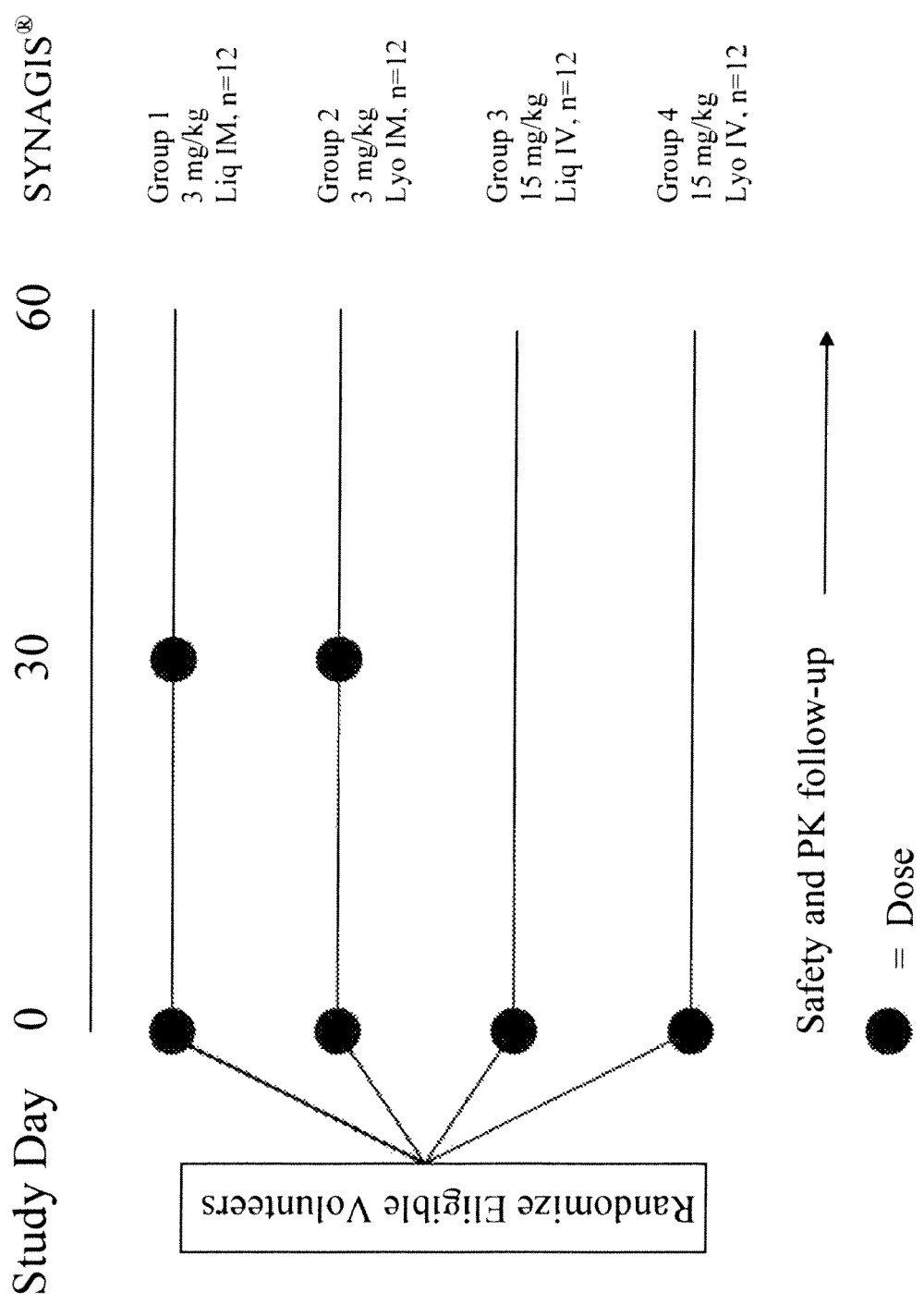
FIG. 2 shows the clinical study flow chart for comparing the liquid formulation of SYNAGIS® with the lyophilized formulation of SYNAGIS®.

The liquid formulations of the present invention provide a ready-to-use preparation of SYNAGIS® or an antigen-binding fragment thereof for administering to a subject without having to reconstitute the preparation accurately and aseptically and waiting for a period of time until the solution clarifies before administering the formulation to the subject. It simplifies the pure of administering the formulation to a subject for a healthcare professional. Furthermore, due to its high stability during the storage, the formulations of the present invention can contain SYNAGIS® or an antigen-binding fragment thereof at concentrations in the range of about 15 mg/ml to about 300 mg/ml without causing an adverse effect on the biological activity(ies) of SYNAGIS® or an antigen-binding fragment thereof due to protein aggregation and/or fragmentation during a prolonged storage. Such stability not only ensures the efficacy of SYNAGIS® or an antigen-binding fragment thereof but also reduces possible risks of causing adverse effects on a subject. In addition, the manufacturing process of the liquid formulations of the present invention is simplified and more efficient than the manufacturing process for the lyophilized version because all stages of the manufacturing of the liquid formulations are carried out in an aqueous solution, involving no drying process, such as lyophilization and freeze-drying. Accordingly, it is more cost effective as well.

5.1 SYNAGIS® Liquid Formulations

The liquid formulations of the present invention provide antibody formulations which are substantially free of surfactant, inorganic salts, and/or other excipients and yet exhibit high stability during long periods of storage. Id a specific embodiment, such antibody formulations are homogeneous. The formulations of the present invention comprise histidine at concentrations between 1 and 100 mM and SYNAGIS® or an antigen-binding fragment thereof at concentrations of about 15 mg/ml to about 300 mg/ml. In one embodiment, the formulations of the invention do not comprise other ingredients except for water or suitable solvents. In another specific embodiment, a modified form of SYNAGIS® antibody or an antigen-binding fragment thereof having improved half-life and/or affinity is used in the liquid formulations of the invention.

The concentration of SYNAGIS® or an antigen-binding fragment thereof which is included in the liquid formulations of the invention, is at least 15 mg/ml at least 20 mg/ml at least 25 mg/ml, at least 30 mg/ml, at least 35 mg/ml, at least 40 mg/ml, at least 45 mg/ml, at least 50 mg/ml, at least 55 mg/ml, at least 60 mg/ml, at least 65 mg/ml, at least 70 mg/ml, at least 75 mg/ml, at least 80 mg/ml, at least 85 mg/ml, at least 90 mg/ml, at least 95 mg/ml, at least 100 mg/ml, at least 105 mg/ml, at least 110 mg/ml, at least 115 mg/ml, at least 120 mg/ml, at least 125 mg/ml, at least 130 mg/ml, at least 135 mg/ml, at least 140 mg/ml, at least 150 mg/ml, at least 200 mg/ml, at least 250 mg/ml, or at least 300 mg/ml.

The concentration of histidine which is included in the liquid formulations of the invention ranges from about 1 mM to about 100 mM, about 10 mM to about 50 mM, about 20 mM to about 30 mM, or about 23 mM to about 27 mM, and is most preferably about 25 mM. Histidine can be in the form of l-histidine, D-histidine, or a mixture thereof, but L-histidine is the most preferable. Histidine can be also in the form of hydrates. Histidine may be used in a form of pharmaceutically acceptable salt, such as hydrochloride (e.g., monohydrochloride and dihydrochloride), hydrobromide, sulfate, acetate, etc. The purity of histidine should be at least 98%, preferably at least 99%, and most preferably at least 99.5%.

The pH of the formulation should not be equal to the isoelectric point of the particular antibody to be used in the formulation (e.g., the isoelectric point of SYNAGIS® ranges from 8.65 to 9.43) and may range from about 5.0 to about 7, preferably about 5.5 to about 6.5, more preferably about 5.8 to about 6.2, and most preferably about 6.0.

In addition to histidine and SYNAGIS® or an antigen-binding fragment thereof the formulations of the present invention may further comprise glycine at a concentration of less than 150 mM, less than 100 mM, less than 50 mM, less than 3.0 mM, less than 2.0 mM, or less than 1.8 mM, and most preferably 1.6 mM. The amount of glycine in the formulation should not cause a significant buffering effect so that antibody precipitation at its isoelectric point can be avoided. Glycine may be also used in a form of a pharmaceutically acceptable salt, such as hydrochloride, hydrobromide, sulfate, acetate, etc. The purity of glycine should be at least 98%, preferably at least 99%, and most preferably 99.5%. In a specific embodiment, glycine is not included in the liquid formulations of the present invention.

Optionally, the formulations of the present invention may further comprise other excipients, such as saccharides (e.g., sucrose, mannose, trehalose, etc.) and polyols (e.g., mannitol, sorbitol, etc.). In one embodiment, the other excipient is a saccharide. In a specific embodiment, the saccharide is sucrose, which is at a concentration range between about 1% and about 20%, preferably about 5% and about 15%, more preferably about 8% and 10%. In another embodiment, the other excipient is a polyol. Preferably, however, the liquid formulations of the present invention do not contain mannitol. In a specific embodiment, the polyol is polysorbate (e.g., Tween 20), which is at a concentration range between about 0.001% and about 1%, preferably, about 0.01 to about 0.1.

The liquid formulations of the present invention exhibit stability at the temper ranges of 38° C.-42° C. for at least 60 days and, in some embodiments, not more than 120 days, of 20° C.-24° C. for at least 1 year, of 2° C.-8° C. (in particular, at 4° C.) for at least 3 years, at least 4 years, or at least 5 years and at −20° C. for at least 3 years at least 4 years, or at least 5 years, as assessed by high performance size exclusion chromatography (HPSEC). Namely, the liquid formulations of the present invention have low to undetectable levels of aggregation and/or fragmentation, as defined herein, after the storage for the defined periods as set forth above. Preferably, no more than 5%, no more than 4%, no more than 3%, no more than 2%, no more than 1%, and most preferably no more than 0.5%, of SYNAGIS® or an antigen-binding fragment thereof forms an aggregate as measured by HPSEC, after the storage for the defined periods as set forth above. Furthermore, liquid formulations of the present invention exhibit almost no loss in biological activity(ies) of SYNAGIS® or an antigen-binding fragment thereof during the prolonged storage under the condition described above, as assessed by various immunological assays including, for example, enzyme-linked immunosorbent assay (ELISA) and radioimmunoassay to measure the RSV antigen-binding ability of SYNAGIS® or an antigen-binding fragment thereof, or, for example, by a C3a/C4a assay to measure the complement activating ability of SYNAGIS® or an antigen-binding fragment thereof. The liquid formulations of the present invention retain after the storage for the above-defined periods more than 80%, more than 85%, more than 90%, more than 95%, more than 98%, more than 99%, or more than 99.5% of the initial biological activity (ies) prior to the storage.

The liquid formulations of the present invention can be prepared as unit dosage forms. For example, a unit dosage per vial may contain 1 ml, 2 ml, 3 ml, 4 ml, 5 ml, 6 ml, 7 ml, 8 ml, 9 ml, 10 ml, 15 ml, or 20 ml of different concentrations of SYNAGIS® or an antigen-binding fragment thereof ranging from about 15 mg/ml to about 300 mg/ml concentration of SYNAGIS® or an antigen-binding fragment thereof which immunospecifically binds to a RSV. If necessary, these preparations can be adjusted to a desired concentration by adding a sterile diluent to each vial.

5.1.1 SYNAGIS®

The invention relates to liquid formulations comprising SYNAGIS® or an antigen-binding fragment thereof. In a preferred embodiments, the invention provides liquid formulations of SYNAGIS® a humanized monoclonal antibody which neutralizes a broad range of RSV isolates. The amino acid sequence of SYNAGIS® is disclosed, e.g., in Johnson et al., 1997, *J. Infectious Disease* 176:1215-1224, and U.S. Pat. No. 5,824,307, and its $V_H$CDRs and $V_L$CDRs are shown in Table 1, infra. The properties and uses of SYNAGIS® are also disclosed in, e.g., other applications, see, e.g., U.S. patent application Ser. No. 09/724,396 filed Nov. 28, 2000; U.S. patent application Ser. No. 09/996,265 filed Nov. 28, 2001 and U.S. patent application Ser. No. 10/403,180 filed Mar. 31, 2003, all of which are incorporated herein by reference.

TABLE 1

CDR Sequences of SYNAGIS ®

| CDR | Sequence | SEQ ID NO: |
|---|---|---|
| VH1 | TSGMSVG | 1 |
| VH2 | DIWWDDKKDYNPSLKS | 2 |
| VH3 | SMITNWYFDV | 3 |
| VL1 | KCOLSVGYMH | 4 |
| VL2 | DTSKLAS | 5 |
| VL3 | FQGSGYPFT | 6 |

In addition, the present invention also encompasses stable liquid formulations of modified forms of SYNAGIS® or an antigen-binding fragment thereof that have improved half-lives. In particular, the present invention encompasses a modified form of SYNAGIS® or an antigen-binding fragment thereof which has a half-life in a subject, preferably a human, of greater than 3 days, greater than 7 days, greater than 10 days, preferably greater than 15 days, greater than 25 days, greater than 30 days, greater than 35 days, greater than 40 days, greater than 45 days, greater than 2 months, greater than 3 months, greater than 4 months, or greater than 5 months. By prolonging the half-lives of SYNAGIS® and antigen-binding fragments thereof, it is possible to reduce the amount and/or frequency of dosing of the antibody or antigen-binding fragment.

To prolong the serum circulation of an antibody in vivo, various techniques can be used. For example, inert polymer molecules, such as high molecular weight polyethyleneglycol (PEG), can be attached to an antibody with or without a multifunctional linker either through site-specific conjugation of the PEG to the N- or C-terminus of the antibody or via epsilon-amino groups present on lysine residues. Linear or branched polymer derivatization that results in minimal loss of biological activity can be used. The degree of conjugation can be closely monitored by SDS-PAGE and mass spectrometry to ensure proper conjugation of PEG molecules to the antibodies. Unreacted PEG can be separated from antibody-PEG conjugates by size-exclusion or by ion-exchange chromatography. PEG-derivatized antibodies can be tested for binding activity as well as for in vivo efficacy using methods known to those of skilled in the art for example, by immunoassays described herein.

An antibody having an increased half-life in vivo can also be generated by introducing one or more amino acid modifications (i.e., substitutions, insertions or deletions) into an IgG constant domain, or FcRn binding fragment thereof (preferably a Fc or hinge Fc domain fragment). Sec, e.g., International Publication No. WO 9823289; International Publication No. WO 97/34631; and U.S. Pat. No. 6,277,375, each of which is incorporated herein by reference in its entirety. SYNAGIS® and antigen-binding fragments thereof with improved in vivo half-lives and methods for preparing them are disclosed in International Application WO 02/060919, filed Dec. 12, 2001, and U.S. patent application Ser. No. 10/020,354, filed Dec. 12, 2001, both entitled "Molecules with Extended Half-Lives, Compositions and Uses" and by L. Johnson et al. which are hereby incorporated by reference in their entireties.

Further, an antibody can be conjugated to albumin in order to make the antibody or an antigen-binding fragment thereof more stable in vivo or have a longer half life in vivo. The techniques are well known in the art, see e.g., International Publication Nos. WO 93/15199, WO 93/15200, and WO 01/77137; and European Patent No. EP 413, 622, all of which are incorporated herein by reference.

The invention further comprises liquid formulations of SYNAGIS® or antigen-binding fragments thereof that have been modified, for example, by glycosylation, acetylation, pegylatin, phosphorylation, amidation, derivatization by known protecting/blocking groups, proteolytic cleavage, linkage to a cellular ligand or other protein, etc., and retain RSV antigen-binding activity.

5.1.2 Antibody Conjugates

The present invention encompasses the use of liquid formulations of SYNAGIS® or an antigen-binding fragment thereof (including modified forms that have increased in vivo half-lives) that conjugated to one or more moieties, including but not limited to, peptides, polypeptides, proteins, fusion proteins, nucleic acid molecules, small molecules, mimetic agents, synthetic drugs, inorganic molecules, and organic molecules.

The preset invention encompasses the use of liquid formulations of SYNAGIS® recombinantly fused or chemically conjugated (including both covalent and non-covalent conjugations) to a heterologous protein or polypeptide (or antigen-binding fragment, preferably to a polypeptide of at least 10, at least 20, at least 30, at least 40, at least 50, at least 60, at least 70, at least 80, at least 90 or at least 100 amino acids) to generated fusion proteins. The fusion does not necessarily need to be direct, but may occur through linker sequences. For example, an antibody may be used to target a heterologous polypeptide to a particular cell type, either in vitro or in vivo, by fusing or conjugating the antibody to another antibody specific for particular cell surface receptors. An antibody fused or conjugated to a heterologous polypeptide may also be used in in vitro immunoassays and purification methods using methods known in the arts. See e.g., International publication No. WO 93/21232; European Patent No. EP 439,095; Naramura et al., 1994, Immunol. Lett. 39:91-99; U.S. Pat. No. 5,474,981; Gillies et al., 1992, PNAS 89:1428-1432; and Fell et al., 1991, J. Immunol. 146:2446-2452, which are incorporated by reference in their entireties.

The present invention further includes compositions comprising a heterologous protein, peptide or polypeptide fused or conjugated to an antigen-binding fragment of SYNAGIS®. For example, a heterologous polypeptides may be fused or conjugated to a Fab fragment, Fd fragment, Fv fragment, or F(ab)$_2$ fragment. Methods for fusing or conjugating a polypeptide to antibody portion are known in the art. See, e.g., U.S. Pat. Nos. 5,336,603, 5,622,929, 5,359,046, 5,349,053, 5,447,851, and 5,112,946; European Patent Nos. EP 307,434 and EP 367,166; International publication Nos. WO 96/04388 and WO 91/06570; Ashkenazi et al. 1991, Proc. Natl. Acad. Sci. USA 88: 10535-10539; Zheng et al., 1995, J. Immunol. 154:5590-5600; and Vil et al., 1992, Proc. Natl. Acad. Sci. USA 89:11337-11341 (all references are incorporated herein by reference in their entireties).

Additional fusion proteins may be generated through the techniques of gene-shuffling, motif-shuffling, exon-shuffling, and/or codon-shuffling (collectively referred to as "DNA shuffling"). DNA shuffling may be employed to alter the activities of SYNAGIS® or fragments thereof (e.g., an antibody or an antigen-binding fragment thereof with higher affinities and lower dissociation rates). See, generally, U.S. Pat. Nos. 5,605,793; 5,811,238; 5,830,721; 5,834,252; and 5,837,458, and Patten et al., 1997, Curr. Opinion Biotechnol. 8:724-33; Harayama, 1998, Trends Biotechnol. 16(2):76-82; Hansson et al., 1999, J. Mol. Biol. 287:265-76; and Lorenzo and Blasco, 1998, Biotechniques 24(2):308-313 (each of these patents and publications are hereby incorporated by reference in its entirety). SYNAGIS® or an antigen-binding fragment thereof, or the nucleic acid encoding SYNAGIS® or an antigen-binding fragment thereof may be altered by being subjected to random mutagenesis by error-prone PCR, random nucleotide insertion or other methods prior to recombination SYNAGIS® or an antigen-binding fragment thereof may be recombined with one or more components, motif sections, parts, domains, fragments, etc. of one or more heterologous molecules.

Moreover, SYNAGIS® or an antigen-binding fragment thereof can be fused to a marker sequence, such as a peptide to facilitate purification. In preferred embodiments, the marker amino acid sequence is a hexa-histidine peptide, such as the tag provided in a pQE vector (QIAGEN, Inc., 9259 Eton Avenue, Chatsworth, Calif., 91311), among others, many of which are commercially available. As described in Gentz et al., 1989, Proc. Natl. Acad. Sci. USA 86:821-824, for instance, hexa-histidine provides for convenient purification of the fusion protein. Other peptide tags useful for purification include, but are not limited to, the hemagglutinin "HA" tag, which corresponds to an epitope derived from the influenza hemagglutinin protein (Wilson et al., 1984, Cell 37:767) and the "flag" tag.

The present invention also encompasses the liquid formulations of SYNAGIS® or an antigen-binding fragment thereof conjugated to a diagnostic or detectable agent or any other molecule for which serum half-life is desired to be increased. Such an antibody can be useful for monitoring or prognosing the development or progression of a RSV infection as part of a clinical testing procedure, such as determining the efficacy of a particular therapy. Such diagnosis and detection can be accomplished by coupling SYNAGIS® or an antigen-binding fragment thereof to a detectable substance including, but not limited to, various enzymes, such as but not limited to, horseradish peroxidase, alkaline phosphatase, beta-galactosidase, or acetylcholinesterase; prosthetic groups, such as but not limited to, streptavidin/biotin and avidin/biotin; fluorescent materials, such as but not limited to, umbelliferone, fluorescein, fluorescein isothiocynate, rhodamine, dichlorotriazinylamine fluorescein, dansyl chloride or phycoerythrin; luminescent materials, such as but not limited to, luminol; bioluminescent materials, such as but not limited to, luciferase, luciferin, and aequorin; radioactive materials, such as but not limited to iodine ($^{131}$I, $^{125}$I, $^{123}$I, $^{121}$I), carbon ($^{14}$C), sulfur ($^{35}$S), tritium ($^{3}$H), indium ($^{115}$In, $^{113}$In, $^{112}$In, $^{111}$In), and technetium ($^{99}$Tc), thallium ($^{201}$Ti), gallium ($^{68}$Ga, $^{67}$Ga), palladium ($^{103}$Pd), molybdenum ($^{99}$Mo), xenon ($^{133}$Xe), fluorine ($^{18}$F), $^{153}$Sm, $^{177}$Lu, $^{159}$Gd, $^{149}$Pm, $^{140}$La, $^{175}$Yb, $^{166}$Ho, $^{90}$Y, $^{47}$Sc, $^{186}$Re, $^{188}$Re, $^{142}$Pr, $^{105}$Rh, $^{97}$Ru, $^{68}$Ge, $^{57}$Co, $^{65}$Zn, $^{85}$Sr, $^{32}$P, $^{153}$Gd, $^{169}$Yb, $^{51}$Cr, $^{54}$Mn, $^{75}$Se, $^{113}$Sn, and $^{117}$Tin; positron emitting metals using various positron emission tomographies, nonradioactive paramagnetic metal ions, and molecules that are radiolabelled or conjugated to specific radioisotopes. The detectable substance may be coupled or conjugated either directly to SYNAGIS® or an antigen-binding fragment thereof or indirectly, through an intermediate (such as, for example, a linker known in the art) using techniques known in the art. See, e.g., U.S. Pat. No. 4,741,900 for metal ions which can be conjugated to antibodies for use as a diagnostics according to the present invention.

The present invention further encompasses uses of SYNAGIS® or an antigen binding fragment thereof conjugated to a therapeutic moiety. An antibody or antigen-binding fragment may be conjugated to a therapeutic moiety such as a cytotoxin, e.g., a cytostatic or cytocidal agent, a therapeutic agent or a radioactive metal ion, e.g., alpha emitters. A cytotoxin or cytotoxic agent includes any agent that is detrimental to cells. Examples include paclitaxel, cytochalasin B, gramicidin D, ethidium bromide, emetine, mitomycin, etoposide, tenoposide, vincristine, vinblastine, colchicin, doxorubicin, daunorubicin, dihydroxy anthracin dione, mitoxantrone, mithramycin, actinomycin D, 1-dehydrotestosterone, glucocorticoids, procaine, tetracaine, lidocaine, propranolol, and puromycin and analogs or homologs thereof. Therapeutic moieties include, but are not limited to, antimetabolites (e.g., methotrexate, 6-mercaptopurine, 6-thioguanine, cytarabine, 5-fluorouracil decarbazine), alkylating agents (e.g., mechlorethamine, thioepa chlorambucil, melphalan, carmustine (BCNU) and lomustine (CCNU)), cyclothosphamide, busulfan, dibromomannitol, streptozotocin, mitomycin C, and cis-dichlorodiamine platinum (II) (DDP) cisplatin)); anthracyclines (e.g., daunorubicin (formerly daunomycin) and doxorubicin); antibiotics (e.g., dactinomycin (formerly actinomycin), bleomycin, mithramycin, and anthramycin (AMC)); Auristatin molecules (e.g., auristatin PHE, bryostatin 1, solastatin 10, see Woyke et al., Antimicrob. Agents Chemother. 46:3802-8 (2002), Woyke et al., Antimicrob. Agents Chemother. 45:3580-4 (2001), Mohammad et al., Anticancer Drugs 12:73540 (2001), Wall et al., Biochem. Biophys. Res. Commun. 266:76-80 (1999), Mohammad et al., Int. J. Oncol. 15:367-72 (1999), all of which are incorporated herein by reference); anti-mitotic agents (e.g., vincristine and vinblastine); hormones (e.g., glucocorticoids, progestatins, androgens, and estrogens); DNA repair enzyme inhibitors (e.g., etoposide or topotecan); kinase inhibitors (e.g., compound ST1571, imatinib mesylate (Kantarjian et al., Clin Cancer Res. 8(7):2167 76 (2002)), and those compounds disclosed in U.S. Pat. Nos. 6,245,759, 6,399,633, 6,383,790, 6,335,156, 6,271,242, 6,242,196, 6,218,410, 6,218,372, 6,057,300, 6,034,053, 5,985,877, 5,958,769, 5,925,376, 5,922,844, 5,911,995, 5,872,223, 5,863,904, 5,840,745, 5,728,868, 5,648,239, and 5,587,459); farnesyl transferase inhibitors (e.g., R115777, BMS 214662, and those disclosed by, for example, U.S. Pat. Nos. 6,458,935, 6,451,812, 6,440,974, 6,436,960, 6,432,959, 6,420,387, 6,414,145, 6,410,541, 6,410,539, 6,403,581, 6,399,615, 6,387,905, 6,372,747, 6,369,034, 6,362,188, 6,342,765, 6,342,487, 6,300,501, 6,268,363, 6,265,422, 6,248,756, 6,239,140, 6,232,338, 6,228,865, 6,228,856, 6,225,322, 6,218,406, 6,211,193, 6,187,786, 6,169,096, 6,159,984, 6,143,766, 6,133,303, 6,127,366, 6,124,465, 6,124,295, 6,103,723, 6,093,737, 6,090,948, 6,080,870, 6,077,853, 6,071,935, 6,066,738, 6,063,930, 6,054,466, 6,051,582, 6,051,574, and 6,040,305); topoisomerase inhibitors (e.g., camptothecin, irinoteca SN 38, topotecan, 9 aminocamptothecin, GG 211 (GI 147211), DX 8951f; IST 622, rubitecan, pyrazoloacridine, XR 5000, saintopin, UCE6, UCE1022, TAN 1518A, TAN 1518B, KT6006, KT6528, ED 110, NB 506, ED 110, NB 506, rebeccamycin, and bulgarein); DNA minor groove binders such as Hoescht dye 33342 and Hoechst dye 33258; nitidine; fagaronine; epiberberine; coralyne; beta lapachone; BC 41; and pharmaceutically acceptable salts, solvates, clathrates, and prodrugs thereof (See, e.g., Rothenberg, M. L., Annals of Oncology 8:837 855 (1997); and Moreau et al., J. Med. Chem. 41:1631 1640 (1998)). Therapeutic moieties may also be antisense oligonucleotides (e.g., those disclosed in the U.S. Pat. Nos. 6,277,832, 5,998, 596, 5,885,834, 5,734,033, and 5,618,709); immunomodulators (e.g., antibodies and cytokines); antibodies (e.g., rituximab (Rituxan®), calichemycin (Mylotarg®), ibritumomab tiuxetan (Zevalin®), and tositumomab (Bexxar®)); and adnosine deaminase inhibitors (e.g., Fludarabine phosphate and 2 Chlorodeoxyadenosine).

Further, an antibody or an antigen-binding fragment thereof may be conjugated to a therapeutic moiety or drug moiety that modifies a given biological response. Therapeutic moiety or drug moieties are not to be construed as limited to classical chemical therapeutic agents. For example, the drug moiety may be a protein or polypeptide possessing a desired biological activity. Such proteins may include, for example, a toxin such as abrin, ricin A, pseudomonas exotoxin, cholera toxin, or diphtheria toxin; a protein such as tumor necrosis factor, α-interferon, β-interferon, nerve growth factor, platelet derived growth factor, tissue plasminogen activator, an apoptotic agent, e.g., TNF-α, TNF-β, AIM I (see, International publication No. WO 97/33899), AIM II (see, International Publication No. WO 97/34911), Fas Ligand (Takahashi et al., 1994, J. Immunol., 6:1567-1574), and VEGF (see, International publication No. WO 99/23105); or, a biological response modifier such as, for example, a lymphokine (e.g., interleukin-1 ("IL-1"), interleukin-2 ("IL-2"), interleukin-4 ("IL-4"), interleukin-6 ("IL-6"), interleukin-9 (IL-9), interleukin-10 (IL-10), interleukin-IL-12 (IL-12), interferon-α, β, γ, granulocyte macrophage colony stimulating factor ("GM-CSF"), and granulocyte colony stimulating factor ("G-CSF")), or a growth factor (e.g., growth hormone ("GH")).

Moreover, an antibody can be conjugated to therapeutic moieties such as a radioactive metal ion, e.g., alpha-emitters such as $^{213}$Bi or macrocyclic chelators useful for conjugating radiometal ions, including but not limited to, $^{131}$I, $^{131}$LU, $^{131}$Y, $^{131}$Ho, $^{131}$Sm, to polypeptides. In certain embodiments, the macrocyclic chelator is 1,4,7,10-tetraazacyclododecane-N,N',N'',N'''-tetraacetic acid (DOTA) which can be attached to the antibody via a linker molecule. Such linker molecules are commonly known in the art and described in Denardo e al., 1998, Clin Cancer Res. 4(10):2483-90; Peterson et al., 1999, Bioconjug. Chem. 10(4):553-7; and Zimmerman et al., 1999, Nucl. Med. Biol. 26(8):943-50, each incorporated by reference in their entireties.

Techniques for conjugating therapeutic moieties to antibodies are well known, see, e.g., Amon et al., "Monoclonal Antibodies For Immunotargeting Of Drugs In Cancer Therapy", in Monoclonal Antibodies And Cancer Therapy, Reisfeld et al. (eds.), pp. 243-56 (Alan R Liss, Inc. 1985); Hellstrom et al., "Antibodies For Drug Delivery", in Controlled Drug Delivery (2nd Ed.), Robinson et al. (eds.), pp. 623-53 (Marcel Dekker, Inc. 1987); Thorpe, "Antibody Carriers Of Cytotoxic Agents In Cancer Therapy A Review", in Monoclonal Antibodies 84: Biological And Clinical Applications, Pinchera et al. (eds.), pp. 475-506 (1985); "Analysis, Results, And Future Prospective Of The Therapeutic Use Of Radiolabeled Antibody In Cancer Therapy", in Monoclonal Antibodies For Cancer Detection And Therapy, Baldwin et al. (eds.), pp. 303-16 (Academic Press 1985), and Thorpe et al., 1982, Immunol. Rev. 62:119-58.

Alternatively, SYNAGIS® or an antigen-binding fragment thereof can be conjugated to a second antibody to form an antibody heteroconjugate as described by Segal in U.S. Pat. No. 4,676,980, which is incorporated herein by reference in its entirety.

SYNAGIS® or an antigen-binding fragment thereof may also be attached to solid supports, which are particularly useful for immunoassays or purification of the target antigen. Such solid supports include, but are not limited to, glass, cellulose, polyacrylamide, nylon, polystyrene, polyvinyl chloride or polypropylene.

The therapeutic moiety or drug conjugated to SYNAGIS® or an antigen-binding fragment thereof should be chosen to achieve the desired prophylactic or therapeutic effect(s) for a RSV infection in a subject. A clinician or other medical professional should consider the following when deciding on which therapeutic moiety or drug to conjugate to SYNAGIS® or an antigen-binding fragment thereof: the severity of the infection, and the condition of the subject.

SYNAGIS® or an antigen-binding fragment thereof with or without a therapeutic moiety conjugated to it, can be used as a therapeutic.

5.2 Method of Preparing the Antibody Formulations

The present invention provides methods for preparing liquid formulations of SYNAGIS® or an antigen-binding fragment thereof. FIG. 1 is a schematic diagram showing the outline for preparing purified SYNAGIS®. The methods for preparing liquid formulations of the present invention comprise: purifying the antibody from conditioned medium (either single lots or pooled lots of medium) and concentrating a fraction containing the purified SYNAGIS® to a final antibody concentration of from about 15 mg/ml, about 20 mg/ml, about 30 mg/ml, about 40 mg/ml, about 50 mg/ml, about 60 mg/ml, about 70 mg/ml, about 80 mg/ml, about 90 mg/ml, about 100 mg/ml, about 150 mg/ml, about 200 mg/ml, about 250 mg/ml, or about 300 mg/ml using a semipermeable membrane with an appropriate molecular weight (MW) cutoff (e.g., 30 kD cutoff for whole antibody molecules and F(ab')$_2$ fragments; and 10 kD cutoff for antibody fragments, such as Fab fragments) and diafiltrating the concentrated antibody fraction into the formulation buffer using the same membrane. The formulation buffer of the present invention comprises histidine at a concentration from about 1 mM to about 100 mM, about 10 mM to about 50 mM, about 20 mM to about 30 mM, or about 23 mM to about 27 mM, and is most preferably about 25 mM. The formulations may further comprise glycine at a concentration of less than 100 mM, less than 50 mM, less than 3.0 mM, less than 2.0 mM, or less than 1.8 mM, and most preferably of 1.6 mM. The amount of glycine in the formulation should not cause a significant buffering in order to avoid antibody precipitation at its isoelectric point. The pH of the formulation may range from about 5.0 to about 7.0, preferably about 5.5 to about 6.5, more preferably about 3.8 to about 6.2, and most preferably about 6.0. To obtain an appropriate pH for a particular antibody, it is preferable that histidine (and glycine, if added) is first dissolved in water to obtain a buffer solution with higher pH than the desired pH and then the pH is brought down to the desired level by adding HCl. This way, the formation of inorganic salts (e.g., formation of NaCl when, for example, histidine hydrochloride is used as histidine and pH is raised to a desired level by adding NaOH) can be avoided.

The liquid formulations of the present invention can be prepared as unit dosage forms by preparing a vial containing an aliquot of the liquid formulation for a one-time use. For example, a unit dosage per vial may contain 1 ml, 2 ml, 3 ml, 4 ml, 5 ml, 6 ml, 7 ml, 8 ml, 9 ml, 10 ml, 15 ml, or 20 ml of different concentrations of SYNAGIS® or an antigen-binding fragment thereof ranging from about 15 mg/ml to about 300 mg/ml concentration of SYNAGIS® or an antigen-binding fragment thereof which immunospecifically binds to a RSV. If necessary, these preparations can be adjusted to a desired concentration by adding a sterile diluent to each vial.

The liquid formulations of the present invention may be sterilized by various sterilization methods, including sterile filtration, radiation, etc. In a most preferred embodiment, the diafiltrated antibody formulation is filter-sterilized with a presterilized 0.2 or 0.22-micron filter. Sterilized liquid formulations of the present invention may be administered to a subject to prevent, treat, manage or ameliorate a RSV infection or one or more symptoms thereof.

Although the invention is directed to liquid non-lyophilized formulations, it should be noted for the purpose of equivalents that the formulations of the invention may be lyophilized if desired. Thus, the invention encompasses lyophilized forms of the formulations of the invention although such lyophilized formulations are not necessary and thus not preferred.

5.3 Methods of Preparing SYNAGIS®

SYNAGIS® and an antigen-binding fragment thereof contained in the liquid formulations of the present invention can be prepared by any method known in the art for the synthesis of antibodies, in particular, by chemical synthesis or, preferably, by recombinant expression techniques.

The nucleotide sequence encoding the heavy and light chain variable domains of SYNAGIS® may be obtained from, for example, co-pending application Ser. No. 09/724,396, filed Nov. 28, 2000 and Ser. No. 09/996,265, filed Nov. 28, 2001, both by Young et al., and both of which are incorporated by reference herein in its entirety. See also, U.S. Pat. No. 5,824,307 by Johnson et al. In certain embodiments, a nucleic acid encoding SYNAGIS® or an antigen-binding fragment thereof may be chemically synthesized or assembled from oligonucleotides as well known in the art, and then amplified by PCR, cloning or other method known in the art.

Recombinant expression of an antibody (such as SYNAGIS® requires construction of an expression vector containing a nucleotide sequence that encodes the antibody. Once a nucleotide sequence encoding an antibody molecule or a heavy or light chain of an antibody, or an antigen-binding fragment thereof has been obtained, the vector for the production of the antibody molecule may be produced by recombinant DNA technology using techniques well known in the art as discussed in the previous sections. Methods which are well known to those skilled in the art can be used to construct expression vector containing antibody coding sequences and appropriate transcriptional and translational control signals. These methods include, for example, in vitro recombinant DNA techniques, synthetic techniques, and in vivo genetic recombination. The nucleotide sequence encoding the heavy-chain variable region, light-chain variable region, both the heavy-chain and light-chain variable regions, an epitope-binding fragment of the heavy- and/or light-chain variable region, or one or more complementarity determining regions (CDRs) of an antibody may be cloned into such a vector for expression. Thus-prepared expression vector can be then introduced into appropriate host cells for the expression of the antibody. Accordingly, the invention includes host cells containing a polynucleotide encoding SYNAGIS® or an antigen-binding fragment thereof.

The host cell may be co-transfected with two expression vectors of the invention, the first vector encoding a heavy chain derived polypeptide and the second vector encoding a light chain derived polypeptide. The two vectors may contain identical selectable markers which enable equal expression of heavy and light chain polypeptides or different selectable markers to ensure maintenance of both plasmids. Alternatively, a single vector may be used which encodes, and is capable of expressing, both heavy and light chain polypeptides. In such situations, the light chain should be placed before the heavy chain to avoid an excess of toxic free heavy chain (Proudfoot, Nature, 322:52, 1986; and Kohler, Proc. Natl. Acad. Sci. USA, 77:2 197, 1980). The coding sequences for the heavy and light chains may comprise cDNA or genomic DNA.

For long-term, high-yield production of recombinant antibodies, stable expression is preferred. For example, cell lines which stably express the antibody molecule may be engineered. Rather than using expression vectors which contain viral origins of replication, host cells can be transformed with DNA controlled by appropriate expression control elements (e.g., promoter, enhancer, sequences, transcription terminators, polyadenylation sites, etc.), and a selectable marker. Following the introduction of the foreign DNA, engineered cells may be allowed to grow for 1-2 days in an enriched media, and then are switched to a selective media. The selectable marker in the recombinant plasmid confers resistance to the selection and allows cells to stably integrate the plasmid into their chromosomes and grow to form foci which in turn can be cloned and expanded into cell lines. This method may advantageously be used to engineer cell lines which express the antibody molecule. Such engineered cell lines may be particularly useful in screening and evaluation of compositions that interact directly or indirectly with the antibody molecule.

A number of selection systems may be used, including but not limited to, the herpes simplex virus thymidine kinase (Wigler et al., Cell, 11:223, 1977), hypoxanthineguanine phosphoribosyltransferase (Szybalska & Szybalska, Proc. Natl. Acad. Sci. USA, 48:202, 1992), and adenine phosphoribosyltransferase (Lowy et al., Cell, 22:8-17, 1980) genes can be employed in $tk^-$, $hgprt^-$ or $aprt^-$ cells, respectively. Also, antimetabolite resistance can be used as the basis of selection for the following genes: dhfr, which confers resistance to methotrexate (Wigler et al., Natl. Acad. Sci. USA, 77:357, 1980 and O'Hare et al., Proc. Natl. Acad. Sci. USA, 78:1527, 1981); gpt, which confers resistance to mycophenolic acid (Mulligan & Berg, Proc. Natl. Acad. Sci. USA, 78:2072, 1981); neo, which confers resistance to the aminoglycoside G-418 (Wu and Wu, Biotherapy, 3:87-95, 1991; Tolstoshev, Ann. Rev. Pharmacol. Toxicol., 32:573-596, 1993; Mulligan, Science, 260:926-932, 1993; and Morgan and Anderson, Ann. Rev. Biochem., 62: 191-217, 1993; and May, TIB TECH, 11(5):155-215, 1993); and hygro, which confers resistance to hygromycin (Santerre et al, Gene, 30:147, 1984). Methods commonly known in the art of recombinant DNA technology may be routinely applied to select the desired recombinant clone, and such methods are described, for example, in Ausubel et al (eds.), 1993, Current Protocols in Molecular Biology, John Wiley & Sons, NY; Kriegler, 1990, Gene Transfer and Expression, A Laboratory Manual, Stockton Press, NY; in Chapters 12 and 13, Dracopoli et al. (eds), 1994, Current Protocols in Human Genetics, John Wiley & Sons, NY; and Colberre-Garapin et al., J. Mol. Biol., 150:1, 1981, which are incorporated by reference herein in their entireties.

The expression levels of an antibody molecule can be increased by vector amplification (for a review, see Bebbington and Hentschel, 1987, The use of vectors based on gene amplification for the expression of cloned genes in mammalian cells in DNA cloning, Vol. 3. Academic Press, New York). When a marker in the vector system expressing antibody is amplifiable, increasing in the level of inhibitor present in culture of host cell will increase the number of copies of the marker gene. Since the amplified region is associated with the antibody gene, production of the antibody will also increase (Crouse et al., Mol., Cell. Biol., 3:257, 1983).

Once an antibody molecule of the invention has been produced by recombinant expression, it may be purified by any method known in the art for purification of an immunoglobulin molecule, for example, by chromatography (e.g., ion exchange, affinity, particularly by affinity for the specific antigen after Protein A purification, and sizing column chromatography), centrifugation, differential solubility, or by any other standard techniques for the purification of protein. Further, SYNAGIS® or an antigen-binding fragment thereof may be fused to heterologous protein, polypeptide or peptide sequences described herein or otherwise known in the art to facilitate purification.

Antigen-binding fragments of SYNAGIS® that immunospecifically bind RSV may be generated by known techniques. For example, Fab and F(ab')$_2$ fragments may be produced by proteolytic cleavage of immunoglobulin molecules, using enzymes such as papain (to produce Fab fragments) or pepsin (to produce F(ab')$_2$ fragments). F(ab')$_2$ fragments contain the complete light chain, and the variable region, the CH1 region and the hinge region of the heavy chain.

5.4 Methods of Monitoring the Stability and Aggregation of Antibody Formulations There are various methods available for assessing the stability of protein formulations, including antibody formulations, based on the physical and chemical structures of the proteins as well as on their biological activities. For example, to study denaturation of proteins, methods such as charge-transfer absorption, thermal analysis, fluorescence spectroscopy, circular dichroism, NMR, and HPSEC, are available. See, for example, Wang et al., 1988, J. of Parenteral Science & Technology 42(supp):S4-S26. The rCGE, and HPSEC are the most common and simplest methods to assess the formation of protein aggregates, protein degradation and protein fragmentation. Accordingly, the stability of the liquid formulations of the present invention may be assessed by these methods.

For example, the stability of the liquid formulations of the present invention may be evaluated by HPSEC or rCGE, wherein the percentage area of the peaks represents the non-degraded SYNAGIS® or non-degraded antigen-binding fragments of SYNAGIS®. In particular, approximately 250 μg of SYNAGIS® or an antigen-binding fragment thereof (approximately 25 μl of a liquid formulation comprising 10 mg/ml of SYNAGIS® or an antigen-binding fragment thereof) is injected onto a TOSOH TSK G3000SW$_{XL}$ column (7.8 mm×30 cm) fitted with a TSK SW x1 guard column (6.0 mm×4.0 cm), SYNAGIS® or an antigen-binding fragment thereof is eluted isocratically with 0.1 M disodium phosphate containing 0.1 M sodium sulfate and 0.05% sodium azide, at a flow rate of 0.8 to 1.0 ml/min. Eluted protein is detected using UV absorbance at 280 nm. SYNAGIS® reference standard is in the assay as a control and the results are reported as the area percent of the product monomer peak compared to all other peaks excluding the included volume peak observed approximately at 12 to 14 minutes. Peaks eluting earlier than the monomer peak are recorded as percent aggregate.

The liquid formulations of the present invention exhibit low to undetectable levels of aggregation as measured by HPSEC or rCGE, that is, no more than 51%, no more than 40%, no more than 3%, no more than 2%, no more than 1%, and most preferably no more than 0.5% aggregate by weight protein, and low to undetectable levels of fragmentation, that is, 80% or higher, 85% or higher, 90% or higher, 95% or higher, 98% or higher, or 99% or higher, or 99.5% or higher of the total peak area in the peak(s) representing intact antibodies or fragments thereof. In the case of SDS-PAGE, the density or the radioactivity of each band stained or labeled with radioisotope can be measured and the % density or % radioactivity of the band representing non-degraded SYNAGIS® or antigen-binding fragments thereof can be obtained.

The stability of the liquid formulations of the present invention can be also assessed by any assays which measures the biological activity SYNAGIS® or an antigen-binding fragment thereof in the formulation. The biological activities of an antibody include, but not limited to, antigen-binding activity, complement-activation activity, Fc-receptor binding activity, and so forth. Antigen-binding activity of SYNAGIS® or an antigen-binding fragment thereof can be measured by any method known to those skilled in the art, including but not limited to ELISA, radioimmunoassay, West blot, and the like. Complement-activation activity can be measured by a C3a/C4a assay in the system where SYNAGIS® or an antigen-binding fragment thereof is reacted in the presence of the complement components with cells expressing a RSV antigen. Also see Harlow et al., Antibodies: A Laboratory Manual, (Cold Spring Harbor Laboratory Press, 2nd ed. 1988) (incorporated by reference herein in its entirety). An ELISA based assay, e.g., may be used to compare the ability of a liquid formulation of SYNAGIS® or an antigen-binding fragment thereof to immunospecifically bind to a RSV antigen to a SYNAGIS® reference standard. In this assay, plates are coated with RSV antigen (in particular, the A antigenic site of F protein of RSV) and the binding signal of a set concentration of a SYNAGIS® referee standard is compared to the binding signal of the same concentration of the liquid formulation of SYNAGIS® or an antigen-binding fragment thereof.

The purity of the liquid antibody formulations of the invention may be increased by any method well-known to one of skilled in the art such as, e.g., HPSEC. The sterility of the liquid antibody formulations may be assessed as follows: sterile soybean-casein digest medium and fluid thioglycollate medium are inoculated with a test liquid antibody formulation by filtering the liquid antibody formulation through a sterile filter having a nominal porosity of 0.45 μm. When using the Sterisure™ or Steritest™ method, each filter device is aseptically filled with approximately 100 ml of sterile soybean-casein digest medium or fluid thioglycollate medium. When using the conventional method, the challenged filter is aseptically transferred to 100 ml of sterile soybean-casein digest medium or fluid thioglycollate medium. The media are incubated at appropriate temperatures and observed three times over a 14 day period for evidence of bacterial or fungal growth.

5.5 Prophylactic and Therapeutic Utility of the Antibody Formulations

The present invention is also directed to antibody-based therapies which involve administering to a subject, preferably a mammal, most preferably a human, the liquid antibody formulations of the present invention for preventing, treating, managing or ameliorating a RSV infection or one or more symptoms thereof. Prophylactic and therapeutic formulations of the invention comprise SYNAGIS® or an antigen-binding fragment thereof at concentrations of from about 15 mg/ml to about 300 mg/ml in a solution containing histidine.

The liquid formulations of the invention may comprise modified SYNAGIS® or antigen-binding fragments thereof that have improved in vivo half-lives compared to known antibodies that immunospecically binds to a RSV antigen (e.g., unmodified SYNAGIS®).

In one embodiment, the liquid formulations of the present invention are administered to a mammal, preferably a human, to prevent, treat, manage or ameliorate a RSV infection or one or more symptoms thereof. In another embodiment, the liquid formulations of the invention are administered to a human with cystic fibrosis, bronchopulmonary dysplasia, congenital heart disease, congenital immunodeficiency or acquired immunodeficiency, or to a human who has had a bone marrow transplant to prevent, treat, mange or ameliorate a RSV infection or one or more symptoms thereof. In another embodiment, the liquid formulations of the invention are administered to a human infant, preferably a human infant born prematurely or a human infant at risk of hospitalization for a RSV infection to prevent, treat, manage or ameliorate a RSV infection or one or more symptoms thereof. In another embodiment, the liquid formulations of the invention are administered to an elderly person to prevent, treat, manage or ameliorate a RSV infection or one or more symptoms thereof. In yet another embodiment, the liquid formulations of the invention are administered to a subject in an institution or group home (e.g., a nursing home or orphanage).

The liquid formulations of the present invention may be used locally or systemically in the body of a subject prophylactically or therapeutically. The formulations of the present invention may also be advantageously utilized in combination with other therapies useful in the prevention, treatment, management or amelioration of a RSV infection (e.g., a prophylactic or a therapeutic agent other than SYNAGIS®. Non-limiting examples of prophylactic or therapeutic agents that can be used in combination with the liquid formulations of the present invention, see Section 5.6, infra.

When one or more other therapies are used, they can be administered separately, in any appropriate form and by any suitable route. A liquid formulation of the invention may be administered to a mammal, preferably a human, concurrently with one or more other therapies (e.g., one or more other prophylactic or therapeutic agents) useful for the prevention, treatment, management or amelioration of a RSV infection or one or more symptoms thereof. The term "concurrently" is not limited to the administration of therapies at exactly the same time, but rather it is meant that a liquid formulation of the invention and another therapy are administered to a mammal in a sequence and within a time interval such that SYNAGIS® or an antigen-binding fragment thereof contained in the liquid formulation can act together with the other therapy to provide an increased benefit than if they were administered otherwise. For example, a liquid formulation of the invention and one or more other prophylactic or therapeutic agents useful for prevention, treatment, management or amelioration of a RSV infection may be administered at the same time or sequentially in any order at different points in time; however, if not administered at the same time, they should be administered sufficiently close in time so as to provide the desired therapeutic or prophylactic effect.

In various embodiments, a liquid formulation of the invention and one or more other therapies (e.g., one or more other prophylactic or therapeutic agents) useful for prevention, treatment, management or amelioration of a RSV infection or a symptom thereof are administered less than 1 hour apart, at about 1 hour apart, at about 1 hour to about 2 hours apart, at about 2 hours to about 3 hours apart, at about 3 hours to about 4 hours apart, at about 4 hours to about 5 hours apart, at about 5 hours to about 6 hours apart, at about 6 hours to about 7 hours apart, at about 7 hours to about 8 hours apart, at about 8 hours to about 9 hours apart, at about 9 hours to about 10 hours apart, at about 10 hours to about 11 hours apart, at about 11 hours to about 12 hours apart, no more than 24 hours apart or no more than 48 hours apart. In preferred embodiments, a liquid formulation of the invention and one or more other therapies (e.g., one or more other prophylactic or therapeutic agents) useful for prevention, treatment, management or amelioration of a RSV infection or a symptom thereof are administer within the same patient visit. In other embodiments, a liquid formulation of the invention and one or more other therapies (e.g. one or more other prophylactic or therapeutic agents) useful for prevention, treatment, management or amelioration of a RSV infection or a symptom thereof are administered at about 2 to 4 days apart, at about 4 to 6 days apart, at about 1 week apart at about 1 to 2 weeks apart, or more than 2 weeks apart. In preferred embodiments, a liquid formulation of the invention and one or more other prophylactic or therapeutic agents useful for prevention, treatment, management or amelioration of a RSV infection or a symptom thereof are administered in a time frame where both agents are still active. One skilled in the art would be able to determine such a time frame by determining the half-life of the administered agents.

In certain embodiments, a liquid formulation of the invention and one or more other therapies (e.g., one or more other prophylactic or therapeutic agents) useful for prevention, treatment, management or amelioration of a RSV infection or a symptom thereof are cyclically administered to a subject. Cycling therapy involves the administration of a first therapy for a period of time, followed by the administration of a second therapy and/or third therapy for a period of time and repeating this sequential administration. Cycling therapy can reduce the development of resistance to one or more of the therapies, avoid or reduce the side effects of one of the therapies, and/or improves the efficacy of the treatment.

In certain embodiments, a liquid formulation of the invention and one or more other therapies (e.g., one or more other prophylactic or therapeutic agents) useful for prevention, treatment, management or amelioration of a RSV infection or a symptom thereof are administered in a cycle of less than about 3 weeks, about once every two weeks, about once every 10 days or about once every week. One cycle can comprise the administration of a therapy (e.g., a therapeutic or prophylactic agent) by infusion over about 90 minutes every cycle, about 1 hour every cycle, about 45 minutes every cycle. Each cycle can comprise at least 1 week of rest, at least 2 weeks of rest, at least 3 weeks of rests. The number of cycles administered is from about 1 to about 12 cycles, more typically from about 2 to about 10 cycles, and more typically from about 2 to about 8 cycles.

Generally, administration of products of a species origin or species reactivity (in the case of antibodies) that is the same species as that of the patient is preferred. Thus, in a preferred embodiment, human or humanized antibodies, fragments derivatives, or analogs, are administered to a human patient for therapy or prophylaxis.

5.6 Agents Useful in Combination with SYNAGIS® Formulations

The present invention provides methods for preventing, managing, treating or ameliorating a RSV infection or one or more symptoms thereof comprising administering to a subject in need thereof a liquid formulation of the invention alone or in combination with one or more therapies (e.g., one or more prophylactic or therapeutic agents) other than SYNAGIS®. The present invention provides methods for preventing, treating managing or ameliorating a RSV infection or one or more symptoms thereof comprising administering to a subject in need thereof a liquid formulation of the invention alone or in combination with one or more therapies (e.g., one or more prophylactic or therapeutic agents) other than SYNAGIS®. The present invention also provides compositions comprising a liquid formulation of SYNAGIS® or an antigen-binding fragment thereof and one or more prophylactic or therapeutic agents other than SYNAGIS® and methods of preventing, treating, managing or ameliorating a RSV infection or one or more symptoms thereof utilizing said compositions. Therapeutic or prophylactic agents include, but are not limited to, small molecules, synthetic drugs, peptides, polypeptides, proteins, nucleic acids (e.g., DNA and RNA nucleotides including, but not limited to, anise nucleotide sequences, triple helices, RNA interference (RNAi), and nucleotide sequences encoding biologically active proteins, polypeptides or peptides) antibodies, synthetic or natural inorganic molecules, mimetic agents, and synthetic or natural organic molecules.

Any therapy which is known to be useful, or which has been used or is currently being used for the prevention, management, treatment, or amelioration of a RSV infection or one or more symptoms thereof can be used in combination with a liquid formulation in accordance with the invention described herein. See, e.g., Gilman et al., *Goodman and Gilman's: The Pharmacological Basis of Therapeutics*, 10th ed., McGraw-Hill, New York, 2001; *The Merck Manual of Diagnosis and Therapy*, Berkow, M. D. et al. (eds.), 17th Ed., Merck Sharp & Dohme Research Laboratories, Rahway, N.J., 1999; *Cecil Textbook of Medicine*, 20th Ed., Bennett and Plum (eds.), W.B. Saunders, Philadelphia, 1996, for information regarding therapies (e.g., prophylactic or therapeutic agents) which have been or are currently being used for preventing, treating, managing, or ameliorating a RSV infection or one or more symptoms thereof. Examples of such agents include, but are not limited to, immunomodulatory agents, anti-inflammatory agents (e.g., adrenocorticoids, corticosteroids (e.g., beclomethasone, budesonide, flunisolide, fluticasone, triamcinolone, methylprednisolone, prednisolone, prednisone, hydrocortisone), glucocorticoids, steroids, non-steroidal anti-inflammatory drugs (e.g. aspirin, ibuprofen, diclofenac, and COX-2 inhibitors), pain relievers, leukotreine antagonists (e.g., montelukast, methyl xanthines, zafirlukast, and zileuton), beta2-agonists (e.g., albuterol, biterol, fenoterol, isoetharie, metaproterenol pirbuterol salbutamol terbutalin formoterol salmeterol, and salbutamol terbutaline), anticholinergic agents (e.g., ipratropium bromide and oxitropium bromide), sulphasalazine, penicillamine, dapsone, antihistamines, anti-malarial agents (e.g., hydroxychloroquine)), and anti-viral agents.

In specific embodiments, a liquid formulation of the invention is used in combination with a monoclonal or chimeric antibody, or with a lymphokine or hematopoietic growth factor (such as, e.g., IL-2, IL-3, IL-4, IL-7, IL-9, IL-10, IL-12, and interferon α, β, and γ), which, for example, serves to increase the number or activity of effector cells which interact with the antibody. A liquid formulation of the present invention may also be advantageously utilized in combination with other monoclonal or chimeric antibodies, or with lymphokines or hematopoietic growth factors (such as, e.g., IL-2, IL-3, IL-4, IL-7, IL-9, IL-10, IL-12, and interferon α, β, and γ), which, for example, serve to increase the immune response. The liquid formulations of the present invention may also be advantageously utilized in combination with one or more drugs used to treat RSV infection such as, for example antiviral agents. The liquid formulations of the present invention may be used in combination with one or more of the following drugs: NIH-351 (Gemini Technologies), recombinant RSV vaccine (MedImmune Vaccines, Inc. U.S. Application Nos. 60/358,934 filed Feb. 21, 2002, Ser. No. 10/373,567 filed Feb. 21, 2003, Ser. No. 10/371,099 filed Feb. 21, 2003, Ser. No. 10/371,122 filed Feb. 21, 2003, Ser. No. 10/371,264 filed Feb. 21, 2003, 60/466,181 filed Apr. 25, 2003 and 60/465,811 filed Apr. 25, 2003, all of which are incorporated herein by reference), RSVf-2 (Intracel), F-50042 (Pierre Fabre), T-786 (Trimeris), VP-36676 (ViroPharma), RFI-641 (American Home Products), VP-14637 (ViroPharma), PFP-1 and PFP-2 (American Home Products), RSV vaccine (Avant Immunotherapeutics), and F-50077 (Pierre Fabre).

5.6.1 Immunomodulatory Agents

Any immunomodulatory agent well-known to one of skilled in the art may be used in accordance with the methods of the invention to prevent, treat, manage or ameliorate a RSV infection or one or more symptoms thereof. Immunomodulatory agents can affect one or more or all aspects of the immune response in a subject. Aspects of the immune response include, but are not limited to, the inflammatory response, the complement cascade, leukocyte and lymphocyte differentiation, proliferation, and/or effector function, monocyte and/or basophil counts, and the cellular communication among cells of the immune system. In certain embodiments of the invention, an immunomodulatory agent modulates one a of the immune response. In other embodiments, an immunomodulatory agent modulates more than one aspect of the immune response. In a preferred embodiment of the invention, the administration of an immunomodulatory agent to a subject inhibits or reduces one or more aspects of the subject's immune response capabilities. In an alternative embodiment of the invention, the immunomodulatory agent enhances one or more aspects of a subject's immune response. In certain embodiments, an immunomodulatory agent is not an anti-inflammatory agent. In a specific embodiment, an immunomodulatory agent is an agent other than a chemotherapeutic agent.

Examples of immunomodulatory agents include, but are not limited to, proteinaceous agents such as cytokines, peptide mimetics, and antibodies (e.g., human, humanized, chimeric, monoclonal polyclonal, Fvs, ScFvs, Fab or F(ab)$_2$ fragments or epitope binding fragments), nucleic acid molecules (e.g., antisense nucleic acid molecules and triple helices), small molecules, organic compounds, and inorganic compounds. In particular, immunomodulatory agents include, but are not limited to, methotrexate, leflunomide, cyclophosphamide, cytoxan, Immuran, cyclosporine A, minocycline, azathioprine, antibiotics (e.g., FK506 (tacrolimus)), methylprednisolone (MP), corticosteroids, steroids, mycophenolate mofetil rapamycin (sirolimus), mizoribine, deoxyspergualin, brequinar, malononitriloamindes (e.g., leflunomide), T cell receptor modulators, and cytokine receptor modulators.

Examples of T cell receptor modulators include, but are not limited to, anti-T cell receptor antibodies (e.g., anti-CD4 antibodies (e.g., cM-T412 (Boeringer), IDEC-CE9.1® (IDEC and SKB), mAB 4162W94, Orthoclone and OKTcdr4a (Janssen-Cilag)), anti-CD3 antibodies (e.g., Nuvion (Product Design Labs), OKT3 (Johnson & Johnson), or Rituxan (IDEC)), anti-CD2 antibodies (e.g., an anti CD5 ricin-linked immunoconjugate), anti-CD7 antibodies (e.g., CHH-380 (Novartis)), anti-CD8 antibodies, anti-CD40 ligand monoclonal antibodies (e.g., IDEC-131 (IDEC)), anti-D52 antibodies (e.g., CAMPATH 1H (Ilex)), anti-CD2 antibodies (e.g., MEDI-507 (MedImmune, Inc., International Publication Nos. WO 02/098370 and WO 02/069904), anti-C11a antibodies (e.g., Xanelim (Genentech)), and anti-B7 antibodies (e.g., IDEC-114) (IDEC))), CTLA4-immunoglobulia, and LFA-31TIP (Biogen, International Publication No. WO 93/08656 and U.S. Pat. No. 6,162,432).

Examples of cytokine receptor modulators include, but are not limited to, soluble cytokine receptors (e.g., the extracellular domain of a TNF-receptor or an antigen-binding fragment thereof, the extracellular domain of an IL-1β receptor or an antigen-binding fragment thereof and the extracellular domain of an IL-6 receptor or an antigen-binding fragment thereof), cytokines or fragments thereof (e.g., interleukin IL-2, IL-3, IL-4, IL-5, IL-6, IL-7, IL-8, IL-9, IL-10, IL-11, IL-12, IL-13, IL-15, IL-23, TNF-α, TNF-β, interferon (IFN)-α, IFN-β, IFN-γ, and GM-CSF), anti-cytokine receptor antibodies (e.g., ant-IFN receptor antibodies, anti-IL-2 receptor antibodies (e.g., Zenapax (Protein Design Labs)), anti-IL-3 receptor antibodies, anti-IL-4 receptor antibodies, anti-IL-6 receptor antibodies, anti-IL-9 receptor antibodies, anti-IL-10 receptor antibodies, anti-IL-12 receptor antibodies, anti-IL-13 receptor antibodies, anti-IL-15 receptor antibodies, and anti-IL-23 receptor antibodies), anti-cytokine antibodies (e.g., anti-IFN antibodies, anti-TNF-α antibodies, anti-IL-1β antibodies, anti-IL-3 antibodies, anti-IL-6 antibodies, anti-IL-8 antibodies (e.g., ABX-IL-8 (Abgenix)), anti-IL-9 antibodies, anti-IL-12 antibodies, anti-IL-13 antibodies, anti-IL-15 antibodies, and anti-IL-23 antibodies).

In a specific embodiment, a cytokine receptor modulator is IFN, IL-2, IL-3, IL-4, IL-10, IL-12 or an antigen-binding fragment thereof. In another embodiment, a cytokine receptor modulator is an anti-IL-1β antibody, anti-IL-6 antibody, anti-IL-9 antibody, anti-IL-12 receptor antibody, or anti-TNF-α antibody. In another embodiment, a cytokine receptor modulator is the extracellular domain of a TNF-receptor or an antigen-binding fragment thereof.

An immunomodulatory agent may be selected to interfere with the interactions between the T helper subsets (TH1 or TH2) and B cells to inhibit neutralizing antibody formation. Antibodies that interfere with or block the interactions necessary for the activation of B cells by TH Cr helper) cells, and thus block the production of neutralizing antibodies, are useful as immunomodulatory agents in the methods of the invention. For example, B cell activation by T cells requires certain interactions to occur (Durie et al., Immunol. Today, 15(9): 406-410 (1994)), such as the binding of CD40 ligand on the T helper cell to the CD40 antigen on the B cell, and the binding of the CD28 and/or CTLA4 ligands on the T cell to the B7 antigen on the B cell. Without both interactions, the B cell cannot be activated to induce production of the neutralizing antibody.

The CD40 ligand (CD40L)-CD40 interaction is a desirable point to block the immune response because of its broad activity in both T helper cell activation and function as well as the absence of redundancy in its signaling pathway. Thus, in a specific embodiment of the invention, the interaction of CD40L with CD40 is transiently blocked at the time of administration of one or more of the immunomodulatory agents. This can be accomplished by treating with an agent which blocks the CD40 ligand on the TH cell and interferes with the normal binding of CD40 ligand on the T helper cell with the CD40 antigen on the B cell. An antibody to CD40 ligand (anti-CD40L) (available from Bristol-Myers Squibb Co; see, e.g., European patent application 555,880, published Aug. 18, 1993) or a soluble CD40 molecule can be selected and used as an immunomodulatory agent in accordance with the methods of the invention.

An immunomodulatory agent may be selected to inhibit the interaction between TH1 cells and cytotoxic T lymphocytes ("CTLs") to reduce the occurrence of CTL-mediated killing. An immunomodulatory agent may be selected to alter (e.g., inhibit or suppress) the proliferation, differentiation, activity and/or function of the $CD4^+$ and/or $CD8^+$ T cells. For example, antibodies specific for T cells can be used as immunomodulatory agents to deplete, or alter the proliferation, differentiation, activity and/or function of $CD4^+$ and/or $CD8^+$ T cells.

In one embodiment, an immunomodulatory agent which reduces or inhibits one or more biological activities (e.g., the differentiation, proliferation, and/or effector functions) of TH0, TH1, and/or TH2 subsets of $CD4^+$ T helper cells is administered to a subject with a RSV infection in accordance with the methods of the invention. One example of such an immunomodulatory agent is IL-4. IL-4 enhances antigen-specific activity of TH2 cells at the expense of the TH1 cell function (see, e.g., Yokota et al., 1986 Proc. Natl. Acad. Sci., USA, 83:5894-5898; and U.S. Pat. No. 5,017,691). Other examples of immunomodulatory agents that affect the biological activity (e.g., proliferation, differentiation, and/or effector functions) of T-helper cells (in particular, TH1 and/or TH2 cells) include, but are not limited to, IL-2, IL-4, IL-5, IL-6, IL-10, II-12, IL-13, IL-15, IL-23, and interferon (IFN)-γ.

In another embodiment, an immunomodulatory agent administered to a subject with a RSV infection in accordance with the methods of the invention is a cytokine that prevents antigen presentation. In a specific embodiment, an immunomodulatory agent used in the methods of the invention is IL-10. IL-10 also reduces or inhibits macrophage action which involves bacterial elimination.

In accordance with the invention, one or more immunomodulatory agents arm administered to a subject with a RSV infection prior to, subsequent to, or concomitantly with a liquid formulation of SYNAGIS® or an antigen-binding fragment thereof. Preferably, one or more immunomodulatory agents are administered in combination with a liquid formulation of SYNAGIS® or an antigen-binding fragment thereof to a subject with a RSV infection to reduce or inhibit one or more aspects of the immune response as deemed necessary by one of skilled in the art Any technique well-known to one skilled in the art can be used to measure one or more aspects of the immune response in a particular subject, and thereby determine when it is necessary to amine an immunomodulatory agent to said subject. In a preferred embodiment, a mean absolute lymphocyte count of approximately 500 cells/$mm^3$, preferably 600 cells/$mm^3$, 650 cells/$mm^3$, 700 cells/$mm^3$, 750 cells/$mm^3$, 800 cells/$mm^3$, 900 cells/$mm^3$, 1000 cells/$mm^3$, 1100 cells/$mm^3$, or 1200 cells/$mm^3$ is maintained in a subject. In another preferred embodiment, a subject with a RSV infection is not administered an immunomodulatory agent if their absolute lymphocyte count is 500 cells/$mm^3$ or less, 550 cells/$mm^3$ or less, 600 cells/$mm^3$ or less, 650 cells/$mm^3$ or less, 700 cells/$mm^3$ or less, 750 cells/$mm^3$ or less, or 800 cells/$mm^3$ or less.

In a specific embodiment, one or more immunomodulatory agents are administered in combination with a liquid formulation of SYNAGIS® or an antigen-binding fragment thereof to a subject with a RSV infection so as to transiently reduce or inhibit one or more aspects of the immune response. Such a transient inhibition or reduction of one or more aspects of the immune system can last for hours, days, weeks, or months. Preferably, the transient inhibition or reduction in one or more aspects of the immune response lasts for a few hours (e.g., 2 hours, 4 hours, 6 hours, 8 hours, 12 hours, 14 hours, 16 hours, 18 hours, 24 hours, 36 hours, or 48 hours), a few days (e.g., 3 days 4 days, 5 days, 6 days, 7 days, or 14 days), or a few weeks (e.g., 3 weeks, 4 weeks, 5 weeks or 6 weeks). The transient reduction or inhibition of one or more aspects of the immune response enhances the prophylactic and/or therapeutic effect(s) of a liquid formulation of SYNAGIS® or an antigen-binding fragment thereof.

In a preferred embodiment, proteins, polypeptides or peptides (including antibodies) that are utilized as immunomodulatory agents are derived from the same species as the recipient of the proteins, polypeptides or peptides so as to reduce the likelihood of an immune response to those proteins, polypeptides or peptides. In another preferred embodiment, when the subject is a human, the proteins, polypeptides, or peptides that are utilized as immunomodulatory agents are human or humanized.

Nucleic acid molecules encoding proteins, polypeptides, or peptides with immunomodulatory activity or proteins, polypeptides, or peptides with immunomodulatory activity can be administered to a subject with a RSV infection in accordance with the methods of the invention. Further, nucleic acid molecules encoding derivatives, analogs, or fragments of proteins, polypeptides, or peptides with immunomodulatory activity, or derivatives, analogs, or fragments of proteins, polypeptides, or peptides with immunomodulatory activity can be administered to a subject with a RSV infection in accordance with the methods of the invention. Preferably, such derivatives, analogs, and fragments retain the immunomodulatory activity of the full-length, wild-type protein, polypeptide, or peptide.

Preferably, agents that are commercially available and known to function as immunomodulatory agents are used in the methods of the invention. The immunomodulatory activity of an agent can be determined in vitro and/or in vivo by any technique well-known to one skilled in the art, including, e.g., by CTL assays, proliferation assays, and immunoassays (e.g. ELISAs) for the expression of particular proteins such as co-stimulatory molecules and cytokines.

5.6.2 Anti-inflammatory Agents

Any anti-inflammatory agent, including agents useful in therapies for inflammatory disorders, well-known to one of skilled in the art can be used in accordance with methods of the invention to prevent, treat, manage, or ameliorate a RSV infection or one or more symptoms thereof. Non-limiting examples of anti-inflammatory agents include non-steroidal anti-inflammatory drugs (NSAIDs), steroidal anti-inflammatory drugs, anticholinergics (e.g., atropine sulfate, atropine methylnitrate, and ipratropium bromide (ATROVENT™), beta2-agonists (e.g., abuterol (VENTOLIN™ and PROVENDER), bitolterol (TORNALATE™, levalbuterol (XOPONEX™), metaproterenol (ALUPENT™), pirbuterol (MAXAIR™), terbutlaine (BRETHAIRE™ and BRETHINE™), albuterol (PROVENTIL™, REPETABS™, and VOLMAX™, formoterol FORADIL AEROLIZER™, and salmeterol (SEREVENT™ and SEREVENT DISKUS™)), and methylxanthines (e.g., theophylline (UNIHYL™, THEO-DUR™, SLO-BID™, and TEHO-42™)). Examples of NSAIDs include, but are not limited to, aspirin, ibuprofen, celecoxib (CELEBREX™), diclofenac (VOLTAREN™), etodolac (LODINE™, fenoprofen (NALFON™, indomethacin (IDOCIN™, ketoralac (TORADOL™, oxaprozin (DAYPRO™), nabumetone (RELAFEN™), sulindac (CLINORIL™, tolmentin (TOLECTIN™, rofecoxib (VIOXX™), naproxen (ALEVE™, NAPROSYN™), ketoprofen (ACTRON™) and nabumetone (RELAFEN™). Such NSAIDs function by inhibiting a cyclooxygenase enzyme (e.g., COX-1 and/or COX-2). Examples of steroidal anti-inflammatory drugs include, but are not limited to, glucocorticoids, d no (DECADRON™, corticosteroids (e.g., methylprednisolone (MEDROL™)), cortisone, hydrocortisone, predisone (PREDNISONE™ and DELTASONE™), prednisolone (PRELONE™ and PEDIAPRED™), triamcinolone, azulfidine, and inhibitors of eicosanoids (e.g., prostaglandins, thromboxanes, and leukotrienes (see Table 2, infra, for non-limiting examples of leukotriene and typical dosages of such agents)).

5.6.3 Anti-Viral Agents

Any anti-viral agent well-known to one of skilled in the art (in particular, one useful for the treatment, prevention, management, or amelioration of a RSV infection) can be used in accordance with the methods of the invention to prevent, treat, manage or ameliorate a RSV infection or one or more symptoms thereof. Non-limiting examples of anti-viral agents include proteins, polypeptides, peptides, fusion proteins antibodies, nucleic acid molecules, organic molecules, inorganic molecules, and small molecules that inhibit and/or reduce the attachment of a virus to its receptor, the internalization of a virus into a cell, the replication of a virus, or release of virus from a cell. In particular, anti-viral agents include, but are not limited to, nucleoside analogs (e.g., zidovudine, acyclovir, gangcyclovir, vidarabine, idoxuridine, trifluridine, and ribavirin), foscarnet, amantadine, rimantadine, saquinavir, indinavir, ritonavir, alpha-interferons and other interferons, and AZT.

In specific embodiments, the anti-viral agent is an antibody agent other than SYNAGIS® that is immunospecific for a viral antigen. As used herein, the term "viral antigen" includes, but is not limited to, any RSV peptide, polypeptide and protein (e.g., RSV F glycoprotein and RSV G glycoprotein) that is capable of eliciting an immune response.

In preferred embodiments, the viral infection is RSV and the anti-viral antigen is an antibody other than SYNAGIS® that immunospecifically binds to an antigen of RSV. In certain embodiments, the anti-RSV-antigen antibody immunospecifically binds to a RSV antigen of the Group A of RSV. In other embodiments, the anti-RSV-antigen antibody immunospecifically binds to a RSV antigen of the Group B of RSV. In other embodiments, the anti-RSV antigen antibody immunospecifically binds to an antigen of RSV of one Group and cross reacts with the analogous antigen of the other Group. In particular embodiments, the anti-RSV-antigen antibody immunospecifically binds to a RSV nucleoprotein, RSV phosphoprotein, RSV matrix protein, RSV small hydrophobic protein, RSV RNA-dependent RNA polymerase, RSV F protein, and/or RSV G protein. In additional specific embodiments, the anti-RSV-antigen antibody binds to allelic variants of a RSV nucleoprotein, a RSV nucleocapsid protein, a RSV phosphoprotein, a RSV matrix protein, a RSV attachment glycoprotein, a RSV fusion glycoprotein, a RSV nucleocapsid protein, a RSV matrix protein, a RSV small hydrophobic protein, a RSV RNA-dependent RNA polymerase, a RSV F protein, a RSV L protein, a RSV P protein and/or a RSV G protein.

Anti-viral therapies and their dosages, routes of administration and recommended usage are known in the art and have been described in such literature as the *Physician's Desk Reference* (57th ed., 2003). Additional information on respiratory viral infections is available in *Cecil Textbook of Medicine* (18th ed., 1988).

5.7 Methods of Administering the SYNAGIS® Formulations

The invention provides methods of treatment, prophylaxis, and amelioration of a RSV infection or one or more symptoms thereof by administrating to a subject of an effective amount of liquid formulations of the invention. The subject is preferably a mammal such as non-primate (e.g., cows, pigs, horses, cats, dogs, rats etc.) and a primate (e.g., monkey such as a cynomolgous monkey and a human). In a preferred embodiment, the subject is a human. In another preferred embodiment, the subject is a human infant or a human infant born prematurely.

Various delivery systems are known and can be used to administer a liquid formulation of the present invention.

Methods of administering SYNAGIS® liquid formulations of the present invention include, but are not limited to, parenteral administration (e.g., intradermal, intramuscular, intraperitoneal intravenous and subcutaneous), epidural administration, topical administration, pulmonary administration, and mucosal administration (e.g., intranasal and oral routes). In a specific embodiment, liquid formulations of the present invention are administered intramuscularly, intravenously, or subcutaneously and, preferably, intramuscularly. The formulations may be administered by any convenient route, for example by infusion or bolus injection, by absorption through epithelial or mucocutaneous linings (e.g., oral mucosa, rectal and intestinal mucosa, etc.) and may be administered together with other biologically active agents. Administration can be systemic or local. In addition, pulmonary administration can be employed, e.g., by use of an inhaler or nebulizer.

The invention also provides that a liquid formulation of the present invention is packaged in a hermetically sealed container such as an ampoule or sachette indicating the quantity of the SYNAGIS® or antigen-binding fragments thereof. Preferably, the liquid formulations of the present invention are in a hermetically sealed container indicating the quantity and concentration of the antibody or antibody fragment. Preferably, the liquid formulation of the present invention is supplied in a hermetically sealed container at least 15 mg/ml, 20 mg/ml, 30 mg/ml, 40 mg/ml, 50 mg/ml, 60 mg/ml, 70 mg/ml, 80 mg/ml, 90 mg/ml, 100 mg/ml, 150 mg/ml, 200 mg/ml, 250 mg/ml, or 300 mg/ml and, most preferably, 105 mg/ml, in a quantity of 1 ml, 2 ml, 3 ml, 4 ml, 5 ml, 6 ml, 7 ml, 8 ml, 9 ml, 10 ml, 15 ml, or 20 ml and, most preferably, 1.2 ml.

The amount of the liquid formulations of the present invention which will be effective in the prevention, treatment, management or amelioration of a RSV infection or one or more symptoms thereof can be determined by standard clinical techniques. For example, the dosage of the composition which will be effective in the treatment, prevention or amelioration of symptoms associated with a RSV infection can be determined by administering the formulation to a cotton rat, measuring the RSV titer after challenging the cotton rat with $10^5$ pfu of RSV and comparing the RSV titer to that obtain for a cotton rat not administered the formulation. Accordingly, a dosage that results in a 2 log decrease or a 99% reduction in RSV titer in the cotton rat challenged with $10^5$ pfu of RSV relative to the cotton rat challenged with $10^5$ pfu of RSV but not administered the formulation is the dosage of the formulation that can be administered to a human for prevention, treatment, management or amelioration of a RSV infection or one or more symptoms thereof. The dosage of the formulation which will be effective in prevention, treatment, management or amelioration of a RSV infection or one or more symptoms thereof can be determined by administering the formulation to an animal model (e.g., a cotton rat or monkey) and measuring the serum titer of SYNAGIS® or antigen-binding fragments thereof. Accordingly, a dosage of the formulation that results in a serum titer of at least 1 μg/ml, preferably 2 μg/ml, 5 μg/ml, 10 μg/ml, 20 μg/ml, 25 μg/ml, at least 35 μg/ml, at least 40 μg/ml, at least 50 μg/ml at least 75 μg/ml, at least 100 μg/ml, at least 125 μg/ml, at least 150 μg/ml, at least 200 μg/ml, at least 250 μm, at least 300 μg/ml at least 350 μg/ml, at least 400 μg/ml, or at least 450 μg/ml can be administered to a human for prevention, treatment, management or amelioration of a RSV infection or one or more symptoms thereof. In addition, in vitro assays may optionally be employed to help identify optimal dosage ranges.

The precise dose to be employed in the formulation will also depend on the mute of administration, and the seriousness of the RSV infection, and should be decided according to the judgment of the practitioner and each patient's circumstances. Effective doses may be extrapolated from dose-response curves derived from in vitro or animal model (e.g., the cotton rat or Cynomolgous monkey) test systems.

For antibodies (e.g., SYNAGIS®, protein, polypeptides, peptides and fusion proteins, the dosage administered to a patient is typically about 1 mg/kg to 30 mg/kg of the patient's body weight. Preferably, the dosage administered to a patient is between 10 mg/kg and 20 mg/kg of the patient's body weight, more preferably 15 mg/kg of the patient's body weight. Generally, human antibodies have a longer half-life within the human body than antibodies from other species due to the immune response to the foreign polypeptides. Thus, lower dosages of human antibodies and less frequent administration is often possible. Further, the dosage, volume and frequency of administration of liquid formulations of the present invention may be reduced by increasing the concentration of SYNAGIS® or an antigen-binding fragment thereof in the formulations, increasing affinity and/or avidity of SYNAGIS® or an antigen-binding fragment thereof, and/or increasing the half-life of SYNAGIS® or an antigen-binding fragment thereof.

Exemplary doses of a small molecule include milligram or microgram amounts of the small molecule per kilogram of subject or sample weight (e.g., about 1 microgram per kilogram to about 500 milligrams per kilogram, about 100 micrograms per kilogram to about 5 milligrams per kilogram, or about 1 microgram per kilogram to about 50 micrograms per kilogram).

In a specific embodiment, a mammal, preferably a human, is administered a stable liquid formulation of the present invention for the prevention, treatment, management or amelioration of a RSV infection or one or more symptoms thereof in an amount effective for decreasing RSV titers. In accordance with this embodiment, an effective amount of the liquid formulations of the present invention reduces the RSV titers in the lung as measured, for example, by the concentration of RSV in sputum samples or a lavage from the lungs from a mammal. In another embodiment, a mammal, preferably a human, is administered a liquid formulation of the present invention for the prevention, treatment, management or amelioration of a RSV infection or one or more symptoms thereof in an amount effective for inducing an immune response in the mammal.

In another embodiment, a mammal, preferably a human, is administered a first dose of a liquid formulation of the present invention comprising 30 mg/kg or less, 15 mg/kg or less, 10 mg/kg or less, 5 mg/kg or less, 3 mg/kg or less, 1 mg/kg or less, or 0.5 mg/kg or less of SYNAGIS® or an antigen-binding fragment thereof for the prevention, treatment, management or amelioration of a RSV infection or one or more symptoms thereof in an amount effective to induce a serum titer of at least 1 μg/ml preferably at least 2 μg/ml at least 5 μg/ml, at least 10 μg/ml, at least 15 μg/ml, at least 20 μg/ml, at least 25 μg/ml, at least 30 μg/ml, at least 35 μg/ml, at least 40 μg/ml, 20 days (preferably 25, 30, 35, 40 days) after the administration of the first dose and prior to the administration of a subsequent dose. In a specific embodiment, a liquid formulation of the present invention comprises SYNAGIS® or an antigen-binding fragment thereof and is administered to a subject a first dose of about 1 mg/kg to about 30 mg/kg to induce a serum titer of about 40 μg/ml or higher 30 days after the administration of the first dose and prior to the administration of a subsequent dose. Preferably, the serum titer of said SYNAGIS® or an antigen-binding fragment thereof is less than 50 µg/ml, 30 days after the administration of the first dose and prior to the administration of a subsequent dose.

In another embodiment, a mammal, preferably a human, is administered a first dose of a liquid formulations of the present invention comprising 30 mg/kg or less, 15 mg/kg or less, 10 mg/kg or less, 5 mg/kg or less, 3 mg/kg or less, 1 mg/kg or less or 0.5 mg/kg or less of SYNAGIS® or an antigen-binding fragment thereof for the prevention, treatment, management or amelioration of a RSV infection or one or more symptoms thereof in an amount effective to induce a serum titer of at least 1 µg/ml, preferably at least 2 µg/ml, at least 5 µg/ml, at least 10 µg/ml, at least 15 µg/ml, at least 20 µg/ml, or at least 25 µg/ml, 20 days (preferably 25, 30, 35, 40 days) after the administration of the first dose and prior to the administration of subsequent dose. Preferably, the serum titer of said SYNAGIS® or an antigen-binding fragment thereof is less than 30 µg/ml, 30 days after the administration of the first dose and prior to the administration of a subsequent dose.

In another embodiment, a mammal preferably a human, is administered a first dose of a liquid formulation of the present invention comprising 30 mg/kg or less, 15 mg/kg or less, 5 mg/kg or less, 3 mg/kg or less, 1 mg/kg or less or 0.5 mg/kg or less of a modified form of SYNAGIS® or an antigen-binding fragment thereof for the prevention, treatment, management or amelioration of a RSV infection or one or more symptoms thereof which has an increased in vivo half-life in an amount effective to induce a serum titer of at least 1 µg/ml, preferably at least 2 µg/ml, at least 5 µg/ml, at least 10 µg/ml, at least 15 µg/ml, at least 20 µg/ml, or at least 25 µg/ml, 25 days (preferably 30, 35, or 40 days) after the administration of the first dose and prior to the administration of a subsequent dose. Preferably, the serum titer of said SYNAGIS® or an antigen-binding fragment thereof is less than 30 µg/ml 30 days after the administration of the first dose and prior to the administration of a subsequent dose.

In another embodiment, a mammal, preferably a human is administered a first dose of a liquid formulation of the present invention comprising 30 mg/kg or less, 15 mg/kg or less, 5 mg/kg or less, 3 mg/kg or less, 1 mg/kg or less, or 0.5 mg/kg or less of a modified SYNAGIS® or an antigen-binding fragment thereof for the prevention, treatment, management or amelioration of a RSV infection or one or more symptoms thereof which has an increased in vivo half-life in an amount effective to induce a serum titer of at least 1 µg/ml preferably at least 2 µg/ml, least 5 µm/ml, at least 10 µg/ml, at least 15 µg/ml, at least 20 µg/ml, or at least 25 µg/ml, 25 days (preferably 30, 35, or 40 days) after the administration of the first dose and prior to the administration of a subsequent dose. Preferably, the serum titer of said SYNAGIS® or an antigen-binding fragment thereof is less than 30 µg/ml, 30 days after the administration of the first dose and prior to the administration of a subsequent dose.

In another embodiment, a mammal preferably a human, is administered a first dose of the liquid formulation comprising approximately 30 mg/kg or less, 15 mg/kg or less (preferably 10 mg/kg or less, 5 mg/kg or less, 3 mg/kg or less, 1 mg/kg or less, or 0.5 mg/kg or less) of a modified form of SYNAGIS® or an antigen-binding fragment thereof which has an increased in vivo half-life for the prevention, treatment, management or amelioration of a RSV infection or one or more symptoms thereof in an amount effective to induce a serum titer of at least 30 µg/ml preferably at least 35 µg/ml, at least 40 µg/ml, or at least 50 µg/ml 25 days (preferably 30, 35, or 40 days) after the administration of the first dose and prior to the administration of a subsequent dose.

In one embodiment, a mammal, preferably a human, is administered a first dose of a liquid formulation of the present invention for pulmonary delivery comprising 30 mg/kg or less, 15 mg/kg or less, 5 mg/kg or less, 3 mg/kg or less, 1 mg/kg or less, 0.5 mg/kg or less, or 0.01 mg/kg or less of SYNAGIS® or an antigen-binding fragment thereof for the prevention, treatment, management or amelioration of a RSV infection or one or more symptoms thereof in an amount effective to induce a titer of at least 20 ng per mg of lung protein (preferably at least 40 ng/mg, at least 60 ng/mg, at least 80 ng/mg, at least 50 ng/mg, at least 75 ng/mg, at least 100 ng/mg, or at least 150 ng/mg) in an intubation sample or lavage from the lungs of said mammal 20 days (preferably 25, 30, 35, or 40 days) after the administration of the first dose and prior to the administration of a subsequent dose. Preferably, the serum titer of said SYNAGIS® or an antigen-binding fragment thereof is less than 100 ng/ml of protein 30 days after the administration of the first dose and prior to the administration of a subsequent dose.

In another embodiment, a mammal, preferably a human is administered a first dose of a liquid formulation of the present invention 10 mg/kg or less, 5 mg/kg or less, 3 mg/kg or less, 1 mg/kg or less, or 0.5 mg/kg or less of SYNAGIS® or an antigen-binding fragment thereof for the prevention, treatment, management or amelioration of a RSV infection or one or more symptoms thereof in an amount effective to induce a serum titer of at least 35 µg/ml, at least 40 µg/ml, at least 50 µg/ml, at least 80 µml, at last 100 µg/ml, at least 120 µg/ml, at least 150 µg/ml, at least 200 µg/ml, at least 250 µg/ml, or at least 300 µg/ml, 20 days (preferably 25, 30, 35 or 40 days) after the administration of first dose. In another embodiment, a mammal, preferably a human, is administered a first dose of a liquid formulation of the present invention comprising approximately 15 mg/kg of SYNAGIS® or an antigen-binding fragment thereof for the prevention, treatment, management or amelioration of a RSV infection or one or more symptoms thereof in an amount effective to induce a serum titer of at least 100 µg/ml, at least 125 µg/ml, at least 150 µg/ml, at least 200 µg/ml, at least 250 µg/ml, at least 300 µg/ml, at least 350 µg/ml, at least 400 µg/ml, or at least 450 µg/ml 20 days (preferably 25, 30, 35 or 40 days) after the administration of the first dose. The term "approximately 15 mg/kg" as used herein refers to a range of between 14 mg/kg and 16 mg/kg.

In another embodiment, a mammal preferably a human, is administered a dose of a liquid formulation of the present invention comprising SYNAGIS® or an antigen-binding fragment thereof for the prevention of a RSV infection or a symptom thereof in an amount effective to induce a prophylactically effective serum titer of less than 10 µg/ml, less than 8 µg/ml, less than 5 µg/ml, less than 3 µg/ml, less than 1 µg/ml, or less than 0.5 µg/ml 30 days after the administration of the dose, wherein said prophylactically effective serum titer is the serum titer that reduces the incidence of RSV infection in the human or the serum titer in a cotton rat that results in a RSV titer 5 days after challenge with $10^5$ pfu RSV that is 99% lower than the RSV titer in the cotton rat 0 days after challenge with $10^5$ pfu of RSV in a cotton rat not administered the dose prior to challenge. Preferably, the dose of the therapeutic or pharmaceutical composition comprises 10 mg/kg or less, 5 mg/kg or less, 3 mg/kg or less, 1 mg/kg or less, or 0.5 mg/kg or less of SYNAGIS® or an antigen-binding fragment thereof.

In yet another embodiment, a mammal, preferably a human is administered a dose of a liquid formulation of the present invention comprising SYNAGIS® or an antigen binding fragment thereof for the treatment, management or amelioration of a RSV infection or one or more symptoms thereof in an amount effective to induce a therapeutically effective serum titer of less than 10 µg/ml, less than 8 µg/ml, less than 5 µg/ml, less than 3 µg/ml, less than 1 µg/ml, or less than 0.5 µg/ml 30 days after the administration of the dose, wherein said therapeutically effective serum titer is the serum titer that reduces the severity or length of RSV infection or is the serum titer in a cotton rat that results in a RSV titer in the rat 5 days after challenge with $10^5$ pfu RSV that is 99% lower than the RSV titer 0 days after challenge with $10^5$ pfu of RSV in a cotton rat not administered the dose prior to challenge. Preferably, the dose of the liquid formulation of the present invention comprises 12 mg/kg or less, 10 mg/kg or less, 5 mg/kg or less, 3 mg/kg or less, 1 mg/kg or less, or 0.5 mg/kg or less of an antibody or an antigen-binding fragment thereof.

In a specific embodiment, formulations of the present invention are administered once a month just prior to or during the RSV season. In another embodiment, the formulations are administered every two months just prior to or during the RSV season. In yet another embodiment, the stable formulations of the present invention are administered once just prior to or during the RSV season. The term "RSV season" refers to the season when RSV infection is most likely to occur. Typically, the RSV season in the northern hemisphere commences in November and lasts through April.

In one embodiment, a liquid formulation comprising approximately 5 mg/kg or less (preferably 1.5 mg/kg or less) of SYNAGIS® or an antigen-binding fragment thereof is administered five times, 3 times, or 1 to 2 times during a RSV season to a mammal, preferably a human. In another embodiment, approximately 1.5 mg/kg of SYNAGIS® or an antigen-binding fragment thereof, in the liquid formulations of the present invention is administered monthly five times during a RSV season to a mammal, preferably a human, intramuscularly. In another embodiment, 3 mg/kg of SYNAGIS® or an antigen-binding fragment thereof in the liquid formulation of the invention is administered monthly three times during a RSV season to a mammal, preferably a human, intramuscularly. In yet another embodiment, 5 mg/kg of an SYNAGIS® or an antigen-binding fragment thereof in a liquid formulation of the invention is administered monthly one to two times during a RSV season to a mammal, preferably a human, intramuscularly.

In a specific embodiment, 15 mg/kg of SYNAGIS® or an antigen-binding fragment thereof in the liquid formulation of the present invention is administered to a mammal, preferably a human intramuscularly five times during a RSV season, wherein said SYNAGIS® or antibody fragment has an increased in vivo half-life. In another embodiment, approximately 5 mg/kg or less (preferably 1.5 mg/kg or less) of SYNAGIS® or an antigen-binding fragment thereof in the liquid formulation of the present invention is administered five times, 3 times, or 1 to 2 times during a RSV season to a mammal, preferably a human. In another embodiment, 3 mg/kg of SYNAGIS® or an antigen-binding fragment thereof, which has an increased in vivo half-life, in the liquid formulation of the present invention is administered monthly three times during a RSV season to a mammal, preferably a human, intramuscularly. In another embodiment, 5 mg/kg of SYNAGIS® or an antigen-binding fragment thereof, which has an increased in vivo half life, in the liquid formulation of the present invention is administered to a mammal preferably a human, intramuscularly twice times during a RSV season.

5.8 Biological Assays 5.8.1 Immunospecificity of the Antibodies of the Invention Antibodies of the present invention or fragments thereof may be characterized in a variety of ways well-known to one of skill in the art. In particular, antibodies of the invention or antigen-binding fragments thereof in a liquid formulation of the present invention may be assayed for the ability to immunospecifically bind to an epitope of a respiratory syncytial virus. Such an assay may be performed in solution (e.g., Houghten, 1992, Bio/Techniques 13:412-421), on beads (Lam, 1991, Nature 354:82-84), on chips (Fodor, 1993, Nature 364:555-556), on bacteria (U.S. Pat. No. 5,223,409), on spores (U.S. Pat. Nos. 5,571,698; 5,403,484; and 5,223,409), on plasmids (Cull et al., 1992, Proc. Natl. Acad. Sci. USA 89:1865-1869) or on phage (Scott and Smith, 1990, Science 249:386-390; Cwirla et al., 1990, Proc. Natl. Acad. Sci. USA 87:6378-6382; and Felici, 1991, J. Mol. Biol. 222: 301-310) (each of these references is incorporated herein in its entirety by reference). SYNAGIS® or an antigen-binding fragment thereof in a liquid formulation of the present invention can be assayed for its specificity and affinity.

SYNAGIS® or an antigen-binding fragment thereof of the present invention may be assayed for immunospecific binding to a RSV antigen and cross-reactivity with other antigens by any method known in the art. Immunoassays which can be used to analyze immunospecific binding and cross-reactivity include, but are not limited to, competitive and non-competitive assay systems using techniques such as western blots, radioimmunoassays, ELISA (enzyme linked immunosorbent assay), "sandwich" immunoassays, immunoprecipitation assays, precipitin reactions, gel diffusion precipitin reactions, immunodiffusion on assays, agglutination assays, complement-fixation assays, immunoradiometric assays, fluorescent immunoassays, protein A immunoassays, to name but a few. Such assays are routine and well-known in the art (see, e.g., Ausubel et al., eds., 1994, Current Protocols in Molecular Biology, Vol. 1, John Wiley & Sons, Inc., New York, which is incorporated by reference herein in its entirety).

5.8.2 In Vitro and In Vivo Assays

A liquid formulation or a combination therapy of the present invention can be tested in vitro and/or in vivo in various assays or suitable animal model systems for its activity.

A liquid formulation of the present invention for treating, managing, preventing or ameliorating a RSV infection or one or more symptoms thereof can be tested for its ability to inhibit viral replication or reduce viral load in in vitro assays. For example, viral replication can be assayed by a plaque assay such as described, e.g., by Johnson et al., 1997, Journal of Infectious Diseases 176:1215-1224 176:1215-1224. A liquid formulation of the invention administered according to the methods of the invention can also be assayed for their ability to inhibit or down-regulate the expression of viral polypeptides. Techniques known to those of skill in the art, including, but not limited to, western blot analysis, northern blot analysis, and RT-PCR can be used to measure the expression of viral polypeptides and/or viral titers.

A liquid formulation of the invention can be tested in suitable animal model systems prior to use in humans. Such animal model systems include, but are not limited to, rats, mice, chicken, cows, monkeys, pigs, dogs, rabbits, etc. Any animal system well-known in the art may be used. Several aspects of the procedure may vary; said aspects include, but are not limited to, the temporal regime of administering the therapies (e.g., prophylactic and/or therapeutic agents) whether such therapies are administered separately or as an admixture, and the frequency of administration of the therapies.

Animal models can be used to assess the efficacy of the methods of the invention for treating, managing, preventing, or ameliorating a RSV infection or one or more symptom thereof. Animal models for RSV infection include, but are not limited to, those as described by, e.g., Piedimonte et al., Am J Physiol 1999, 277:L831-L840; McArthur-Vaughan et al., J. Med. Primatol. 2002, 31(2):61-73; and Byrd et al., Clin. Infect. Dis. 1997, 25(6):1363-8. In a specific embodiment, cotton rats are administered a liquid formulation comprising SYNAGIS® according to the methods of the invention, challenged with $10^5$ pfu of RSV, and four or more days later, the rats are sacrificed and RSV titer and SYNAGIS® serum titer is determined. Accordingly, a dosage that results in a 2 log decrease or a 99% reduction in RSV titer in the cotton rat challenged with $10^5$ pfu of RSV relative to the cotton rat challenged with $10^5$ pfu of RSV but not administered the formulation is the dosage of the formulation that can be administered to a human for the treatment, prevention or amelioration of a RSV infection or one or more symptoms thereof. Further, this embodiment, the tissues (e.g., the lung tissues) from the sacrificed rats can be examined for histological changes.

The administration of a liquid formulation of the invention according to the methods of the present invention can be tested for its ability to decrease the time course of a RSV infection by at least 25%, preferably at least 50%, at least 60%, at least 75%, at least 85%, at least 95%, or at least 99%. A liquid formulation of the invention can also be tested for its ability to increase the survival period of humans suffering from a RSV infection by at least 25%, preferably at least 50%, at least 60%, at least 75%, at least 85%, at least 95%, or at least 99%. Further, a liquid formulation of the invention can be tested for its ability reduce the hospitalization period of a human suffering from RSV infection by at least 60%, preferably at least 75%, at least 85%, at least 95%, or at least 99%. Techniques known to those of skill in the art can be used to analyze the function of a liquid formulation of the invention in vivo.

Further, any in vitro or in vivo assays known to those skilled in the art can be used to evaluate the prophylactic and/or therapeutic utility of a liquid formulation of the invention disclosed herein for a RSV infection or one or more symptoms thereof.

5.8.3 Toxicity Assays

The toxicity and/or efficacy of the prophylactic and/or therapeutic protocols of the instant invention can be determined by standard pharmaceutical procedures in cell cultures or experimental animals, e.g., for determining the LD50 (the dose lethal to 50% of the population) and the ED50 (the dose therapeutically effective in 50% of the population). The dose ratio between toxic and therapeutic effects is the therapeutic index and it can be expressed as the ratio LD50/ED50. Therapies that exhibit large therapeutic indices are preferred. While therapies that exhibit toxic side effects may be used, care should be taken to design a delivery system that targets such agents to the site of affected tissue in order to minimize potential damage to uninfected cells and, thereby, reduce side effects.

The data obtained from the cell culture assays and animal studies can be used in formulating a range of dosage of the prophylactic and/or therapeutic agents for use in humans. The dosage of such agents lies preferably within a range of circulating concentrations that include the ED50 with little or no toxicity. The dosage may vary within this range depending upon the dosage form employed and the route of administration utilized. For any therapy used in the method of the invention, the therapeutically effective dose can be estimated initially from cell culture assays. A dose may be formulate in animal models to achieve a circulating plasma concentration range that includes the IC50 (i.e., the concentration of the test compound that achieves a half-maximal inhibition of symptoms) as determined in cell culture. Such information can be used to more accurately determine useful doses in humans. Levels in plasma may be measured, for example, by high performance liquid chromatography.

5.9 Kits

The invention provides a pharmaceutical pack or kit comprising one or more containers filled with a liquid formulation of the invention for the prevention, treatment, management or amelioration of a RSV infection or one or more symptoms thereof. In a specific embodiment, the liquid formulations of the invention comprise SYNAGIS® or an antigen-binding fragment thereof recombinantly fused or chemically conjugated to another moiety, including but not limited to, a heterologous protein, a heterologous polypeptide, a heterologous peptide, a large molecule, a small molecule, a marker sequence, a diagnostic or detectable agent, a therapeutic moiety, a drug moiety, a radioactive metal ion, a second antibody, and a solid support.

The present invention provides kits that can be used in the above methods. In one embodiment, a kit comprises a liquid formulation of the invention, in one or more containers. In another embodiment, a kit comprises a liquid formulation of the invention, in one or more containers, and one or more other prophylactic or therapeutic agents useful for the prevention, management or treatment of a RSV infection or one or more symptoms thereof, in one or more other containers. Preferably, the kit further comprises instructions for preventing, treating, managing or ameliorating a RSV infection (e.g., using the liquid formulations of the invention alone or in combination with another prophylactic or therapeutic agent), as well as side effects and dosage information for method of administration. Optionally associated with such container(s) can be a notice in the form prescribed by a governmental agency regulating the manufacture, use or sale of pharmaceuticals or biological products, which notice reflects approval by the agency of manufacture, use or sale for human administration.

6. EXAMPLES

6.1 Example 1 (Stability Study)

An antibody formulation of the present invention comprising, in an aqueous carrier, 25 mM of histidine, 1.6 mM of glycine, and SYNAGIS® at pH 6 was prepared according to the following protocol:

For a 1 kg solution of buffer: In 800 g water, 3.875 g histidine (free base) and 0.12 g glycine were dissolved. The pH was adjusted with 6 N HCl to 6.0±0.2. Water was added to bring the total mass up to 1.0 kg (qs).

For the diafiltration: After the chromatography steps in the purification process, SYNAGIS® was concentrated to a target of 150 g/L. The concentrated product is diafiltered into formulation buffer. The formulated product was diluted to a target manufacturing concentration of 103±3 g/L.

For a stability study, two formulations were prepared: one contained 105 mg/ml of SYNAGIS® and the other contained 160 mg/ml of SYNAGIS®. The stability of each formulation was measured using HPSEC in terms of degrees of aggregate formation and fragmentation during the storage at 2-8° C. for up to 15 months and at 38-42° C. for up to 1 year. For the HPSEC analysis, typically, TosoHaas G3000WXL column with a mobile phase containing 0.1 M sodium phosphate and 0.1 M sodium sulfate, pH 6.8, is used at a flow rate of 0.8 ml/min. A sample containing 250 mg of protein in an appropriate volume is injected into the column and protein peaks are detected by 280 nm UV and/or fluorescence (280 nm excitation and 340 nm emission).

The data showed that there was no detectable increase in aggregation when each formulation of SYNAGIS® was stored at 2-8° C. for 15 months as shown in Table 3.

TABLE 3

Percent Aggregates during Storage at 2-8° C.

| Month | % Aggregates | |
|---|---|---|
| | 105 mg/ml | 160 mg/ml |
| 0 | 0.3 | 0.4 |
| 5 | 0.3 | 0.3 |
| 8 | 0.4 | — |
| 12 | 0.4 | — |
| 15 | 0.4 | 0.5 |

±0.1% error.

When the formulations were stored at 38-42° C. for 60 days, about 1.5% increase in aggregate was observed with the formulation containing 105 mg/ml of SYNAGIS® and 2.0% increase was observed with the formulation containing 160 mg/ml of SYNAGIS®.

6.2 Example 2 (Clinical Study)

The liquid formulation of the present invention comprising 100 mg/ml of SYNAGIS® in an aqueous solution containing 25 mM of histidine and 1.6 mM of glycine at pH 6 is tested for safety and tolerability study in a Phase L, parallel group, double-blind, randomized study at two sites. The study drugs are a liquid (Liq) formulation of SYNAGIS® and the currently licensed lyophilized (Lyo) formulation of SYNAGIS®. A total of 48 volunteers will be randomized to one of four treatment groups:

| | | |
|---|---|---|
| GROUP 1: | N = 12 | 3 mg/kg SYNAGIS ® (Liq) at Study Days 0 and 30 (IM) |
| GROUP 2: | N = 12 | 3 mg/kg SYNAGIS ® (Lyo) at Study Days 0 and 30 (IM) |
| GROUP 3: | N = 12 | 15 mg/kg SYNAGIS ® (Liq) at Study Day 0 (IV) |
| GROUP 4: | N = 12 | 15 mg/kg SYNAGIS ® (Lyo) at Study Day 0 (IV) |

Vital signs will be obtained before and 30 minutes after each dose of study drug. Adverse events will be monitored through 30 days after the last dose of study drug and serious adverse events will be monitored through Study Day 60.

On Study Day 0, all volunteers will have blood collected for SYNAGIS® serum concentration before dosing, at the end of infusion (IV dose groups only), and at 0.25, 0.5, 1, 4, 8, and 12 hours after IM injection or end of infusion. Subsequently, blood samples for determination of SYNAGIS® levels will be collected daily though Study Day 5 and on Study Days 7, 14, 21, 30, 37 (IM groups only), and 60. Serum samples for anti-SYNAGIS® antibodies will be collected on Study Days 0, 7, 14, 21, 30, 37 (IM groups only), and 60. Samples for serum chemistry and CBC with differential and platelets, and urine samples for urinalysis will be collected on Study Day 0 as well as 7 days after each dose of SYNAGIS® (Study Day 7 for the IV groups and Study Days 7 and 37 for the IM groups). Urine βHCG tests will be performed on the day of dosing before each dose of SYNAGIS® (Study Day 0 for the IV groups and Study Days 0 and 30 for the IM groups). A study flow diagram is shown in FIG. 2.

6.2.1 Study Procedures

A. Volunteer Selection

The volunteers in this study will be healthy male or female adults. The volunteer will be counseled by an investigator (physician) who will address the questions and concerns of the volunteer and secure written informed consent for participation in the study. Written informed consent will be obtained prior to conducting study procedures or administration of study drug.

a. Inclusion Criteria

Volunteers must meet all of the following criteria:

1. Male or female.
2. Age 18 through 49 years at the time of the first dose of study drug.
3. Weight ≦150 kg.
4. Written informed consent obtained from the volunteer.
5. Sexually active females, unless surgically sterile, must have used an effective method of avoiding pregnancy (including oral or implanted contraceptives, IUD, female condom, diaphragm with spermicide, cervical cap, abstinence, use of a condom by the sexual partner or sterile sexual partner) for 14 days prior to the first dose of study drug, must agree to continue using such precautions for 30 days after the final dose of study drug, and must have a negative serum pregnancy test within 2 days prior to the first dose of study drug.
6. Healthy by medical history and physical examination.
7. Ability to complete follow-up period of 60 days as required by the protocol.

b. Exclusion Criteria

Volunteers must have none of the following:

1. Acute illness at the start of the study
2. Fever ≧99.5° F. at the start of the study
3. Any drug therapy within 7 days prior to Study Day 0 (except for contraceptives)
4. Blood donation in excess of 400 mL within 6 months of study start
5. Receipt of immunoglobulin or blood products within 60 days before entry into the study
6. Receipt of any investigational drug therapy or standard vaccine within 120 days before the first dose of study drug in this protocol through 60 days after the final dose of study drug
7. History of immunodeficiency
8. History of allergic disease or reactions likely to be exacerbated by any component of the study drug
9. Previous medical history or evidence of an intercurrent illness that may compromise the safety of the volunteer in the study
10. Evidence of infection with hepatitis A, B, or C virus or HIV-1
11. At screening (must be within 21 days before entry into the study) any of the following: CBC: Hgb<12.0 gm/dl; WBC<4,000/mm$^3$; platelet count <120,000/mm$^3$ (or laboratory normal values); AST, ALT, BUN, creatinine>upper limit of normal; other abnormal laboratory values in the sc g panel which in the opinion of the principal investigator are judged to be clinically significant; other abnormal laboratory values in the screening panel which in the opinion of the principal investigator are judged to potentially confound analysis of study results
12. Nursing mother
13. History of alcohol or drug abuse within the past 2 years
14. Evidence of any systemic disease on physical examination B. Randomization a. Volunteer Randomization Procedures and Treatment Allocation At the screening visit, volunteers will be evaluated by the principal investigator to assess eligibility for entry into the study. A master log will be maintained for all screened volunteers. Volunteers who sign an informed consent and who meet eligibility criteria will be entered into the study. When a volunteer arrives in the study site for randomization (Study Day 0), the investigator will confirm that the volunteer meets all inclusion and exclusion criteria. The investigator will then assign a patient identification number (PID). Patient identification numbers will be assigned sequentially within each of the two study sites beginning with #101 in site 1 and with #201 in site 2. Volunteers will be considered to have entered the study when the PID is assigned. A randomization list provided to the study pharmacist at each study site will contain assignments to each of the four treatment groups for volunteers at that site. The investigator will notify MedImmune by facsimile transmission (fax) at 301-527-4217 that a volunteer has been randomized. Volunteers who have been assigned a PID and do not receive any study drug, who receive an incomplete infusion of study drug, who do not receive both IM injections of study drug, or who do not complete at least 50% of the study visits may be replaced at the discretion of the sponsor. Volunteers who withdraw due to an adverse event or whose status cannot be ascertained will not be replaced. Volunteer who withdraw consent for reasons other than an adverse event may be replaced. Replacement volunteers will be assigned a new PID. Volunteer who are replaced will continue to be followed for safety according to the protocol.

b. Blinding

This is a double-blind study. Blinding will be maintained for assignment of volunteers to lyophilized or liquid formulation within IM or IV groups. In order to maintain blinding during administration of the two formulations of SYNAGIS® the study pharmacist at each site will prepare the study drug at a site physically removed from the treatment station and shielded from the observation of the principal investigator or any study personnel directly involved in the conduct of the study. For IM injection, the pharmacist will prepare identical appearing 5 mL syringes containing the calculated volume of either liquid or reconstituted lyophilized SYNAGIS®. For IV infusion, the pharmacist will prepare identical appearing 200 mL infusion bags containing the calculated volume of either liquid or reconstituted lyophilized SYNAGIS®. Labels will not identify whether the syringe/bag contains liquid or reconstituted lyophilized SYNAGIS®. An independent monitor who will review the pharmacy record only, the statistician and clinical supplies manager at MedImmune, and the study pharmacist at the study site are the only individuals who will have access to the randomization list which identifies a volunteer's study treatment allocation. These individuals must not reveal randomization information to anyone. In the event that the study treatment for a volunteer becomes known to the investigator, MedImmune must be notified immediately by the investigator. All instances of unblinding will be documented in the study report.

C. Study Drug a. Study Drug Supplies and Accountability

The sponsor will provide the investigator with adequate quantities of liquid SYNAGIS®, lyophilized SYNAGIS®, and diluent (sterile water for injection). Study drug should be stored at 2° C. to 8° C. (36° F. to 46° F.) and must not be frozen.

Liquid SYNAGIS® will be provided in 3 mL vials containing 100 mg of sterile liquid product in a volume of 1 mL (25 mM histidine, 1.6 mM glycine, at pH 6.0).

Lyophilized SYNAGIS® will be provided in 5 mL vials containing 100 mg of sterile lyophilized product which when formulated (before lyophilization) contains 25 mM histidine, 1.6 mM glycine, and 3% (w/v) mannitol at pH 6.0.

The study pharmacist is required to maintain accurate drug accountability records. Upon completion of the study, all study drug accountability records will be returned to the sponsor. All unused study drug will be returned to the sponsor.

b. Treatment Regimens

The following regimens are employed in the study:

| GROUP 1: | N = 12 | 3 mg/kg SYNAGIS ® (Liq) at Study Days 0 and 30 (IM) |
|---|---|---|
| GROUP 2: | N = 12 | 3 mg/kg SYNAGIS ® (Lyo) at Study Days 0 and 30 (IM) |
| GROUP 3: | N = 12 | 15 mg/kg SYNAGIS ® (Liq) at Study Day 0 (IV) |
| GROUP 4: | N = 12 | 15 mg/kg SYNAGIS ® (Lyo) at Study Day 0 (IV) | c. Ordering and Preparation of Study Drug

The dose of study drug for administration must be prepared by the study pharmacist. The study drug prescription form indicating the PID and the volunteer's body weight will be sent to the pharmacist by the investigator (or designee). The study pharmacist will then use this information to prepare the study drug.

To prepare liquid or lyophilized SYNAGIS® for administration, the pharmacist should remove the tab portion of the vial cap and clean the rubber stopper with 70% ethanol or equivalent. The vial should be vented. Doses for each volunteer will be calculated as described below based on the volunteer's weight (to the nearest 0.1 kilogram) on the day SYNAGIS® is administered. The dose should be rounded to the nearest 0.1 mL. All preparations of study drug must be administered within 6 hours after entering the vial of SYNAGIS®. If it is not administered within 6 hours a new vial or vials must be used.

Preparation of Liquid SYNAGIS®

(1) For IM injections: The required volume of liquid SYNAGIS® (100 mg/mL) will be obtained by pooling the contents of as many vials as necessary with a 5 mL syringe.

Dose (mL)=[Volunteer Weight (kg)×Dose Level (3 mg/kg)]÷Drug Concentration (100 mg/mL)

Example: A volunteer who weighs 75.6 kg receives 2.3 mL of SYNAGIS®

(75.6 kg×3 mg/kg)÷100 mg/mL=2.268 mL (rounded to 2.3 mL)

(2) For IV infusions: The required volume of liquid SYNAGIS® (100 mg/mL) will be obtained by pooling the contents of as many vials as necessary with a 20 mL (or larger) syringe.

Dose (mL)=[Volunteer Weight (kg)×Dose Level (15 mg/kg)]÷Drug Concentration (100 mg/mL)

This volume of liquid SYNAGIS® will then be injected into an empty 200 mL infusion on bag and diluted with diluent 1:4 by adding four volumes of diluent to the bag for a final concentration of 20 mg/mL SYNAGIS®.

Example: A volunteer who weighs 71.4 kg receives 10.7 mL of SYNAGIS®

[(71.4 kg×15 mg/kg)÷100 mg/mL=10.71 mL
(rounded to 10.7 mL)]and 42.8 mL of diluent
(4×10.7) for a total infusion volume of 53.5 mL.

Preparation of Lyophilized SYNAGIS®

(1) For IM injections: One (1) ml of diluent should be added slowly to the vial of lyophilized SYNAGIS® for a final concentration of 100 mg/mL SYNAGIS®. The vial should then be gently swirled for 30 seconds to avoid foaming. Reconstituted SYNAGIS® should stand at room temperature for a minimum of 20 minutes until SYNAGIS® clarifies. The required volume of reconstituted lyophilized SYNAGIS® (100 mg/mL) will be obtained by pooling the contents of as many vials as necessary with a 5 mL syringe.

Dose (mL)=[Volunteer Weight (kg)×Dose Level (3 mg/kg)]÷Drug Concentration (100 mg/mL)

Example: A volunteer who weighs 75.6 kg receives 2.3 mL of SYNAGIS®

(75.6 kg×3 mg/kg)÷100 mg/mL=2.268 mL (rounded to 2.3 mL)

(2) For IV Infusions: Five (5) ml of diluent should be added slowly to the vial of lyophilized SYNAGIS® for a final concentration of 20 mg/mL SYNAGIS®. The vial should then be gently swirled for 30 seconds to avoid foaming Reconstituted SYNAGIS® should stand at room temperature for a minimum of 20 minutes until SYNAGIS® clarifies. The required volume of reconstituted lyophilized SYNAGIS® (20 mg/mL) will be obtained by pooling the contents of as many vials as necessary with a 20 mL (or larger) syringe and injecting this volume into an empty 200 mL infusion bag.

Dose (mL)=[Volunteer Weight (kg)×Dose Level (15 mg/kg)]÷Drug Concentration (20 mg/mL)]

Example: A volunteer who weighs 71.4 kg receives 53.6 mL of SYNAGIS®

(71.4 kg×15 mg/kg)÷20 mg/mL=53.55 mL (rounded to 53.6 mL)

d. Administration of Study Drug

Study drug for the IM and IV treatment groups will be dispensed from the pharmacy in identical appearing 5 mL syringes and identical appearing 200 mL infusion bags, respectively.

IM Infection

The study drug will be administered by IM injection into the deltoid muscle (after confirming the needle is not in a blood vessel) using standard aseptic technique. Volunteers will remain under observation in the study site for at least 30 minutes after the injection IV Infusion Prior to drug administration, an IV catheter will be placed in an accessible vein using standard insertion techniques. Patency of the IV catheter will be maintained by a continuous IV infusion of 5% Dextrose for Injection USP at a rate of 10 to 25 mL/h. The dextrose infusion will be interrupted, and SYNAGIS® will be infused through a low protein binding 0.22 μm filter at a rate of approximately 1-2 mL/minute. After SYNAGIS® has been administered, the IV tubing should be flushed and kept open with 5% Dextrose for Injection USP at 10 to 25 mL/h until the IV catheter is removed.

e. Concomitant Medications

All concomitant medications used by the volunteer from Study Day 0 through Study Day 60 will be recorded on the case report form. Volunteers may not receive the following:

1. Immunosuppressive medication (inhaled and topical corticosteroids are permitted).

2. Investigational agents from 120 days before study entry through Study Day 60.

The sponsor must be notified if any volunteer receives prohibited concomitant medications. Volunteers may receive medications to treat adverse events as deemed necessary by the investigator or the volunteer's physician.

D. Schedule of Volunteer Evaluations

All volunteers who are assigned a PID and receive any study drug will be followed according to the protocol regardless of the number of doses of study drug received, unless consent for follow-up is withdrawn. The sponsor must be notified of all deviations from protocol visits or evaluations and these evaluations, if applicable, must be rescheduled or performed at the nearest possible time to the original schedule.

Volunteers will be instructed to call study personnel to report any abnormalities during the intervals between study visits and to come to the study site if medical evaluation is needed and the urgency of the situation permits. For emergency and other unscheduled visits to a medical facility other than the study site, medical records will be obtained by the investigator. A schedule of screening and on-study visit procedures is presented in Table 4, followed by a detailed description of each visit.

TABLE 4

Schedule of Volunteer Evaluations

|  | Scn | Study Day | | | | | | | | | | |
|---|---|---|---|---|---|---|---|---|---|---|---|---|
|  |  | 0 | 1 | 2 | 3 | 4 | 5 | 7 | 14 | 21 | 30 | 37 | 60 |
| Written Informed Consent | x | | | | | | | | | | | | |
| Verify Eligibility Criteria | x | x | | | | | | | | | | | |
| Medical History | x | | | | | | | | | | | | |
| Physical Examination | x | | | | | | | | | | | | |
| Height and body weight[g] | x | x | | | | | | | | | | $x^d$ | |
| Urinalysis | x | x | | | | | | | X | | | $x^d$ | |

TABLE 4-continued

Schedule of Volunteer Evaluations

|  | Scn | Study Day | | | | | | | | | | | |
| --- | --- | --- | --- | --- | --- | --- | --- | --- | --- | --- | --- | --- | --- |
|  |  | 0 | 1 | 2 | 3 | 4 | 5 | 7 | 14 | 21 | 30 | 37 | 60 |
| Hepatitis A, B, C | x | | | | | | | | | | | | |
| Serum βHCG[b] | x | | | | | | | | | | | | |
| Urine βHCG[b] |  | x | | | | | | | | | $x^d$ | | |
| Serum Chemistry[c] | x | x | | | | | | X | | | | $x^d$ | |
| CBC, Differential, Platelets | x | x | | | | | | X | | | | $x^d$ | |
| SYNAGIS ® Serum Level |  | $x^a$ | x | x | x | x | x | X | x | x | x | $x^d$ | x |
| Anti-SYNAGIS ® Antibody |  | x | | | | | | X | x | x | x | $x^d$ | x |
| Vital Signs[e] |  | x | | | | | | | | | $x^d$ | | |
| Randomization/Assignment of PID |  | x | | | | | | | | | | | |
| Study Drug Injection (IM Groups) |  | x | | | | | | | | | $x^d$ | | |
| Study Drug Infusion (IV Groups) |  | x | | | | | | | | | | | |
| Assessment of Adverse Events[f] |  | x | x | x | x | x | x | X | x | x | x | $x^d$ | x |

[a]Blood will be sampled for SYNAGIS ® serum concentration before dosing, at the end of infusion (IV dose groups only), and at 0.25, 0.5, 1, 4, 8, and 12 hours after injection/end of infusion.
[b]Females only.
[c]ALT, AST, BUN, Creatinine.
[d]IM dose groups only.
[e]Vital signs obtained before and 30 minutes after each dose.
[f]Adverse events through 30 days after each dose. Serious adverse events through Study Day 60.
[g]Body weight only at Study Day 30.

a. Screening

Note: All screening laboratory assessments must be performed within 21 days before study entry (Study Day 0). The screening evaluations may be carried out over more than one visit.

1. Written informed consent
2. Verify eligibility criteria
3. Screening medical history
4. Screening physical examination
5. Height and body weight
6. Urinalysis
7. Blood collection for screening
Serum for hepatitis A antibody, hepatitis B surface antigen, hepatitis C antibody
Serum βHCG (female volunteers only)
Chemistry panel (AST, ALT, BUN, creatinine)
CBC with differential and platelet count Study Day 0: Dose 1
Visit 1
1. Verify eligibility criteria
2. Height and body weight
3. Urinalysis
4. Urine βHCG (female volunteers only)
5. Baseline blood collection
Chemistry panel (AST, ALT, BUN, creatinine)
CBC with differential and platelet count
Serum for SYNAGIS® level
Serum for anti-SYNAGIS® antibody
6. Randomization and assignment of PID
7. Vital signs before administration of study drug (temperature, blood pressure, pulse rate, respiratory rate)
Note: All of the above must be completed before administration of study drug.
1. Administration of study drug
2. Monitor vital signs 30 minutes after injection or end of infusion
3. Monitor for adverse events and serious adverse events
4. Post-dose blood collection
Serum for SYNAGIS® levels immediately after completion of infusion (IV dose groups only) and at 0.25, 0.5, 1, 4, 8, and 12 hours after injection/end of infusion Study Day 1: Dose 1 Pharmacokinetic Sampling
Visit 2
1. Post-dose blood collection for 24 hour SYNAGIS® serum level
2. Monitor for adverse events and serious adverse events Study Day 2: Dose 1 Pharmacokinetic Sampling
Visit 3
1. Post-dose blood collection for 48 hour SYNAGIS® serum level
2. Monitor for adverse events and serious adverse events Study Day 3: Dose 1 Pharmacokinetic Sampling
Visit 4
1. Post-dose blood collection for 72 hour SYNAGIS® serum level
2. Monitor for adverse events and serious adverse events Study Day 4: Dose 1 Pharmacokinetic Sampling
Visit 5
1. Post-dose blood collection for 96 hour SYNAGIS® serum level
2. Monitor for adverse events and serious adverse events Study Day 5: Dose 1 Pharmacokinetic Sampling
Visit 6
1. Post-dose blood collection for 120 hour SYNAGIS® serum level
2. Monitor for adverse events and serious adverse events Study Day 7:
Visit 7
1. Urinalysis
2. Blood collection
Chemistry panel (AST, ALT, BUN, creatinine)
CBC with differential and platelet count
Serum for SYNAGIS® level
Serum for anti-SYNAGIS® antibody 3. Monitor for adverse events and serious adverse events Study Day 14±1:

Visit 8

1. Blood collection

Serum for SYNAGIS® level

Serum for anti-SYNAGIS® antibody

2. Monitor for adverse events and serious adverse events

Study Day 21±1:

Visit 9

1. Blood collection

Serum for SYNAGIS® level

Serum for anti-SYNAGIS® antibody

2. Monitor for adverse events and serious adverse events

Study Day 30±1:

Visit 10

All Volunteers

1. Blood collection

Serum for SYNAGIS® level

Serum for anti-SYNAGIS® antibody

2. Monitor for adverse events and serious adverse events

Volunteers in IM groups only

3. Bodyweight

4. Urine βHCG

5. Vital signs before administration of study drug

6. Administration of study drug

7. Monitor vital signs 30 minutes after injection

Study Day 37±1:

Visit 11

Volunteers in IM groups only

1. Urinalysis

2. Blood collection

Chemistry panel (AST, ALT, BUN, creatinine)

CBC with differential and platelet count

Serum for SYNAGIS® level

Serum for anti-SYNAGIS® antibody

3. Monitor for adverse events and serious adverse events

Study Day 60±2:

Visit 12

1. Blood collection

Serum for SYNAGIS® level

Serum for anti-SYNAGIS® antibody

2. Monitor for serious adverse events

E. Volunteer Evaluation Methods a. Routine Laboratory Evaluations

Routine laboratory tests during screening and during the study will be performed at each study site's local clinical laboratory. Urine pregnancy tests during the study will be performed in the study site using a licensed test. Abnormal laboratory results should be repeated as soon as possible (preferably within 2448 hours).

b. Pharmacokinetic and Immunologic Evaluations

SYNAGIS® serum concentration and anti-SYNAGIS® antibodies will be measured by MedImmune, Inc. by ELISA.

F. Completion of Study and Loss to Follow-Up

Volunteers will be considered to have completed the study if they were followed up through Study Day 60. It should be specified on the case report form whether or not the volunteer completed the study follow-up procedures through Study Day 60. Volunteers will be considered lost-to-follow-up only if no contact has been established by the time the study is completed such that there is insufficient information to determine the volunteer's status at Study Day 60. The investigator should document attempts to re-establish contact with missing volunteers throughout the study period. If contact with a missing volunteer is re-established, follow-up should resume according to the protocol.

Pharmacokinetic and immunologic evaluations will be made based on SYNAGIS® serum concentration and anti-SYNAGIS® antibodies measured by ELISA.

EQUIVALENTS

Those skilled in the art will recognize, or be able to ascertain using no more than routine experimentation, many equivalents to the specific embodiments of the invention described herein. Such equivalents are intended to be encompassed by the following claims.

All publications, patents and patent applications mentioned in this specification are herein incorporated by reference into the specification to the same extent as if each individual publication, patent or patent application was specifically and individually indicated to be incorporated herein by reference.

Citation or discussion of a reference herein shall not be construed as an admission that such is prior art to the present invention.

What is claimed is:

1. An aqueous palivizumab formulation comprising, in an aqueous carrier: (a) at least 75 mg/ml of palivizumab, or an antigen-binding fragment thereof; and (b) histidine, wherein said palivizumab or palivizumab antigen-binding fragment in the formulation is stable at 2° C. to 8° C. for at least 15 months as determined by high performance size exclusion chromatography (HPSEC).

2. An aqueous palivizumab formulation comprising, in an aqueous carrier: (a) at least 75 mg/ml of palivizumab, or an antigen-binding fragment thereof; and (b) histidine, wherein said formulation does not comprise mannitol, and wherein said palivizumab or palivizumab antigen-binding fragment in the formulation is stable at 2° C. to 8° C. for at least 15 months as determined by HPSEC.

3. The formulation of claim 1 or 2, wherein said palivizumab or palivizumab antigen-binding fragment is at a concentration of about 80 mg/ml.

4. The formulation of claim 1 or 2, wherein said palivizumab or palivizumab antigen-binding fragment is at a concentration of at least 80 mg/ml.

5. The formulation of claim 1 or 2, wherein said palivizumab or palivizumab antigen-binding fragment is at a concentration of at least 85 mg/ml at least 90 mg/ml or at least 95 mg/ml.

6. The formulation of claim 1 or 2, wherein the histidine is at a concentration of 1 mM to 100 mM or 10 mM to 50 mM.

7. The formulation of claim 1 or 2, wherein the histidine is at a concentration of 20 mM to 30 mM.

8. The formulation of claim 1 or 2, wherein said formulation comprises an excipient other than a surfactant.

9. The formulation of claim 8, wherein the excipient is glycine.

10. The formulation of claim 9, wherein the glycine is at a concentration of less than 150 mM, less than 100 mM, or less than 50 mM.

11. The formulation of claim 9, wherein the glycine is at a concentration of less than 3 mM or less than 2 mM.

12. The formulation of claim 1 or 2, wherein said formulation is substantially free of surfactants and inorganic salts.

13. The formulation of claim 3, wherein said formulation is substantially free of surfactants, inorganic salts and other excipients.

14. The formulation of claim 1 or 2, wherein said formulation has a pH of between about 5.5 to about 7.0.

15. The formulation of claim 1 or 2, wherein said formulation has a pH of between about 5.5 to about 6.5.

16. The formulation of claim 1 or 2, wherein said palivizumab or palivizumab antigen-binding fragment in the formulation is stable at 20° C. to 24° C. temperature for at least 1 year as determined by HPSEC.

17. The formulation of claim 1 or 2, wherein said aqueous carrier is distilled water.

18. The formulation of claim 1 or 2, wherein said formulation is sterile.

19. The formulation of claim 1 or 2, wherein said palivizumab or palivizumab antigen-binding fragment is conjugated to a therapeutic moiety.

20. The formulation of claim 1 or 2, wherein said palivizumab or palivizumab antigen-binding fragment is conjugated to a detectable substance.

21. A pharmaceutical unit dosage comprising the formulation of claim 1 or 2, which dosage is suitable for administration to a human and is in a suitable container.

22. A sealed container comprising the formulation of claim 1 or 2.

23. An aqueous palivizumab formulation comprising, in an aqueous carrier: (a) at least 75 mg/ml of palivizumab, or an antigen-binding fragment thereof; (b) histidine at a concentration of 23 mM to 27 mM; and (c) glycine at a concentration of less than 2 mM, wherein said formulation has a pH of between about 5.5 to 6.5, and wherein said palivizumab or palivizumab antigen-binding fragment in the formulation is stable at 2° C. to 8° C. for at least 15 months as determined by HPSEC.

24. The formulation of claim 23, wherein histidine is at a concentration of 25 mM.

25. The formulation of claim 23 or 24, wherein glycine is at a concentration of 1.6 mM.

26. The formulation of claim 23, wherein said formulation has a pH of about 6.0.

27. The formulation of claim 26, wherein histidine is a concentration of 25 mM and glycine is a concentration of 1.6 mM.

28. The formulation of claim 23, wherein said palivizumab or palivizumab antigen-binding fragment is at a concentration of about 80 mg/ml.

29. The formulation of claim 27, wherein said palivizumab or palivizumab antigen-binding fragment is at a concentration of about 80 mg/ml.

30. The formulation of claim 23, wherein said palivizumab or palivizumab antigen-binding fragment is at a concentration of at least 80 mg/ml.

31. The formulation of claim 27, wherein said palivizumab or palivizumab antigen-binding fragment is at a concentration of at least 80 mg/ml.

32. The formulation of claim 23 or 27, wherein said palivizumab or palivizumab antigen-binding fragment is at a concentration of at least 85 mg/ml, at least 90 mg/ml or at least 95 mg/ml.

33. The formulation of claim 23, 28 or 30, wherein said formulation is substantially free of surfactants, inorganic salts and other excipients.

34. The formulation of claim 27, 29 or 31, wherein said formulation is substantially free of surfactants, inorganic salts and other excipients.

35. The formulation of claim 23, 28 or 30, wherein said aqueous carrier is distilled water.

36. The formulation of claim 27, 29 or 31, wherein said aqueous carrier is distilled water.

37. The formulation of claim 34, wherein said aqueous carrier is distilled water.

38. The formulation of claim 23, 28 or 30, wherein said formulation is sterile.

39. The formulation of claim 27, 29 or 31, wherein said formulation is sterile.

40. The formulation of claim 37, wherein said formulation is sterile.

41. The formulation of claim 23 or 27, wherein said palivizumab or palivizumab antigen-binding fragment is conjugated to a therapeutic moiety.

42. The formulation of claim 23 or 27 wherein said palivizumab or palivizumab antigen-binding fragment is conjugated to a detectable agent.

43. A pharmaceutical unit dosage form comprising the formulation of claim 23, 28 or 30, which dosage form is suitable for administration to a human and is in a suitable container.

44. A pharmaceutical unit dosage comprising the formulation of claim 27, 29 or 31, which dosage is suitable for administration to a human and is in a suitable container.

45. A sealed container comprising an aqueous palivizumab formulation, wherein said formulation comprises 100 mg/ml of palivizumab or a palivizumab antigen-binding fragment, about 25 mM histidine, and about 1.6 mM glycine in 1.2 ml of distilled water, and wherein said palivizumab or palivizumab antigen-binding fragment in the formulation is stable at 2° C. to 8° C. for at least 15 months as determined by HPSEC.

46. A sealed container comprising an aqueous palivizumab formulation, wherein said formulation: (a) comprises 100 m/l of palivizumab or a palivizumab antigen-binding fragment, about 25 mM histidine, and about 1.6 mM glycine in 1.2 ml of distilled water; and (b) does not comprise mannitol, and wherein said palivizumab or palivizumab antigen-binding fragment in the formulation is stable at 2° C. to 8° C. for at least 15 months as determined by HPSEC.

47. The sealed container of claim 45 or 46, wherein said palivizumab or palivizumab antigen-binding fragment in the formulation is stable at 2° C. to 8° C. for 15 months as determined by HPSEC.

48. The sealed container of claim 45 or 46, wherein said palivizumab or palivizumab antigen-binding fragment in the formulation is stable at 2° C. to 8° C. for at least 3 years as determined by HPSEC.

49. The sealed container of claim 45 or 46, wherein said palivizumab or palivizumab antigen-binding fragment in the formulation is stable at 20° C. to 24° C. for at least 1 year.

50. The sealed container of claim 45 or 46, wherein the aqueous palivizumab formulation contains no more than 3% aggregation by weight protein as measured by HPSEC.

51. The sealed container of claim 45 or 46, wherein the stable aqueous palivizumab formulation contains equal to or more than 98% of the total protein in a single peak as determined by HSPEC and contains no other single peaks having more than 2% of total protein each.

52. The formulation of claim 1 or 2, wherein said palivizumab or palivizumab antigen-binding fragment in the formulation is stable at 2° C. to 8° C. for 15 months as determined by HPSEC.

53. The formulation of claim 1 or 2, wherein said palivizumab or palivizumab antigen-binding fragment in the formulation is stable at 2° C. to 8° C. for at least 3 years as determined by HPSEC.

54. The formulation of claim 1 or 2 which contains no more than 3% aggregation by weight protein as measured by HPSEC.

55. The formulation of claim 1 or 2 which contains equal to or more than 98% of the total protein in a single peak as determined by HSPEC and contains no other single peaks having more than 2% of total protein each.

56. The formulation of claim 23 or 27, wherein said palivizumab or palivizumab antigen-binding fragment in the formulation is stable at 2° C. to 8° C. for 15 months as determined by HPSEC.

57. The formulation of claim 23 or 27, wherein said palivizumab or palivizumab antigen-binding fragment in the formulation is stable at 2° C. to 8° C. for at least 3 years as determined by HPSEC.

58. The formulation of claim 23 or 27, wherein said palivizumab or palivizumab antigen-binding fragment in the formulation is stable at 20° C. to 24° C. for at least 1 year.

59. The formulation of claim 23 or 27 which contains no more than aggregation by weight protein as measured by HPSEC.

60. The formulation of claim 23 or 27 which contains equal to or more than 98% of the total protein in a single peak as determined by HPSEC and contains no other single peaks having inure than 2% of total protein each.

61. An aqueous palivizumab formulation comprising, in an aqueous carrier: (a) at least 75 mg/ml of palivizumab, or an antigen-binding fragment thereof; (b) histidine at a concentration of 23 mM to 27 mM; and (c) glycine at a concentration of less than 2 mM, wherein said formulation has a pH of between about 5.5 to 6.5 and does not comprise mannitol, and wherein said palivizumab or palivizumab antigen-binding fragment in the formulation is stable at 2° C. to 8° C. for at least 15 months as determined by HPSEC.

62. The formulation of claim 61, wherein histidine is at a concentration of 25 mM.

63. The formulation of claim 61 or 62, wherein glycine is at a concentration of 1.6 mM.

64. The formulation of claim 61, wherein said formulation has a pH of about 6.0.

65. The formulation of claim 64, wherein histidine is a concentration of 25 mM and glycine is a concentration of 1.6 mM.

66. The formulation of claim 61, wherein said palivizumab or palivizumab antigen-binding fragment is at a concentration of about 80 mg/ml.

67. The formulation of claim 65, wherein said palivizumab or palivizumab antigen-binding fragment is at a concentration of about 80 mg/ml.

68. The formulation of claim 61, wherein said palivizumab or palivizumab antigen-binding fragment is at a concentration of at least 80 mg/ml.

69. The formulation of claim 65, wherein said palivizumab or palivizumab antigen-binding fragment is at a concentration of at least 80 mg/ml.

70. The formulation of claim 61 or 65, wherein said palivizumab or palivizumab antigen-binding fragment is at a concentration of at least 85 mg/ml, at least 90 mg/ml or at least 95 mg/ml.

71. The formulation of claim 61, 62 or 66 wherein said formulation is substantially free of surfactants, inorganic salts and other excipients.

72. The formulation of claim 65, 67 or 69, wherein said formulation is substantially free of surfactants, inorganic salts and other excipients.

73. The formulation of claim 61, 62 or 66, wherein said aqueous carrier is distilled water.

74. The formulation of claim 65, 67 or 69, wherein said aqueous carrier is distilled water.

75. The formulation of claim 72, wherein said aqueous carrier is distilled water.

76. The formulation of claim 61, 62 or 66, wherein said formulation is sterile.

77. The formulation of claim 65, 67 or 69, wherein said formulation is sterile.

78. The formulation of claim 75, wherein said formulation is sterile.

79. The formulation of claim 61 or 65, wherein said palivizumab or palivizumab antigen-binding fragment is conjugated to a therapeutic moiety.

80. The formulation of claim 61 or 65, wherein said palivizumab or palivizumab antigen-binding fragment is conjugated to a detectable agent.

81. A pharmaceutical unit dosage form comprising the formulation of claim 61, 62 or 66, which dosage form is suitable for administration to a human and is in a suitable container, 82. A pharmaceutical unit dosage comprising the formulation of claim 65, 67 or 69, which dosage is suitable for administration to a human and is in a suitable container.

* * * * *

UNITED STATES PATENT AND TRADEMARK OFFICE
CERTIFICATE OF CORRECTION

PATENT NO. : 7,785,592 B2  
APPLICATION NO. : 11/906543  
DATED : August 31, 2010  
INVENTOR(S) : Oliver et al.

Page 1 of 1

It is certified that error appears in the above-identified patent and that said Letters Patent is hereby corrected as shown below:

In claim 5, column 54, line 60, replace "85 mg/ml at least 90 mg/ml" with --85 mg/ml, at least 90 mg/ml--

In claim 27, column 55, line 53, replace "is a" with --is at a--

In claim 27, column 55, line 54, replace "is a" with --is at a--

In claim 38, column 56, line 18, replace "sterile," with --sterile.--

In claim 42, column 56, line 26, replace "27 wherein" with --27, wherein--

In claim 46, column 56, line 44, replace "100 m/l" with --100 mg/ml--

In claim 59, column 57, line 31, replace "than aggregation" with --than 3% aggregation--

In claim 60, column 57, line 36, replace "inure" with --more--

In claim 65, column 58, line 1, replace "is a" with --is at a--

In claim 65, column 58, line 2, replace "is a" with --is at a--

Signed and Sealed this  
Twenty-ninth Day of March, 2011

David J. Kappos  
*Director of the United States Patent and Trademark Office*